United States Patent
Stockley et al.

(10) Patent No.: US 11,084,821 B2
(45) Date of Patent: Aug. 10, 2021

(54) CYANOPYRROLIDINE DERIVATIVES WITH ACTIVITY AS INHIBITORS OF USP30

(71) Applicant: MISSION THERAPEUTICS LIMITED, Cambridge (GB)

(72) Inventors: Martin Lee Stockley, Cambridge (GB);
Mark Ian Kemp, Cambridge (GB);
Andrew Madin, Cambridge (GB)

(73) Assignee: MISSION THERAPEUTICS LIMITED, Cambridge (GB)

(*) Notice: Subject to any disclaimer, the term of this patent is extended or adjusted under 35 U.S.C. 154(b) by 39 days.

(21) Appl. No.: 16/336,202

(22) PCT Filed: Oct. 2, 2017

(86) PCT No.: PCT/GB2017/052949
§ 371 (c)(1),
(2) Date: Mar. 25, 2019

(87) PCT Pub. No.: WO2018/060742
PCT Pub. Date: Apr. 5, 2018

(65) Prior Publication Data
US 2020/0199126 A1    Jun. 25, 2020

(30) Foreign Application Priority Data

Sep. 30, 2016 (GB) .................... 1616627

(51) Int. Cl.
| | | |
|---|---|---|
| C07D 487/04 | (2006.01) |
| C07D 401/12 | (2006.01) |
| C07D 403/12 | (2006.01) |
| C07D 417/12 | (2006.01) |
| C07D 471/04 | (2006.01) |
| C07D 498/04 | (2006.01) |
| A61K 31/407 | (2006.01) |

(52) U.S. Cl.
CPC ......... *C07D 487/04* (2013.01); *C07D 401/12* (2013.01); *C07D 403/12* (2013.01); *C07D 417/12* (2013.01); *C07D 471/04* (2013.01); *C07D 498/04* (2013.01)

(58) Field of Classification Search
CPC ... C07D 487/04; C07D 471/04; C07D 498/04
See application file for complete search history.

(56) References Cited

U.S. PATENT DOCUMENTS

| 10,683,269 B2 * | 6/2020 | Gibson ............... C07D 417/12 |
| 2008/0300268 A1 | 12/2008 | Singh et al. |
| 2009/0264499 A1 | 10/2009 | Deng et al. |

FOREIGN PATENT DOCUMENTS

| WO | 0177073 A1 | 10/2001 |
| WO | 2009129365 A1 | 10/2009 |
| WO | 2009129370 A1 | 10/2009 |
| WO | 2013030218 A1 | 3/2013 |
| WO | 2014041111 A1 | 3/2014 |
| WO | 2014068527 A1 | 5/2014 |
| WO | 2014188173 A1 | 11/2014 |
| WO | 2015017502 A1 | 2/2015 |
| WO | 2015054555 A1 | 4/2015 |
| WO | 2015061247 A2 | 4/2015 |
| WO | 2015140566 A1 | 9/2015 |
| WO | 2015179190 A1 | 11/2015 |
| WO | 2016004272 A1 | 1/2016 |
| WO | 2016019237 A2 | 2/2016 |
| WO | 2016/046530 A1 | 3/2016 |
| WO | 2016065236 A1 | 4/2016 |
| WO | 2016156816 A1 | 10/2016 |
| WO | WO-2016156816 A1 * | 10/2016 ........... C07D 471/04 |
| WO | 2016192074 A1 | 12/2016 |
| WO | 2017/009650 A1 | 1/2017 |
| WO | 2017/093718 A1 | 6/2017 |
| WO | 2017/109488 A1 | 6/2017 |
| WO | 2017103614 A1 | 6/2017 |
| WO | 2017/141036 A1 | 8/2017 |
| WO | 2017/149313 A1 | 9/2017 |
| WO | 2017/158388 A1 | 9/2017 |
| WO | 2017158381 A1 | 9/2017 |
| WO | 2017163078 A1 | 9/2017 |
| WO | 2018060689 A1 | 4/2018 |
| WO | 2018060691 A1 | 4/2018 |
| WO | 2018065768 A1 | 4/2018 |
| WO | 2018220355 A1 | 12/2018 |
| WO | 2018234775 A1 | 12/2018 |

OTHER PUBLICATIONS

The International Search Report and Written Opinion, dated Dec. 22, 2017, in the corresponding PCT Appl. No. PCT/GB2017/052949.

Falgueyret et al., "Novel, Nonpeptidic Cyanamides as Potent and Reversible Inhibitors of Human Cathepsins K and L," J. Med. Chem. 2001, 44, 94-104.

Laine et al., "Discovery of Novel Cyanamide-Based Inhibitors of Cathepsin C," ACS Med. Chem. Lett. 2011, 2, 142-147.

(Continued)

*Primary Examiner* — Amanda L. Aguirre

(57) ABSTRACT

The present invention relates to a class of substituted-cyanopyrrolidines of Formula (I) with activity as inhibitors of deubiquitilating enzymes, in particular, ubiquitin C-terminal hydrolase 30 or ubiquitin specific peptidase 30 (USP30), having utility in a variety of therapeutic areas including cancer and conditions involving mitochondrial dysfunction.

(Formula ((I))

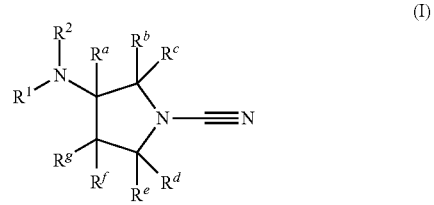

(I)

19 Claims, No Drawings

(56) References Cited

OTHER PUBLICATIONS

Ward et al., "Quantitative Chemical Proteomic Profiling of Ubiquitin Specific Proteases in Intact Cancer Cells," ACS Chem. Biol. 2016, 11, 3268-3272.

Rydzewski et al, "Peptidic 1-Cyanopyrrolidines: Synthesis and SAR of a Series of Potent, Selective Cathepsin Inhibitors", Bioorganic & Medicinal Chemistry 10 (2002) 3277-3284.

Deaton et al, "Novel and potent cyclic cyanamide-based cathepsin K inhibitors", Bioorganic & Medicinal Chemistry Letters 15 (2005) 1815-1819.

Oballa et al, "A generally applicable method for assessing the electrophilicity and reactivity of diverse nitrile-containing compounds", Bioorganic & Medicinal Chemistry Letters 17 (2007) 998-1002.

Zapf et al, "Covalent Inhibitors of Interleukin-2 Inducible T Cell Kinase (Itk) with Nanomolar Potency in a Whole-Blood Assay", J. Med. Chem. 2012, 55, 10047-10063.

Nakamura et al, "Regulation of Mitochondrial Morphology by USP30, a Deubiquitinating Enzyme Present in the Mitochondrial Outer Membrane", Molecular Biology of the Cell, vol. 19, 1903-1911, May 2008.

Bingol et al, "The mitochondrial deubiquitinase USP30 opposes parkin-mediated mitophagy", Nature vol. 510, 370-375, 2014.

Liang et al, "USP30 deubiquitylates mitochondrial Parkin substrates and restricts apoptotic cell death", EMBO Reports, 1-10, 2015; DOI 10.15252/embr.201439820.

Komander et al, "Breaking the chains: structure and function of the deubiquitinases", Nature Reviews Molecular Cell Biology, 10, 550-563, 2009.

Bedford et al., "Ubiquitin-like protein conjugation and the ubiquitin-proteasome system as drug targets", Nature Rev. Drug Discovery, 10:29-46, 2011.

\* cited by examiner

CYANOPYRROLIDINE DERIVATIVES WITH ACTIVITY AS INHIBITORS OF USP30

This application is a National Stage Application of PCT/GB2017/052949 filed Oct. 2, 2017, which claims priority from UK Patent Application No. 1616627.4 filed on Sep. 30, 2016. The priority of said PCT and UK Patent Application are claimed.

The present invention relates to a class of substituted-cyanopyrrolidines with activity as inhibitors of deubiquitilating enzymes, in particular, ubiquitin C-terminal hydrolase 30 or ubiquitin specific peptidase 30 (USP30), uses thereof, processes for the preparation thereof and composition containing said inhibitors. These inhibitors have utility in a variety of therapeutic areas including cancer and conditions involving mitochondrial dysfunction.

Ubiquitin is a small protein consisting of 76 amino acids that is important for the regulation of protein function in the cell. Ubiquitylation and deubiquitylation are enzymatically mediated processes by which ubiquitin is covalently bound or cleaved from a target protein by deubiquitylating enzymes (DUBs), of which there are approximately 95 DUBs in human cells, divided into sub-families based on sequence homology. The USP family are characterised by their common Cys and His boxes which contain Cys and His residues critical for their DUB activities. The ubiquitylation and deubiquitylation processes have been implicated in the regulation of many cellular functions including cell cycle progression, apoptosis, modification of cell surface receptors, regulation of DNA transcription and DNA repair. Thus, the ubiquitin system has been implicated in the pathogenesis of numerous disease states including inflammation, viral infection, metabolic dysfunction, CNS disorders, and oncogenesis.

Ubiquitin is a master regulator of mitochondrial dynamics. Mitochondria are dynamic organelles whose biogenesis, fusion and fission events are regulated by the post-translational regulation via ubiquitylation of many key factors such as mitofusins. While ubiquitin ligases such as parkin are known to ubiquitylate a number of mitochondrial proteins, until recently, deubiquitylating enzymes remained elusive. USP30 is a 517 amino acid protein which is found in the mitochondrial outer membrane (Nakamura et al., Mol Biol 19:1903-11, 2008). It is the sole deubiquitylating enzyme bearing a mitochondrial addressing signal and has been shown to deubiquitylate a number of mitochondrial proteins. It has been demonstrated that USP30 opposes parkin-mediated mitophagy and that reduction of USP30 activity can rescue parkin-mediated defects in mitophagy.

Mitochondrial dysfunction can be defined as diminished mitochondrial content (mitophagy or mitochondrial biogenesis), as a decrease in mitochondrial activity and oxidative phosphorylation, but also as modulation of reactive oxygen species (ROS) generation. Hence a role for mitochondrial dysfunctions in a very large number of aging processes and pathologies including but not limited to, neurodegenerative diseases (e.g. Parkinson's disease (PD), Alzheimer's disease, Huntington's disease, Amylotrophic Lateral Sclerosis (ALS), multiple sclerosis), cancer, diabetes, metabolic disorders, cardio-vascular diseases, psychiatric diseases (e.g. Schizophrenia), and osteoarthritis.

For example, Parkinson's disease affects around 10 million people worldwide (Parkinson's Disease Foundation) and is characterised by the loss of dopaminergic neurons in the substantia nigra. The exact mechanisms underlying PD are unclear; however mitochondrial dysfunction is increasingly appreciated as a key determinant of dopaminergic neuronal susceptibility in PD and is a feature of both familial and sporadic disease, as well as in toxin-induced Parkinsonism. Parkin is one of a number of proteins that have been implicated with early onset PD. While most PD cases are linked to defects in alpha-synuclein, 10% of Parkinson's cases are linked to specific genetic defects, one of which is in the ubiquitin E3 ligase parkin. Parkin and the protein kinase PTEN-induced putative kinase 1 (PINK1) collaborate to ubiquitylate mitochondrial membrane proteins of damaged mitochondria resulting in mitophagy. Dysregulation of mitophagy results in increased oxidative stress, which has been described as a characteristic of PD. Inhibition of USP30 could therefore be a potential strategy for the treatment of PD. For example, PD patients with parkin mutations leading to reduced activity could be therapeutically compensated by inhibition of USP30.

It has been reported that depletion of USP30 enhances mitophagic clearance of mitochondria and also enhances parkin-induced cell death. USP30 has also been shown to regulate BAX/BAK-dependent apoptosis independently of parkin over expression. Depletion of USP30 sensitises cancer cells to BH-3 mimetics such as ABT-737, without the need for parkin over expression. Thus, an anti-apoptotic role has been demonstrated for USP30 and USP30 is therefore a potential target for anti-cancer therapy.

The ubiquitin-proteasome system has gained interest as a target for the treatment of cancer following the approval of the proteasome inhibitor bortezomib (Velcade®) for the treatment of multiple myeloma. Extended treatment with bortezomib is limited by its associated toxicity and drug resistance. However, therapeutic strategies that target specific aspects of the ubiquitin-proteasome pathway upstream of the proteaseome, such as DUBs, are predicted to be better tolerated (Bedford et al., Nature Rev 10:29-46, 2011).

Accordingly, there is a need for compounds that are inhibitors of USP30 for the treatment of indications where inhibition of USP30 is indicated.

Series of cyano-substituted-heterocycles are disclosed as deubiquitylating enzyme inhibitors in PCT applications WO 2016/046530, WO 2016/156816, WO 2017/009650, WO 2017/093718, WO 2017/103614, and PCT/GB2017/050830. Falgueyret et al., J. Med. Chem. 2001, 44, 94-104, and PCT application WO 01/77073 refer to cyanopyrrolidines as inhibitors of Cathepsins K and L, with potential utility in treating osteoporosis and other bone-resorption related conditions. PCT application WO 2015/179190 refers to N-acylethanolamine hydrolysing acid amidase inhibitors, with potential utility in treating ulcerative colitis and Crohn's disease. PCT application WO 2013/030218 refers to quinazolin-4-one compounds as inhibitors of ubiquitin specific proteases, such as USP7, with potential utility in treating cancer, neurodegenerative diseases, inflammatory disorders and viral infections. PCT applications WO 2014/068527, WO 2014/188173, WO 2015/017502, WO 2015/061247, WO 2016/019237 and WO 2016/192074 refer to inhibitors of Bruton's tyrosine kinase with potential utility in treating disease such as autoimmune disease, inflammatory disease and cancer. PCT applications WO 2009/026197, WO 2009/129365, WO 2009/129370, and WO 2009/129371, refer to cyanopyrrolidines as inhibitors of Cathepsin C with potential utility in treating COPD. United States patent application US 2008/0300268 refers to polyaromatic compounds as inhibitors of tyrosine kinase receptor PDGFR.

According to a first aspect, the present invention provides a compound of formula (I)

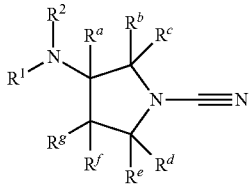

a tautomer thereof, or a pharmaceutically acceptable salt of said compound or tautomer, wherein:

$R^a$ is selected from hydrogen, cyano, and optionally substituted $C_1$-$C_3$ alkyl; or $R^a$ is linked to $R^g$ or $R^b$ to form an optionally substituted $C_3$-$C_4$ cycloalkyl ring;

$R^b$, $R^c$, $R^d$ and $R^e$ are each independently selected from hydrogen, optionally substituted $C_1$-$C_3$ alkyl, and one or more spirocyclic groups where $R^b$ is linked to $R^c$, or $R^d$ is linked to $R^e$; or $R^b$ is linked to $R^a$ to form an optionally substituted $C_3$-$C_4$ cycloalkyl, or $R^e$ is linked to $R^f$ to form an optionally substituted $C_3$-$C_4$ cycloalkyl;

$R^f$ and $R^g$ are each independently selected from hydrogen, fluoro, cyano, optionally substituted $C_1$-$C_3$ alkyl, optionally substituted $C_1$-$C_3$ alkoxy, and a spirocyclic group where $R^f$ and $R^g$ are linked; or $R^f$ is linked to $R^e$ to form an optionally substituted $C_3$-$C_4$ cycloalkyl, or $R^g$ is linked to $R^a$ to form an optionally substituted $C_3$-$C_4$ cycloalkyl;

$R^1$ is selected from hydrogen and optionally substituted $C_1$-$C_3$ alkyl; or $R^1$ is linked to $R^g$ to form the structure (IA):

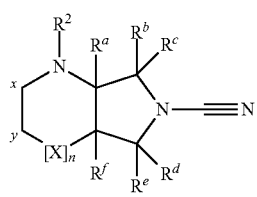

n is 0 or 1;

X is selected from O, N($R^h$), and C($R^i$)($R^j$);

positions x and y may be optionally substituted;

$R^h$ is selected from hydrogen, C(O)R', optionally substituted $C_1$-$C_3$ alkyl, and optionally substituted 3 to 6-membered heterocyclyl, cycloalkyl, heteroaryl or aryl ring;

R' is selected from optionally substituted $C_1$-$C_3$ alkyl, and optionally substituted 3 to 10-membered monocyclic or bicyclic heteroaryl, aryl, heterocyclyl or cycloalkyl ring;

$R^i$ and $R^j$ are each independently selected from hydrogen, fluoro, cyano, optionally substituted $C_1$-$C_3$ alkyl, optionally substituted $C_1$-$C_3$ alkoxy, and optionally substituted 3 to 6-membered heterocyclyl, cycloalkyl, heteroaryl or aryl ring;

when X is O or N($R^h$), $R^f$ is not fluoro or optionally substituted $C_1$-$C_3$ alkoxy;

$R^2$ is a 5 to 10-membered, monocyclic or bicyclic, heteroaryl or aryl ring, which may be unsubstituted, or substituted with one or more $Q^1(R^3)_m$ groups, which may be the same or different;

m is 0 or 1;

$Q^1$ is selected from $Q^{1a}$ or $Q^{1b}$;

$Q^{1a}$ is selected from oxo, halo, cyano, nitro, hydroxyl, $SR^6$, $NR^6R^7$, $CONR^6R^7$, $C_0$-$C_3$-alkylene-$NR^6COR^7$, $NR^6CONR^7R^8$, $COR^6$, $C(O)OR^6$, $SO_2R^6$, $SO_2NR^6R^7$, $NR^6SO_2R^7$, $NR^6SO_2NR^7R^8$, $NR^6C(O)OR^7$, optionally substituted $C_1$-$C_6$ alkyl, optionally substituted $C_1$-$C_6$ alkoxy, and optionally substituted $C_2$-$C_6$ alkenyl;

$Q^{1b}$ is selected from a covalent bond, an oxygen atom, a sulphur atom, $OR^9$, SO, $SO_2$, CO, C(O)O, $C_0$-$C_3$ alkylene-C(O)$NR^6$—$C_0$-$C_3$ alkylene, $C_0$-$C_3$ alkylene-$NR^6$—$C_0$-$C_3$ alkylene, $C_0$-$C_3$ alkylene-$NR^6C(O)$—$C_0$-$C_3$ alkylene, $NR^6CONR^7$, $SO_2NR^6$, $NR^6SO_2$, $NR^6SO_2NR^7$, $NR^6C(O)O$, $NR^6C(O)OR^9$, optionally substituted $C_1$-$C_6$ alkylene, and optionally substituted $C_2$-$C_6$ alkenylene;

$R^3$ is a 3 to 10-membered, monocyclic or bicyclic, heterocyclyl, heteroaryl, cycloalkyl or aryl ring;

$R^6$, $R^7$ and $R^8$ are each independently selected from hydrogen and optionally substituted $C_1$-$C_6$ alkyl; $R^9$ is optionally substituted $C_1$-$C_6$ alkylene;

wherein $R^3$ may be unsubstituted, or substituted with one or more substituents, each independently selected from halo, cyano, oxo, nitro, hydroxyl, Se, optionally substituted $C_1$-$C_6$ alkyl, optionally substituted $C_1$-$C_6$ alkoxy, optionally substituted $C_2$-$C_6$ alkenyl, optionally substituted $C_2$-$C_6$ alkynyl, $Q^{2a}$-$R^{13}$, $Q^{2a}$-O-$Q^{2b}$-$R^{13}$, $Q^{2a}$-S-$Q^{2b}$-$R^{13}$, $Q^{2a}$-SO-$Q^{2b}$-$R^{13}$, $Q^{2a}$-$NR^{10}CONR^{11}R^{12}$, $Q^{2a}$-$NR^{10}CONR^{11}$-$Q^{2a}$-$R^{13}$, $Q^{2a}$-$NR^{10}R^{11}$, $Q^{2a}$-$NR^{10}$-$Q^{2b}$-$R^{13}$, $Q^{2a}$-$COR^{10}$, $Q^{2a}$-CO-$Q^{2b}$-$R^{13}$, $Q^{2a}$-$NR^{10}COR^{11}$, $Q^{2a}$-$NR^{10}CO$-$Q^{2b}$-$R^{13}$, $Q^{2a}$-$NR^{10}C(O)OR^{11}$, $Q^{2a}$-$NR^{10}C(O)O$-$Q^{2b}$-$R^{13}$, $Q^{2a}$-$SO_2R^{10}$, $Q^{2a}$-$SO_2$-$Q^{2b}$-$R^{13}$, $Q^{2a}$-$CONR^{10}R^{11}$, $Q^{2a}$-$CONR^{10}$C-$Q^{2b}$-$R^{13}$, $Q^{2a}$-$CO_2R^{10}$, $Q^{2a}$-$CO_2$-$Q^{2b}$-$R^{13}$, $Q^{2a}$-$SO_2NR^{10}R^{11}$, $Q^{2a}$-$SO_2NR^{10}$-$Q^{2b}$-$R^{13}$, $Q^{2a}$-$NR^{10}SO_2R^{11}$, $Q^{2a}$-$CO_2R^{10}$, $Q^a$-$CO_2$-$Q^{2b}$-$R^{13}$, $Q^{2a}$-$NR^{10}SO_2NR^{11}R^{12}$, and $Q^{2a}$-$NR^{10}SO_2NR^{11}$-$Q^{2b}$-$R^{13}$;

$Q^{2a}$ and $Q^{2b}$ are each independently selected from a covalent bond, optionally substituted $C_1$-$C_6$ alkylene, and optionally substituted $C_2$-$C_6$ alkenylene;

$R^{10}$, $R^{11}$ and $R^{12}$ are each independently selected from hydrogen and optionally substituted $C_1$-$C_6$ alkyl; and $R^{13}$ is selected from optionally substituted heterocyclyl, optionally substituted heteroaryl, optionally substituted aryl, and optionally substituted cycloalkyl;

for use in the treatment of a disorder or condition where inhibition of USP30 is known, or can be shown, to produce a beneficial effect, in a mammal.

The definitions and explanations below are for the terms as used throughout this entire document including both the specification and the claims. Reference to compounds as described herein (e.g. a compound of formula (I)), includes reference to formula (I) including any sub-generic embodiments thereof, e.g. formula II, IIA, IIB, IIC and IID.

Unless otherwise indicated, the term substituted means substituted by one or more defined groups. In the case where groups may be selected from more than one alternatives, the selected groups may be the same or different. The term independently means that where more than one substituent is selected from more than one possible substituents, those substituents may be the same or different.

Unless otherwise indicated, alkyl, alkenyl, and alkoxy groups, including the corresponding divalent radicals, may be straight or branched and contain 1 to 6 carbon atoms and typically 1 to 4 carbon atoms. Examples of alkyl include methyl, ethyl, n-propyl, isopropyl, n-butyl, isobutyl, sec-butyl, pentyl and hexyl. Examples of alkoxy include methoxy, ethoxy, isopropoxy and n-butoxy.

$C_x$-$C_y$ alkyl refers to a saturated aliphatic hydrocarbon group having x-y carbon atoms which may be linear or branched. For example $C_1$-$C_6$ alkyl contains from 1 to 6 carbon atoms and includes $C_1$, $C_2$, $C_3$, $C_4$, $C_5$ and $C_6$. "Branched" means that at least one carbon branch point is present in the group. For example, tert-butyl and isopropyl are both branched groups. Examples of $C_1$-$C_6$ alkyl groups include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl and n-hexyl. $C_1$-$C_6$ alkyl, $C_1$-$C_4$ alkyl and $C_1$-$C_3$ alkyl within the definitions of $R^a$, $R^b$, $R^c$, $R^d$, $R^e$, $R^f$, $R^g$, $R^h$, $R'$, $R^i$, $R^j$, $R^1$, $R^4$, $R^5$, $R^6$, $R^7$, $R^8$, $R^{10}$, $R^{11}$, $R^{12}$, $Q^{1a}$, and within the definition of substituents for $R^3$, may be unsubstituted or substituted with one or more of the substituents defined herein. Examples of substituted $C_1$-$C_6$ alkyl therefore include $CF_3$, $CH_2CF_3$, $CH_2CN$, $CH_2OH$ and $CH_2CH_2OH$.

A $C_x$-$C_y$ alkylene group or moiety may be linear or branched and refers to a divalent hydrocarbon group having one less hydrogen atom from $C_x$-$C_y$ alkyl as defined above. $C_1$-$C_6$ alkylene may include intervening heteroatoms such as oxygen, and therefore includes alkyleneoxy groups. Alkyleneoxy as employed herein also extends to embodiments in which the or an oxygen atom (e.g. a single oxygen atom) is located within the alkylene chain, for example $CH_2CH_2OCH_2$ or $CH_2OCH_2$. Examples of $C_1$-$C_6$ alkylene groups include methylene, methyleneoxy, ethylene, ethyleneoxy, n-propylene, n-propyleneoxy, n-butylene, n-butyleneoxy, methylmethylene and dimethylmethylene. Unless stated otherwise, $C_1$-$C_6$ alkylene, $C_1$-$C_4$ alkylene and $C_1$-$C_3$ alkylene within the definitions of $R^9$, $Q^{1b}$, $Q^{2a}$ and $Q^{2b}$ may be unsubstituted or substituted with one or more of the substituents defined herein. $C_2$-$C_6$ alkenyl refers to a linear or branched hydrocarbon chain radical containing at least two carbon atoms and at least one double bond and includes $C_2$-$C_4$ alkenyl. Examples of alkenyl groups include ethenyl, propenyl, 2-propenyl, 1-butenyl, 2-butenyl, 1-hexenyl, 2-methyl-1-propenyl, 1,2-butadienyl, 1,3-pentadienyl, 1,4-pentadienyl and 1-hexadienyl. Unless stated otherwise, $C_2$-$C_6$ alkenyl within the definitions of $Q^1a$ and within the definition of substituents for $R^3$, may be unsubstituted or substituted with one or more of the substituents defined herein.

$C_2$-$C_6$ alkenylene refers to a linear or branched hydrocarbon group having one less hydrogen atom from $C_2$-$C_6$ alkenyl as defined above. Examples of $C_2$-$C_6$ alkenylene include ethenylene, propenylene and butenylene. Unless stated otherwise, $C_2$-$C_6$ alkenylene and $C_2$-$C_4$ alkenylene within the definition of substituents for $Q^{1b}$, $Q^{2a}$, $Q^{2b}$, may be unsubstituted or substituted with one or more of the substituents defined herein.

$C_2$-$C_6$ alkynyl refers to a linear or branched hydrocarbon chain radical containing at least two carbon atoms and at least one triple bond. Examples of alkenyl groups include ethynyl, propynyl, 2-propynyl, 1-butynyl, 2-butynyl and 1-hexynyl. Unless specified otherwise, $C_2$-$C_6$ alkynyl, within the definition of substituents for $R^3$, may be unsubstituted or substituted with one or more of the substituents defined herein.

$C_1$-$C_6$ alkoxy refers to a group or part of a group having an O—$C_x$-$C_y$ alkyl group according to the definition of $C_x$-$C_y$ alkyl above. $C_1$-$C_6$ alkoxy contains from 1 to 6 carbon atoms and includes $C_1$, $C_2$, $C_3$, $C_4$, $C_5$ and $C_6$. Examples of $C_1$-$C_6$ alkoxy include methoxy, ethoxy, propoxy, isopropoxy, butoxy, pentoxy and hexoxy. Alkoxy as employed herein also extends to embodiments in which the or an oxygen atom (e.g. a single oxygen atom) is located within the alkyl chain, for example $CH_2CH_2OCH_3$ or $CH_2OCH_3$. Thus the alkoxy may be linked through carbon to the remainder of the molecule, for example, $CH_2CH_2OCH_3$, or alternatively, the alkoxy is linked through oxygen to the remainder of the molecule, for example $OC_{1-6}$ alkyl. In one instance, the alkoxy is linked through oxygen to the remainder of the molecule but the alkoxy group contains a further oxygen atom, for example, $OCH_2CH_2OCH_3$. Unless specified otherwise, $C_1$-$C_6$ alkoxy and $C_1$-$C_3$ alkoxy within the definitions $R^f$, $R^g$, $R^i$, $R^j$, $Q^{1a}$, and within the definition of substituents for $R^3$, may be unsubstituted or substituted with one or more of the substituents defined herein. Examples of substituted $C_1$-$C_6$ alkoxy therefore include $OCF_3$, $OCHF_2$, $OCH_2CF_3$, $CH_2CH_2OCH_3$ and $CH_2CH_2OCH_2CH_3$.

The term halo refers to chloro, bromo, fluoro or iodo, in particular chloro or fluoro. Haloalkyl and haloalkoxy groups may contain one or more halo substituents. Examples are trifluoromethyl and trifluoromethoxy. The term "oxo" means =O. The term "nitro" means $NO_2$ and includes $SF_5$ (a known mimetic of nitro).

Cycloalkyl, heterocyclyl, aryl and heteroaryl rings disclosed herein and within the definitions of $R^a$, $R^b$, $R^e$, $R^f$, $R^g$, $R^h$, $R^i$, $R^j$, $R'$, $R^2$, $R^3$ and $R^{13}$ may be monocyclic or bicyclic. Bicyclic ring systems include bridged, fused and spiro ring systems. In particular, the bicyclic ring systems are fused ring systems. A substituent if present may be attached to any suitable ring atom which may be a carbon atom or, in the case of heteroaryl and heterocyclic ring systems, a heteroatom.

"cycloalkyl" refers to a monocyclic saturated or partially unsaturated, non-aromatic ring, wherein all of the ring atoms are carbon, and having the number of ring atoms as indicated. For example, $C_3$-$C_{10}$ cycloalkyl refers to a monocyclic or bicyclic hydrocarbon ring containing 3 to 10 carbon atoms. Examples of $C_3$-$C_{10}$ cycloalkyl are cyclopropyl, cyclobutyl, cyclopentyl, cyclohexyl, cycloheptyl, cyclooctyl and decahydronaphthalenyl. Bicyclic cycloalkyl groups include bridged ring systems such as bicycloheptane and bicyclooctane. Unless specified otherwise, cycloalkyl within the definitions of $R^a$, $R^b$, $R^e$, $R^f$, $R^g$, $R^h$, $R'$, $R^i$, $R^j$, $R^3$, $R^{13}$, may be unsubstituted or substituted with one or more of the substituents defined herein.

An "aryl" group/moiety refers to any monocyclic or bicyclic hydrocarbon group comprising at least one aromatic group and having from 5 to 10 carbon atom ring members. Examples of aryl groups include phenyl and naphthyl. Bicyclic rings may be fused aromatic rings where both rings are aromatic, for example, naphthalenyl. Preferred aryl groups are phenyl and naphthyl, more preferably phenyl. Unless specified otherwise, aryl within the definitions of $R^h$, $R'$, $R^i$, $R^j$, $R^2$, $R^3$ and $R^{13}$, may be unsubstituted or substituted with one or more of the substituents defined herein.

"Heteroaryl" as used herein means a polyunsaturated, monocyclic or bicyclic 5 to 10-membered aromatic moiety containing at least one and up to 5 heteroatoms, particularly 1, 2 or 3 heteroatoms selected from N, O and S, and the remaining ring atoms are carbon atoms, in stable combinations known to the skilled person. Heteroaryl ring nitrogen and sulphur atoms are optionally oxidised, and the nitrogen atom(s) are optionally quaternized. A heteroaryl ring can be a single aromatic ring or a fused bicyclic ring where the bicyclic ring system can be aromatic, or one of the fused rings is aromatic and the other is at least partially saturated. Examples of fused rings where one of the rings is aromatic and the other is at least partially saturated include tetrahydropyridopyrazinyl, tetrahydroquinolinyl and tetrahydroisoquinolinyl. In such instances, attachment of the bicyclic ring to the group it is a substituent of relative to the cyanopyrrolidine core, e.g. the amine directly attached to the cyanopyrrolidine core, is via the aromatic ring of the bicycle. In particular examples, a bicyclic heteroaryl is one in which the entire fused ring system is aromatic. A bicyclic heteroaryl can have the at least one heteroatom in either of the fused rings. For example, a bicyclic ring with an aromatic ring fused to a partially saturated ring may contain the at least one heteroatom in the aromatic ring or the partially saturated ring. Attachment of the bicyclic ring to the group it is a substituent of may be via either a heteroatom containing ring or a carbon only containing ring. The point of attachment of heteroaryl to the group it is a substituent of can be via a carbon atom or a heteroatom (e.g. nitrogen). In instances where $R^2$ is a heteroaryl ring, attachment to the amide nitrogen attached to the cyanopyrrolidine core is via an aromatic ring, wherein the aromatic ring may be fused to a further aromatic or partially saturated ring. Examples for heteroaryl include pyridinyl, pyrazinyl, pyrimidinyl, pyridazinyl, furanyl, thiophenyl, pyrrolyl, oxazolyl, thiazolyl, pyrazolyl, triazolyl, tetrazolyl, indolyl, indolizinyl, isoindolyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, benzoxazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydropyridinyl, dihydropyrrolopyridinyl, quinoxalinyl, dihydrobenzoxazinyl, tetrahydropyridopyrazinyl, tetrahydroquinolinyl and tetrahydroisoquinolinyl. Unless specified otherwise, heteroaryl within the definitions of $R^h$, R', $R^i$, $R^j$, $R^2$, $R^3$ and $R^{13}$, may be unsubstituted or substituted with one or more of the substituents defined herein.

"Heterocyclyl" or "heterocyclic" as used herein in describing a ring means, unless otherwise stated, a monocyclic saturated or partially unsaturated, non-aromatic ring or a bicyclic saturated or partially unsaturated ring, wherein the bicyclic ring system is non-aromatic, the mono- or bicyclic ring having, for example, 3 to 10 members or 5 to 10 members, where at least one member and up to 5 members, particularly 1, 2 or 3 members of the ring are heteroatoms selected from N, O and S, and the remaining ring atoms are carbon atoms, in stable combinations known to those of skill in the art. Heterocyclic ring nitrogen and sulphur atoms are optionally oxidised, and the nitrogen atoms(s) are optionally quaternized. As used herein, the heterocyclic ring may be a fused ring to another ring system to form a bicycle, i.e. one or two of the heterocyclic ring carbons is common to an additional ring system. In instances where the heterocyclyl is a bicyclic ring, the second ring can be aromatic, e.g. a fused phenyl, pyridinyl, pyrazolyl, or the like. The bicyclic heterocyclyl can have at least one heteroatom in either of the fused rings. For example, a bicyclic ring with an aromatic ring fused to a partially saturated ring may contain the at least one heteroatom in the aromatic ring or the partially saturated ring. Attachment of the bicyclic ring to the group it is a substituent of may be via either a heteroatom containing ring or a carbon only containing ring. The point of attachment of heterocyclyl to the group it is a substituent of can be via the carbon atom or a heteroatom (e.g. nitrogen).

Attachment of the bicyclic ring to the group it is a substituent of, in relation to the pyrrolidine core, is from the non-aromatic ring. Examples of heterocyclyl groups include azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, dihydrobenzoxazinyl and tetrahydroisoquinolinyl. Unless specified otherwise, heterocyclyl within the definitions of $R^h$, R', $R^i$, $R^j$, $R^3$ and $R^{13}$, may be unsubstituted or substituted with one or more of the substituents defined herein.

"Optionally substituted" as applied to any group means that the said group may if desired be substituted with one or more substituents (e.g., 1, 2, 3 or 4 substituents) which may be the same or different.

Examples of suitable substituents for "substituted" and "optionally substituted" $C_1$-$C_6$ alkyl (including $C_1$-$C_4$ alkyl, $C_1$-$C_3$ alkyl and $C_1$-$C_2$ alkyl) and $C_1$-$C_6$ alkoxy (including $C_1$-$C_4$ alkoxy, $C_1$-$C_3$ alkoxy and $C_1$-$C_2$ alkoxy) and $C_2$-$C_6$ alkenyl (including $C_2$-$C_4$ alkenyl) and $C_2$-$C_6$ alkynyl (including $C_2$-$C_4$ alkynyl) within the definitions of $R^a$, $R^b$, $R^c$, $R^d$, $R^e$, $R^f$, $R^g$, $R^h$, R', $R^i$, $R^j$, $R^1$, $R^4$, $R^5$, $R^6$, $R^7$, $R^8$, $R^{10}$, $R^{11}$, $R^{12}$, $Q^{1a}$ and within the definition of substituents for $R^3$, and $C_1$-$C_6$ alkylene (including $C_1$-$C_3$ alkylene) and $C_2$-$C_6$ alkenylene within the definitions of $R^9$, $Q^{1b}$, $Q^{2a}$ and $Q^{2b}$, include $C_1$-$C_6$ alkoxy, halo, hydroxyl, thiol, cyano, amino and nitro, in particular, halo (preferably fluoro or chloro), hydroxyl and cyano.

Examples of suitable substituents for "substituted" and "optionally substituted" rings, i.e. cycloalkyl, heterocyclyl, aryl and heteroaryl rings, within the definitions of $R^a$, $R^b$, $R^e$, $R^f$, $R^g$, $R^h$, R', $R^i$, $R^j$, $R^2$, $R^3$ and $R^{13}$, include halo, cyano, oxo, nitro, amino, amide, hydroxy, $C_1$-$C_6$ alkyl or $C_1$-$C_3$ alkyl, $C_1$-$C_6$ alkoxy or $C_1$-$C_3$ alkoxy, aryl, heteroaryl, heterocyclyl, $C_3$-$C_6$ cycloalkyl, $C_1$-$C_3$ alkylamino, $C_2$-$C_6$ alkenylamino, di-$C_1$-$C_3$ alkylamino, $C_1$-$C_3$ acylamino, di-$C_1$-$C_3$ acylamino, carboxy, $C_1$-$C_3$ alkoxycarbonyl, carboxamidyl, mono-$C_1$-$C_3$ carbamoyl, di-$C_1$-$C_3$ carbamoyl or any of the above in which a hydrocarbyl moiety is itself substituted by halo, in particular fluoro, hydroxyl, cyano, amino and nitro. In groups containing an oxygen atom such as hydroxy and alkoxy, the oxygen atom can be replaced with sulphur to make groups such as thio (SH) and thio-alkyl (S-alkyl). Optional substituents therefore include groups such as S-methyl. In thio-alkyl groups, the sulphur atom may be further oxidised to make a sulfoxide or sulfone, and thus optional substituents therefore includes groups such as S(O)-alkyl and S(O)$_2$-alkyl.

Examples of suitable substituents for "substituted" and "optionally substituted" rings include in particular, halo, oxo, cyano, $C_1$-$C_3$ alkyl, $C_1$-$C_3$ alkoxy, heterocyclyl, cycloalkyl, heteroaryl or aryl, wherein the alkyl or alkoxy is optionally substituted with one or more (e.g. one, two or three) substituents selected from halo, hydroxyl, thiol, cyano, amino and nitro. In particular, suitable substituents for "substituted" and "optionally substituted" rings disclosed herein include fluoro, chloro, oxo, cyano, $C_1$-$C_3$ alkyl, $C_1$-$C_3$ alkoxy, wherein the alkyl or alkoxy is optionally substituted with one or more (e.g. one, two or three) substituents selected from halo, hydroxyl, thiol, cyano, amino and nitro, in particular, one or more fluoro.

Substituted groups thus include for example Br, Cl, F, CN, Me, Et, Pr, t-Bu, OMe, OEt, OPr, C(CH$_3$)$_3$, CH(CH$_3$)$_2$, CF$_3$, OCF$_3$, C(O)NHCH$_3$, cyclopropyl, phenyl. In the case of aryl groups, the substitutions may be in the form of rings from adjacent carbon atoms in the aryl ring, for example cyclic acetals such as O—CH$_2$—O.

Preferred embodiments of the compound of formula (I) for use in the present invention are defined below.

$R^a$ may represent hydrogen. $R^a$ may represent cyano. $R^a$ may represent $C_1$-$C_3$ alkyl. $R^a$ may represent $C_1$-$C_2$ alkyl (e.g. methyl or ethyl). $R^a$ may represent methyl or substituted methyl. In one embodiment, when $R^a$ is other than hydrogen, $R^b$, $R^c$, $R^d$, $R^e$, $R^f$, $R^g$, and $R^h$ or $R^i$ and $R^j$ if present, each represent hydrogen. The alkyl within the definition of $R^a$ may be unsubstituted or substituted with one or more substituents selected from $C_1$-$C_6$ alkoxy, halo, hydroxyl, thiol, cyano, amino, amido and nitro. In particular, the alkyl is optionally substituted with fluoro.

$R^b$ may represent hydrogen. $R^b$ may represent $C_1$-$C_3$ alkyl. $R^b$ may represent $C_1$-$C_2$ alkyl (e.g. methyl or ethyl). $R^b$ may represent methyl or substituted methyl. When $R^b$ represents $C_1$-$C_3$ alkyl and $R^a$, $R^c$, $R^d$, $R^e$, $R^f$, $R^g$, and $R^h$ or $R^i$ and $R^j$ if present, each represent hydrogen. The alkyl within the definition of $R^b$ may be unsubstituted or substituted with one or more substituents selected from $C_1$-$C_6$ alkoxy, halo, hydroxyl, thiol, cyano, amino, amido and nitro. In particular, the alkyl is optionally substituted with fluoro.

In one embodiment, when $R^b$ is other than hydrogen, $R^c$ is hydrogen. When $R^c$ is other than hydrogen, $R^b$ may be hydrogen, such that one of $R^b$ and $R^c$ is hydrogen.

In another embodiment, $R^b$ and $R^c$ may each represent methyl.

$R^d$ may represent hydrogen. $R^d$ may represent $C_1$-$C_3$ alkyl. $R^d$ may represent $C_1$-$C_2$ alkyl (e.g. methyl or ethyl). $R^d$ may represent methyl or substituted methyl. When $R^d$ represents $C_1$-$C_3$ alkyl and $R^a$, $R^b$, $R^c$, $R^e$, $R^f$, $R^g$, and $R^h$ or $R^i$ and $R^j$ if present, each represent hydrogen. The alkyl within the definition of $R^d$ may be unsubstituted or substituted with one or more substituents selected from $C_1$-$C_6$ alkoxy, halo, hydroxyl, thiol, cyano, amino, amido and nitro. In particular, the alkyl is optionally substituted with fluoro.

In one embodiment, when $R^d$ is other than hydrogen, $R^e$ is hydrogen. When $R^e$ is other than hydrogen, $R^d$ may be hydrogen, such that one of $R^d$ and $R^e$ is hydrogen.

In another embodiment, $R^d$ and $R^e$ may each represent methyl.

$R^f$ may represent hydrogen. $R^f$ may represent cyano. $R^f$ may represent $C_1$-$C_3$ alkyl. $R^f$ may represent $C_1$-$C_2$ alkyl (e.g. methyl or ethyl). $R^f$ may represent methyl or substituted methyl. When $R^g$ and $R^1$ together form the structure (IA) and X is C($R^i$)($R^j$), $R^f$ may represent fluoro. When $R^g$ and $R^1$ together form the structure (IA) and X is C($R^i$)($R^j$), $R^f$ may represent optionally substituted $C_1$-$C_3$ alkoxy (e.g. methoxy or ethyoxy). When $R^f$ is other than hydrogen, $R^a$, $R^b$, $R^c$, $R^g$ and $R^h$ or $R^i$ and $R^j$ if present, may each represent hydrogen. The alkyl within the definition of $R^f$ may be unsubstituted or substituted with one or more substituents selected from $C_1$-$C_6$ alkoxy, halo, hydroxyl, thiol, cyano, amino, amido and nitro. In particular, the alkyl is optionally substituted with fluoro.

In one embodiment, when $R^f$ is other than hydrogen, $R^g$ is hydrogen. When $R^g$ is other than hydrogen, $R^f$ may be hydrogen, such that one of $R^f$ and $R^g$ is hydrogen.

In another embodiment, $R^f$ and $R^g$ may each represent fluoro. Alternatively, $R^f$ and $R^g$ may each represent methyl.

In one embodiment, $R^1$ is selected from hydrogen and optionally substituted $C_1$-$C_3$ alkyl.

In another embodiment, $R^1$ is linked to $R^g$ to form the structure (IA):

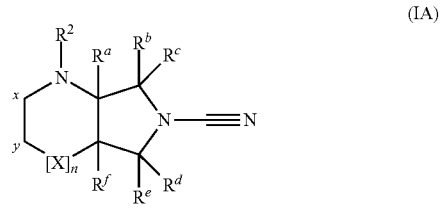

The substituents at position x may be selected from cyano, an optionally substituted $C_1$-$C_3$ alkyl or an optionally substituted 3 to 6-membered heterocyclyl, cycloalkyl, aryl or heteroaryl ring. The substituents at position y may be selected from halo, cyano, an optionally substituted $C_1$-$C_3$ alkyl, an optionally substituted $C_1$-$C_3$ alkoxy, or an optionally substituted 3 to 6-membered heterocyclyl, cycloalkyl, aryl or heteroaryl ring, with the proviso that position y cannot be substituted with halo or optionally substituted $C_1$-$C_3$ alkoxy when X is O or N($R^h$). Alternatively, positions x and y may be substituted so as to form together a fused 3 to 6-membered heterocyclyl, cycloalkyl, heteroaryl or aryl ring which may be optionally substituted.

The optional alkyl and alkoxy substituents at positions x and/or y may be unsubstituted or substituted with one or more substituents selected from $C_1$-$C_6$ alkoxy, halo, hydroxyl, thiol, cyano, amino and nitro, wherein the alkyl and alkoxy may be optionally substituted with halo. The 3 to 6-membered rings may be unsubstituted or substituted with a substituent selected from halo, cyano, oxo, nitro, amino, amido, hydroxyl, $C_1$-$C_6$ alkyl or $C_1$-$C_3$ alkyl, $C_1$-$C_6$ alkoxy or $C_1$-$C_3$ alkoxy, wherein the alkyl and alkoxy may be optionally substituted with halo.

In one embodiment, the structure (IA) is unsubstituted at positions x and y.

When X represents N($R^h$), $R^h$ represents hydrogen, C(O)R', optionally substituted $C_1$-$C_3$ alkyl or an optionally substituted 3 to 6-membered ring. The 3 to 6-membered ring may be a cycloalkyl, aryl, heterocyclyl or heteroaryl ring. $R^h$ may represent hydrogen. $R^h$ may represent C(O)R'. $R^h$ may represent $C_1$-$C_3$ alkyl. $R^h$ may represent $C_1$-$C_2$ alkyl (e.g. methyl or ethyl). $R^h$ may represent methyl or substituted methyl. $R^h$ may represent a 3 to 6-membered heterocyclyl, cycloalkyl, heteroaryl or aryl ring. When $R^h$ is other than hydrogen, $R^a$, $R^b$, $R^c$, $R^d$, $R^e$, $R^f$ and $R^g$ may each represent hydrogen. In particular, $R^h$ may represent $C_1$-$C_3$ alkyl or a 5 or 6-membered aryl or heteroaryl ring. The alkyl within the definition of $R^h$ may be unsubstituted or substituted with one or more substituents selected from $C_1$-$C_6$ alkoxy, halo, hydroxyl, thiol, cyano, amino, amido and nitro, wherein the alkyl and alkoxy may be optionally substituted with halo.

R' represents an optionally substituted $C_1$-$C_3$ alkyl or an optionally substituted 3 to 10-membered monocyclic or bicyclic heteroaryl, aryl, heterocyclyl or cycloalkyl ring. R' may represent $C_1$-$C_3$ alkyl. R' may represent $C_1$-$C_2$ alkyl (e.g. methyl or ethyl). R' may represent a 3 to 6-membered heteroaryl, aryl, heterocyclyl or cycloalkyl ring. The heteroaryl, aryl, heterocyclyl or cycloalkyl ring may be unsubstituted or substituted. The alkyl within the definition of R' may be unsubstituted or substituted with one or more substituents selected from $C_1$-$C_6$ alkoxy, halo, hydroxyl, thiol, cyano, amino and nitro, wherein the alkyl and alkoxy may be optionally substituted with halo.

When X represents C(R$^i$)(R$^j$), R$^i$ and R$^j$ each independently represent hydrogen, fluoro, cyano, an optionally substituted C$_1$-C$_3$ alkyl, an optionally substituted C$_1$-C$_3$ alkoxy, or an optionally substituted 3 to 6-membered ring. R$^i$ may represent hydrogen. R$^i$ may represent fluoro. R$^i$ may represent cyano. R$^i$ may represent C$_1$-C$_3$ alkyl. R$^i$ may represent C$_1$-C$_2$ alkyl (e.g. methyl or ethyl). R$^i$ may represent methyl or substituted methyl. R$^i$ may represent C$_1$-C$_3$ alkoxy. R$^i$ may represent C$_1$-C$_2$ alkoxy (e.g. methoxy or ethoxy). R$^i$ may represent methoxy or substituted methoxy. R$^i$ may represent a 3 to 6-membered heterocyclyl, cycloalkyl, heteroaryl or aryl ring. The alkyl and alkoxy within the definition of R$^i$ and R$^j$ may be unsubstituted or substituted with one or more substituents selected from C$_1$-C$_6$ alkoxy, halo, hydroxyl, thiol, cyano, amino and nitro, wherein the alkyl and alkoxy may be optionally substituted with halo.

In one embodiment, when R$^i$ is other than hydrogen, R$^j$ is hydrogen. When R$^j$ is other than hydrogen, R$^i$ may be hydrogen, such that one of R$^i$ and R$^j$ is hydrogen.

Alternatively, R$^b$ and R$^c$ may together form a spirocyclic ring. In addition, or alternatively, R$^d$ and R$^e$ may together form a spirocyclic ring. In addition, or alternatively, R$^f$ and R$^g$ may together form a spirocyclic ring. In such instances, preferably only one of R$^b$/R$^c$, R$^d$/R$^e$ and R$^f$/R$^g$ form a spirocyclic ring, wherein the remaining groups may each represent hydrogen. The spirocyclic ring can contain 3, 4, 5 or 6 carbon ring atoms, in particular 3 or 4 carbon ring atoms. The spirocyclic ring shares one ring atom with the cyanopyrrolidine core. The spirocyclic ring may be unsubstituted or substituted with a substituent selected from halo, cyano, oxo, nitro, amino, amido, hydroxyl, C$_1$-C$_6$ alkyl or C$_1$-C$_3$ alkyl, C$_1$-C$_6$ alkoxy or C$_1$-C$_3$ alkoxy, wherein the alkyl and alkoxy may be optionally substituted with halo.

Neighbouring R groups attached to the carbon ring atoms of the cyanopyrrolidine core may together form an optionally substituted C$_3$-C$_4$ cycloalkyl ring. For example, R$^a$ together with R$^b$ or R$^g$, and R$^e$ together with R$^f$. In such instances, preferably one cycloalkyl group is present whilst the remaining R groups each represent hydrogen. The C$_3$-C$_4$ cycloalkyl ring may be unsubstituted or substituted with a substituent selected from halo, cyano, oxo, nitro, amino, amido, hydroxyl, C$_1$-C$_6$ alkyl or C$_1$-C$_3$ alkyl, C$_1$-C$_6$ alkoxy or C$_1$-C$_3$ alkoxy, wherein the alkyl and alkoxy may be optionally substituted with halo.

One of R$^a$, R$^b$, R$^c$, R$^d$, R$^e$, R$^f$, and R$^g$ or R$^h$ or R$^i$ and R$^j$ if present, may be other than hydrogen and the remaining each represent hydrogen.

Two of R$^a$, R$^b$, R$^c$, R$^d$, R$^e$, R$^f$, and R$^g$ or R$^h$ or R$^i$ and R$^j$ if present, may be other than hydrogen and the remaining each represent hydrogen.

Three of R$^a$, R$^b$, R$^c$, R$^d$, R$^e$, R$^f$, and R$^g$ or R$^h$ or R$^i$ and R$^j$ if present, may be other than hydrogen and the remaining each represent hydrogen.

Four of R$^a$, R$^b$, R$^c$, R$^d$, R$^e$, R$^f$, and R$^g$ or R$^h$ or R$^i$ and R$^j$ if present, may be other than hydrogen and the remaining each represent hydrogen.

Five of R$^a$, R$^b$, R$^c$, R$^d$, R$^e$, R$^f$, and R$^g$ or R$^h$ or R$^i$ and R$^j$ if present, may be other than hydrogen and the remaining each represent hydrogen.

Six of R$^a$, R$^b$, R$^c$, R$^d$, R$^e$, R$^f$, and R$^g$ or R$^h$ or R$^i$ and R$^j$ if present, may be other than hydrogen and the remaining each represent hydrogen.

When one, two, three, four, five or six of R$^a$, R$^b$, R$^c$, R$^d$, R$^e$, R$^f$, and R$^g$ or R$^h$ or R$^i$ and R$^j$ if present, are other than hydrogen, the other R groups represent a group in accordance with the definitions above. In particular, one, two, three or four of R$^a$, R$^b$, R$^c$, R$^d$, R$^e$, R$^f$, and R$^g$ or R$^h$ or R$^i$ and R$^j$ if present, are other than hydrogen and the remaining each represent hydrogen. More particularly, one or two of R$^a$, R$^b$, R$^c$, R$^d$, R$^e$, R$^f$, and R$^g$ or R$^h$ or R$^i$ and R$^j$ if present, are other than hydrogen and the remaining each represent hydrogen.

In one embodiment, R$^a$, R$^b$, R$^c$, R$^d$, R$^e$, R$^f$, and R$^g$ or R$^h$ or R$^i$, and R$^j$, if present, each represent hydrogen.

In another embodiment, R$^1$ is linked to R$^g$ to form the structure (IA), wherein the 5 or 6-membered ring may be optionally further substituted. In such cases the compounds may be of the formula (II)

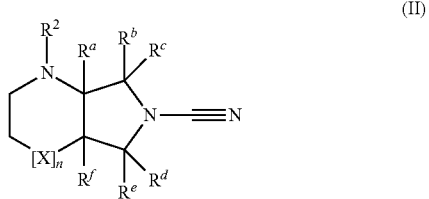

(II)

a tautomer thereof, or a pharmaceutically acceptable salt of said compound or tautomer, wherein:

n is 0 or 1;

X is selected from O, N(R$^h$), C(R$^i$)(R$^j$);

R$^a$ is selected from hydrogen, cyano, and optionally substituted C$_1$-C$_3$ alkyl; or R$^a$ is linked to R$^g$ or R$^b$ to form an optionally substituted C$_3$-C$_4$ cycloalkyl ring;

R$^b$, R$^c$, R$^d$ and R$^e$ are each independently selected from hydrogen, optionally substituted C$_1$-C$_3$ alkyl, and one or more spirocyclic groups where R$^b$ is linked to R$^c$, or R$^d$ is linked to R$^e$; or R$^b$ is linked to R$^a$ to form an optionally substituted C$_3$-C$_4$ cycloalkyl, or R$^e$ is linked to R$^f$ to form an optionally substituted C$_3$-C$_4$ cycloalkyl;

R$^f$ is selected from hydrogen, fluoro, cyano, optionally substituted C$_1$-C$_3$ alkyl, optionally substituted C$_1$-C$_3$ alkoxy;

when X is O or N(R$^h$), R$^f$ is not fluoro or optionally substituted C$_1$-C$_3$ alkoxy;

R$^h$ is selected from hydrogen, C(O)R', optionally substituted C$_1$-C$_3$ alkyl, and optionally substituted 3 to 6-membered heterocyclyl, cycloalkyl, heteroaryl or aryl ring;

R' is selected from optionally substituted C$_1$-C$_3$ alkyl, and optionally substituted 3 to 10-membered monocyclic or bicyclic heteroaryl, aryl, heterocyclyl or cycloalkyl ring;

R$^i$ and R$^j$ are each independently selected from hydrogen, fluoro, cyano, optionally substituted C$_1$-C$_3$ alkyl, optionally substituted C$_1$-C$_3$ alkoxy, and optionally substituted 3 to 6-membered heterocyclyl, cycloalkyl, heteroaryl or aryl ring;

R$^2$ is a 5 to 10-membered, monocyclic or bicyclic, heteroaryl or aryl ring, which may be unsubstituted, or substituted with one or more Q$^1$(R$^3$)$_m$ groups, which may be the same or different.

When n is 1 and X represents C(R$^i$)(R$^j$), the compounds may be of the formula (IIA):

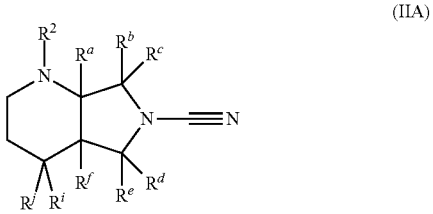

(IIA)

a tautomer thereof, or a pharmaceutically acceptable salt of said compound or tautomer, wherein: $R^a$, $R^b$, $R^c$, $R^d$, $R^e$, $R^f$, $R^i$, $R^j$, and $R^2$, are as defined herein.

When n is 1 and X represents O, the compounds may be of the formula (IIB):

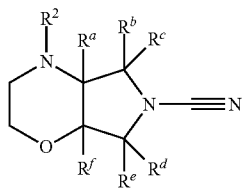

(IIB)

a tautomer thereof, or a pharmaceutically acceptable salt of said compound or tautomer, wherein: $R^a$, $R^b$, $R^c$, $R^d$, $R^e$, $R^f$, and $R^2$, are as defined herein.

When n is 0, X is absent, and the compounds may be of the formula (ITC):

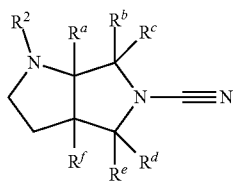

(IIC)

a tautomer thereof, or a pharmaceutically acceptable salt of said compound or tautomer, wherein: $R^a$, $R^b$, $R^c$, $R^d$, $R^e$, $R^f$, and $R^2$, are as defined herein.

When n is 1 and X represents $N(R^h)$, the compounds may be of the formula (IID):

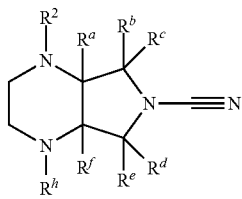

(IID)

a tautomer thereof, or a pharmaceutically acceptable salt of said compound or tautomer, wherein: $R^a$, $R^b$, $R^c$, $R^d$, $R^e$, $R^f$, $R^h$, and $R^2$, are as defined herein.

$R^2$ may represent a 5 to 10-membered heteroaryl or heterocyclyl ring substituted with one or more (e.g. one, two, three or four) of $Q^1(R^3)_m$, in particular one or two of $Q^1(R^3)_m$.

In particular, $R^2$ may represent a 5 or 6-membered heteroaryl or heterocyclyl ring which is substituted with one or more (e.g. one, two, three or four) of $Q^1(R^3)_m$.

Alternatively, $R^2$ may represent a 9 or 10-membered bicyclic heteroaryl or heterocyclyl ring which is substituted with one or more (e.g. one, two, three or four) of $Q^1(R^3)_m$.

In certain instances, $R^2$ may represent a 5 or 6-membered monocyclic heteroaryl or aryl ring optionally substituted with a $Q^1(R^3)_m$ moiety, wherein m is 1 or $R^2$ represents a 9 or 10-membered bicyclic heteroaryl or aryl ring optionally substituted with a $Q^1(R^3)_m$ moiety wherein m is 0. $Q^1$ and $R^3$ are as defined herein.

In certain instances, $R^2$ may represent a 5 or 6-membered monocyclic heteroaryl or aryl ring optionally substituted with only one $Q^1(R^3)_m$ moiety, wherein m is 1 or $R^2$ represents a 9 or 10-membered bicyclic heteroaryl or aryl ring optionally substituted with only one $Q^1(R^3)_m$ moiety wherein m is 0. $Q^1$ and $R^3$ are as defined herein.

$R^2$ may comprises one or more (e.g. 1, 2, 3 or 4) heteroatoms independently selected from nitrogen, oxygen and sulphur. In particular, $R^2$ contains at least one nitrogen atom, for example, 1, 2 or 3 nitrogen atoms, preferably 1 or 2 nitrogen heteroatoms.

$R^2$ may be selected from the group consisting of azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, tetrahydroisoquinolinyl, pyridinyl, pyrazinyl, pyrimidinyl, pyridazinyl, furanyl, thiophenyl, pyrrolyl, oxazolyl, thiazolyl, pyrazolyl, triazolyl, tetrazolyl, indolyl, indolizinyl, isoindolyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, benzoxazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydropyridinyl, dihydropyrrolopyridinyl, quinoxalinyl, dihydrobenzoxazinyl, tetrahydropyridopyrazinyl, tetrahydropyridopyrazinyl, tetrahydroquinolinyl and tetrahydroisoquinolinyl.

In particular, $R^2$ is selected from thiazolyl, phenyl, pyridinyl, benzothiazolyl, pyrimidinyl, pyridazinyl, pyrazinyl, and benzimidazolyl; and may be optionally substituted.

Examples of $R^2$ include those shown below:

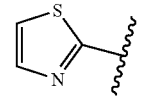

A

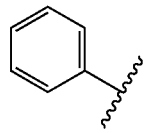

B

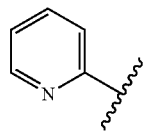

C

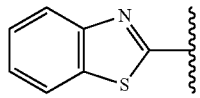

D

-continued

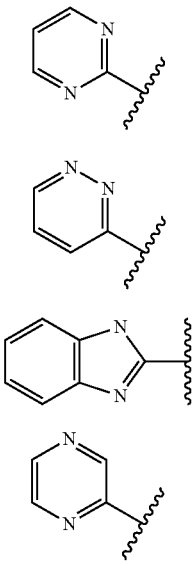

wherein

represents the point of attachment to the nitrogen attached to the cyanopyrrolidine, and wherein $R^2$ may be optionally substituted as defined herein.

In one embodiment, when $R^1$ is linked to $R^g$, $R^2$ cannot be pyrazolopyridinyl or pyrimidopyrimidinyl.

$R^2$ may be substituted with one or more $Q^1(R^3)_m$, wherein each occurrence of $Q^1(R^3)_m$ may be the same or different, wherein:

m is 0 or 1;

$Q^1$ represents $Q^{1a}$ or $Q^{1b}$ (i.e. when m is 0, $Q^1$ is $Q^{1a}$ and when m is 0, $Q^1$ is $Q^{1b}$); wherein $Q^{1a}$ is selected from oxo, halo, cyano, nitro, hydroxyl, $SR^6$, $NR^6R^7$, $CONR^6R^7$, $C_0$-$C_3$-alkylene-$NR^6COR^7$, $NR^6CONR^7R^8$, $COR^6$, $C(O)OR^6$, $SO_2R^6$, $SO_2NR^6R^7$, $NR^6SO_2R^7$, $NR^6SO_2NR^7R^8$, $NR^6C(O)OR^7$, optionally substituted $C_1$-$C_6$ alkyl, optionally substituted $C_1$-$C_6$ alkoxy, optionally substituted $C_2$-$C_6$ alkenyl;

$Q^{1b}$ is selected from a covalent bond, an oxygen atom, a sulphur atom, $OR^9$, SO, $SO_2$, CO, C(O)O, $C_0$-$C_3$-alkylene-C(O)$NR^6$—$C_0$-$C_3$ alkylene, $C_0$-$C_3$-alkylene-$NR^6$—$C_0$-$C_3$ alkylene, $C_0$-$C_3$-alkylene-$NR^6C(O)$—$C_0$-$C_3$ alkylene, $NR^6CONR^7$, $SO_2NR^6$, $NR^6SO_2$, $NR^6SO_2NR^7$, $NR^6C(O)O$, $NR^6C(O)OR^9$, optionally substituted $C_1$-$C_6$ alkylene, or optionally substituted $C_2$-$C_6$ alkenylene;

$R^3$ represents an optionally substituted 3 to 10-membered monocyclic or bicyclic heterocyclyl, heteroaryl, cycloalkyl or aryl ring;

$R^6$, $R^7$ and $R^8$ each independently represent hydrogen or optionally substituted $C_1$-$C_6$ alkyl;

$R^9$ represents optionally substituted $C_1$-$C_6$ alkylene;

with the proviso that $R^2$ is not substituted with $C(O)NH_2$ when $R^1$ is hydrogen or optionally substituted $C_1$-$C_3$ alkyl.

$R^2$ may optionally be substituted with one, two, three or four of $Q^1(R^3)_m$. For example, $R^2$ may be substituted with one, two or three of $Q^1(R^3)_m$. In particular, $R^2$ is substituted with one or two of $Q^1(R^3)_m$. Each occurrence of $Q^1(R^3)_m$ may be the same or different. More particularly, $R^2$ is substituted with one of $Q^1(R^3)_m$. $Q^1$, $R^3$ and n are as defined herein.

In particular, $Q^{1a}$ may be selected from oxo, halo (e.g. fluoro, chloro or bromo), cyano, nitro, hydroxyl, $SR^6$ (e.g. thiol), $NR^6R^7$ (e.g. N,N-dimethylamino), $CONR^6R^7$, $C_0$-$C_3$-alkylene-$NR^6COR^7$ (e.g. N-acetyl), $NR^6CONR^7R^8$, $COR^6$ (e.g. acetyl), $C(O)OR^6$ (e.g. methoxycarbonyl or ethoxycarbonyl), $SO_2R^6$ (e.g. methyl sulphonyl), $SO_2NR^6R^7$ (e.g. dimethylaminosulphonyl), $NR^6SO_2R^7$, $NR^6SO_2NR^7R^8$, $NR^6C(O)OR^7$, optionally substituted $C_1$-$C_4$ alkyl (e.g. propyl, isobutyl or tert-butyl), optionally substituted $C_1$-$C_2$ alkyl (e.g. methyl, ethyl or $CF_3$) optionally substituted $C_1$-$C_6$ alkoxy (e.g. methoxy, ethoxy or $OCF_3$) and optionally substituted $C_2$-$C_6$ alkenyl. The alkyl, alkoxy, alkenyl may be unsubstituted or substituted with one or more substituents selected from $C_1$-$C_6$ alkoxy, halo, hydroxyl, thiol, cyano, amino and nitro.

More particularly, $Q^{1a}$ may be selected from halo, cyano, optionally substituted $C_1$-$C_3$ alkyl or optionally substituted $C_1$-$C_3$ alkoxy. Even more particularly, $Q^{1a}$ may be selected from halo, cyano, $OCH_3$, $CF_3$ and $OCF_3$.

$Q^{1b}$ may be selected from a covalent bond, an oxygen atom, a sulphur atom, $OR^9$, SO, $SO_2$, CO, C(O)O, $C_0$-$C_3$-alkylene-C(O)$NR^6$—$C_0$-$C_3$ alkylene, $C_0$-$C_3$-alkylene-$NR^6$—$C_0$-$C_3$ alkylene, $C_0$-$C_3$ alkylene $NR^6C(O)$—$C_0$-$C_3$ alkylene, $NR^6CONR^7$, $SO_2NR^6$, $NR^6SO_2$, $NR^6SO_2NR^7$, $NR^6C(O)O$, $NR^6C(O)OR^9$, optionally substituted $C_1$-$C_6$ alkylene, or optionally substituted $C_2$-$C_6$ alkenylene, with the proviso that $Q^{1b}$ is not NH when $R^1$ is a nitrogen containing heteroaryl ring. The alkylene or alkenylene may be optionally substituted with one or more substituents selected from $C_1$-$C_6$ alkoxy, halo, hydroxyl, thiol, cyano, amino and nitro.

In particular, $Q^{1b}$ is a covalent bond.

$R^3$ may be selected from cyclopropyl, cyclobutyl, cyclopentyl, cyclohexyl, cycloheptyl, cyclooctyl, decahydronaphthalenyl, pyridinyl, pyrazinyl, pyrimidinyl, pyridazinyl, furanyl, thiophenyl, pyrrolyl, oxazolyl, thiazolyl, pyrazolyl, triazolyl, tetrazolyl, indolyl, indolizinyl, isoindolyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, benzoxazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydropyridinyl, dihydropyrrolopyridinyl, quinoxalinyl, dihydrobenzoxazinyl, tetrahydropyridopyrazinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl and tetrahydroisoquinolinyl.

$R^3$ may represent an optionally substituted 5 or 6-membered heterocyclyl, cycloalkyl or aryl ring.

Alternatively, $R^3$ may represent an optionally substituted 9 or 10-membered bicyclic heterocyclyl, cycloalkyl, heteroaryl or aryl ring.

In particular, $R^3$ is selected from substituted or unsubstituted phenyl and pyridinyl.

In all cases described herein, $R^3$ may be optionally substituted with one or more substituents independently selected from halo, cyano, oxo, nitro, hydroxyl, $SR^{10}$, optionally substituted $C_1$-$C_6$ alkyl, optionally substituted $C_1$-$C_6$ alkoxy, optionally substituted $C_2$-$C_6$ alkenyl, optionally substituted $C_2$-$C_6$ alkynyl, $Q^{2a}$-$R^{13}$, $Q^{2a}$-O-$Q^{2b}$-$R^{13}$, $Q^{2a}$-S-$Q^{2b}$-$R^{13}$, $Q^{2a}$-SO-$Q^{2b}$-$R^{13}$, $Q^{2a}$-$NR^{10}CONR^{11}R^{12}$, $Q^{2a}$-$NR^{10}CONR^{11}$-$Q^{2a}$-$R^{13}$, $Q^{2a}$-$NR^{10}R^{11}$, $Q^{2a}$-$NR^{10}$-$Q^{2b}$-$R^{13}$, $Q^{2a}$-$COR^{10}$, $Q^{2a}$-CO-$Q^{2b}$-$R^{13}$, $Q^{2a}$-$NR^{10}COR^{11}$, $Q^{2a}$-$NR^{10}$CO-$Q^{2b}$-$R^{13}$, $Q^{2a}$-$NR^{10}C(O)OR^{11}$, $Q^{2a}$-$NR^{10}C(O)O$-$Q^{2b}$-$R^{13}$, $Q^{2a}$-$SO_2R^{10}$, $Q^{2a}$-$SO_2$-$Q^{2b}$-$R^{13}$, $Q^{2a}$-$CONR^{10}R^{11}$, $Q^{2a}$-$CONR^{10}CO$-$Q^{2b}$-$R^{13}$, $Q^{2a}$-$CO_2R^{10}$, $Q^{2a}$-$CO_2$-$Q^{2b}$-$R^{13}$, $Q^{2a}$-$SO_2NR^{10}R^{11}$, $Q^{2a}$-$SO_2NR^{10}$-$Q^{2b}$-$R^{13}$, $Q^{2a}$-$NR^{10}SO_2R^{11}$, $Q^{2a}$-$NR^{10}SO_2$-$Q^{2b}$-$R^{13}$ and $Q^{2a}$-$NR^{10}SO_2NR^{11}R^{12}$, $Q^{2a}$-$NR^{10}SO_2NR^{11}$-$Q^{2b}$-$R^{13}$;

wherein $Q^{2a}$ and $Q^{2b}$ each independently represent a covalent bond, optionally substituted $C_1$-$C_6$ alkylene or optionally substituted $C_2$-$C_6$ alkenylene;

$R^{10}$, $R^{11}$ and $R^{12}$ each independently represent hydrogen or optionally substituted $C_1$-$C_6$ alkyl;

and $R^{13}$ represents optionally substituted heterocyclyl, optionally substituted heteroaryl, optionally substituted aryl, or an optionally substituted cycloalkyl.

In particular, $R^{13}$ represents a $C_3$-$C_4$ cycloalkyl ring which may be unsubstituted or substituted with a substituent selected from halo, cyano, oxo, nitro, amino, amido, hydroxyl, $C_1$-$C_6$ alkyl or $C_1$-$C_3$ alkyl, $C_1$-$C_6$ alkoxy or $C_1$-$C_3$ alkoxy, wherein the alkyl and alkoxy may be optionally substituted with halo.

$R^3$ may be substituted with one or more (e.g. one, two, three or four), in particular one or two substituents independently selected from halo, cyano, oxo, nitro, hydroxyl, Se, optionally substituted $C_1$-$C_6$ alkyl, optionally substituted $C_1$-$C_6$ alkoxy, optionally substituted $C_2$-$C_6$ alkenyl, optionally substituted $C_2$-$C_6$ alkynyl, $Q^{2a}$-$NR^{10}CONR^{11}R^{12}$, $Q^{2a}$-$NR^{10}CONR^{11}R^{12}$, $Q^{2a}$-$NR^{10}R^{11}$, $Q^{2a}$-$COR^{10}$, $Q^{2a}$-$NR^{10}COR^1$, $Q^{2a}$-$NR^{10}C(O)OR^{11}$, $Q^{2a}$-$SO_2R^{10}$, $Q^{2a}$-$CONR^{10}R^{11}$, $Q^{2a}$-$CO_2R^{10}$, $Q^{2a}$-$SO_2NR^{10}R^{11}$, $Q^{2a}$-$NR^{10}SO_2R^{11}$ and $Q^{2a}$-$NR^{10}SO_2NR^{11}R^{12}$;

wherein $Q^{2a}$ represents a covalent bond, optionally substituted $C_1$-$C_6$ alkylene or optionally substituted $C_2$-$C_6$ alkenylene;

$R^{10}$, $R^{11}$ and $R^{12}$ each independently represent hydrogen or optionally substituted $C_1$-$C_6$ alkyl.

$R^3$ may be unsubstituted, mono substituted or di-substituted.

In certain instances, $R^3$ represents a 3 to 10-membered heterocyclyl, cycloalkyl, heteroaryl or aryl ring selected from cyclopropyl, cyclobutyl, cyclopentyl, cyclohexyl, cycloheptyl, cyclooctyl, decahydronaphthalenyl, phenyl, naphthyl, naphthalenyl, pyridinyl, pyrazinyl, pyrimidinyl, pyridazinyl, furanyl, thiophenyl, pyrrolyl, oxazolyl, thiazolyl, pyrazolyl, triazolyl, tetrazolyl, indolyl, indolizinyl, isoindolyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, benzoxazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydropyridinyl, dihydropyrrolopyridinyl, quinoxalinyl, dihydrobenzoxazinyl, tetrahydropyridopyrazinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl and tetrahydroisoquinolinyl which is either unsubstituted or substituted with one or more (e.g. one, two or three) substituents selected from halo, cyano, oxo, nitro, hydroxyl, Se, optionally substituted $C_1$-$C_6$ alkyl, optionally substituted $C_1$-$C_6$ alkoxy, optionally substituted $C_2$-$C_6$ alkenyl, optionally substituted $C_2$-$C_6$ alkynyl, $Q^{2a}$-$R^{13}$, $Q^{2a}$-O-$Q^{2b}$-$R^{13}$, $Q^{2a}$-S-$Q^{2b}$-$R^{13}$, $Q^{2a}$-SO-$Q^{2b}$-$R^{13}$, $Q^{2a}$-$NR^{10}CONR^{11}R^{12}$, $Q^{2a}$-$NR^{10}CONR^{11}$-$Q^{2a}$-$R^{13}$, $Q^{2a}$-$NR^{10}$-$Q^{2b}$-$R^{13}$, $Q^{2a}$-$COR^{10}$, $Q^{2a}$-CO-$Q^{2b}$-$R^{13}$, $Q^{2a}$-$NR^{10}COR^{11}$, $Q^{2a}$-$NR^{10}CO$-$Q^{2b}$-$R^{13}$, $Q^{2a}$-$NR^{10}C(O)OR^{11}$, $Q^{2a}$-$NR^{10}C(O)O$-$Q^{2b}$-$R^{13}$, $Q^{2a}$-$SO_2R^{10}$, $Q^{2a}$-$SO_2$-$Q^{2b}$-$R^{13}$, $Q^{2a}$-$CONR^{10}R^{11}$, $Q^{2a}$-$CONR^{10}$-$Q^{2b}$-$R^{13}$, $Q^{2a}$-$CO_2R^{10}$, $Q^{2a}$-$CO_2$-$Q^{2b}$-$R^{13}$, $Q^{2a}$-$SO_2NR^{10}R^{11}$, $Q^{2a}$-$SO_2NR^{10}$-$Q^{2b}$-$R^{13}$, $Q^{2a}$-$NR^{10}SO_2R^{11}$, $Q^{2a}$-$NR^{10}SO_2$-$Q^{2b}$-$R^{13}$ and $Q^{2a}$-$NR^{10}SO_2NR^{11}R^{12}$, $Q^{2a}$-$NR^{10}SO_2NR^{11}$-$Q^{2b}$-$R^{13}$;

wherein $Q^{2a}$ and $Q^{2b}$ each independently represent a covalent bond, optionally substituted $C_1$-$C_6$ alkylene or optionally substituted $C_2$-$C_6$ alkenylene;

$R^{10}$, $R^{11}$ and $R^{12}$ each independently represent hydrogen or optionally substituted $C_1$-$C_6$ alkyl;

and $R^{13}$ represents optionally substituted heterocyclyl, optionally substituted heteroaryl, optionally substituted aryl, or an optionally substituted cycloalkyl.

$R^3$ may represent phenyl or pyridinyl, wherein the ring is unsubstituted or substituted with one or more, in particular, one or two, substituents selected from halo, cyano, oxo, nitro, hydroxyl, $SR^{10}$, optionally substituted $C_1$-$C_6$ alkyl, optionally substituted $C_1$-$C_6$ alkoxy, optionally substituted $C_2$-$C_6$ alkenyl, optionally substituted $C_2$-$C_6$ alkynyl, $Q^{2a}$-$R^{13}$, $Q^{2a}$-O-$Q^{2b}$-$R^{13}$, $Q^{2a}$-S-$Q^{2b}$-$R^{13}$, $Q^{2a}$-SO-$Q^{2b}$-$R^{13}$, $Q^{2a}$-$NR^{10}CONR^{11}R^{12}$, $Q^{2a}$-$NR^{10}CONR^{11}$-$Q^{2a}$-$R^{13}$, $Q^{2a}$-$NR^{10}$-$Q^{2b}$-$R^{13}$, $Q^{2a}$-$COR^{10}$, $Q^{2a}$-CO-$Q^{2b}$-$R^{13}$, $Q^{2a}$-$NR^{10}COR^{11}$, $Q^{2a}$-$NR^{10}CO$-$Q^{2b}$-$R^{13}$, $Q^{2a}$-$NR^{10}C(O)OR^{11}$, $Q^{2a}$-$NR^{10}C(O)O$-$Q^{2b}$-$R^{13}$, $Q^{2a}$-$SO_2R^{10}$, $Q^{2a}$-$SO_2$-$Q^{2b}$-$R^{13}$, $Q^{2a}$-$NR^{10}R^{11}$, $Q^{2a}$-$CONR^{10}$-$Q^{2b}$-$R^{13}$, $Q^{2a}$-$CO_2R^{10}$, $Q^{2a}$-$CO_2$-$Q^{2b}$-$R^{13}$, $Q^{2a}$-$SO_2NR^{10}R^{11}$, $Q^{2a}$-$SO_2NR^{10}$-$Q^{2b}$-$R^{13}$, $Q^{2a}$-$NR^{10}SO_2R^{11}$, $Q^{2a}$-$NR^{10}SO_2$-$Q^{2b}$-$R^{13}$ and $Q^{2a}$-$NR^{10}SO_2NR^{11}R^{12}$, $Q^{2a}$-$NR^{10}SO_2NR^{11}$-$Q^{2b}$-$R^{13}$;

wherein $Q^{2a}$ and $Q^{2b}$ each independently represent a covalent bond, optionally substituted $C_1$-$C_6$ alkylene or optionally substituted $C_2$-$C_6$ alkenylene;

$R^{10}$, $R^{11}$ and $R^{12}$ each independently represent hydrogen or optionally substituted $C_1$-$C_6$ alkyl;

and $R^{13}$ represents optionally substituted heterocyclyl, optionally substituted heteroaryl, optionally substituted aryl, or an optionally substituted cycloalkyl.

$R^3$ may represent phenyl or pyridinyl, wherein the phenyl ring is unsubstituted or substituted with one or more, in particular one or two, substituents selected from halo, cyano, oxo, nitro, hydroxyl, $SR^{10}$, optionally substituted $C_1$-$C_6$ alkyl, optionally substituted $C_1$-$C_6$ alkoxy, optionally substituted $C_2$-$C_6$ alkenyl, optionally substituted $C_2$-$C_6$ alkynyl, $Q^{2a}$-$NR^{10}CONR^{11}R^{12}$, $Q^{2a}$-$COR^{10}$, $Q^{2a}$-$NR^{10}COR^{11}$, $Q^{2a}$-$NR^{10}C(O)OR^{11}$, $Q^{2a}$-$SO_2R^{10}$, $Q^{2a}$-$CONR^{10}R^{11}$, $Q^{2a}$-$CO_2R^{10}$, $SO_2NR^{10}R^{11}$, $Q^{2a}$-$NR^{10}SO_2R^{11}$ and $Q^{2a}$-$NR^{10}SO_2NR^{11}R^{12}$;

wherein $Q^{2a}$ represents a covalent bond, optionally substituted $C_1$-$C_6$ alkylene or optionally substituted $C_2$-$C_6$ alkenylene;

$R^{10}$, $R^{11}$ and $R^{12}$ each independently represent hydrogen or optionally substituted $C_1$-$C_6$ alkyl.

According to a preferred embodiment, the present invention provides a compound of formula (I)

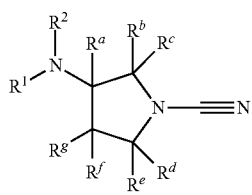

(I)

a tautomer thereof, or a pharmaceutically acceptable salt of said compound or tautomer, wherein:

$R^a$ is selected from hydrogen, cyano, and $C_1$-$C_3$ alkyl;

$R^b$, $R^c$, $R^d$ and $R^e$ are each independently selected from hydrogen and $C_1$-$C_3$ alkyl;

$R^f$ and $R^g$ are each independently selected from hydrogen, fluoro, cyano, $C_1$-$C_3$ alkyl, and $C_1$-$C_3$ alkoxy;

$R^1$ is selected from hydrogen and $C_1$-$C_3$ alkyl; or $R^1$ is linked to $R^g$ to form the structure (IA):

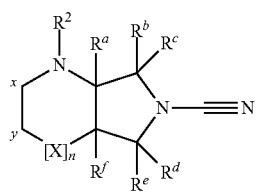

(IA)

n is 0 or 1;

X is selected from O, N($R^h$), and C($R^i$)($R^j$);

positions x and y may be unsubstituted, or each may be independently substituted by $C_1$-$C_3$ alkyl;

$R^h$ is selected from hydrogen, $C_1$-$C_3$ alkyl, C(O)$C_1$-$C_3$ alkyl, and a 3 to 6-membered monocyclic, heteroaryl, aryl, heterocyclyl or cycloalkyl ring;

$R^i$ and $R^j$ are each independently selected from hydrogen, fluoro, cyano, $C_1$-$C_3$ alkyl, $C_1$-$C_3$ alkoxy, and a 3 to 6-membered monocyclic, heteroaryl, aryl, heterocyclyl or cycloalkyl ring;

when X is O or N($R^h$), $R^f$ is not fluoro or $C_1$-$C_3$ alkoxy;

$R^2$ is a 5 to 10-membered, monocyclic or bicyclic, heteroaryl or aryl ring, which may be unsubstituted, or substituted with one or more $Q^1(R^3)_m$ groups, which may be the same or different;

m is 0 or 1;

$Q^1$ is selected from $Q^{1a}$ or $Q^{1b}$;

$Q^{1a}$ is selected from oxo, halo, cyano, nitro, hydroxyl, $SR^6$, $NR^6R^7$, $CONR^6R^7$, $C_0$-$C_3$-alkylene-$NR^6COR^7$, $NR^6CONR^7R^8$, $COR^8$, $C(O)OR^6$, $SO_2R^6$, $SO_2NR^6R^7$, $NR^6SO_2R^7$, $NR^6SO_2NR^7R^8$, $NR^6C(O)OR^7$, $C_1$-$C_6$ alkyl, $C_1$-$C_6$ alkoxy, and $C_2$-$C_6$ alkenyl;

$Q^{1b}$ is selected from a covalent bond, an oxygen atom, a sulphur atom, $OR^9$, SO, $SO_2$, CO, C(O)O, $C_0$-$C_3$ alkylene-C(O)$NR^6$—$C_0$-$C_3$ alkylene, $C_0$-$C_3$ alkylene-$NR^6$—$C_0$-$C_3$ alkylene, $C_0$-$C_3$ alkylene-$NR^6C(O)$—$C_0$-$C_3$ alkylene, $NR^6CONR^7$, $SO_2NR^6$, $NR^6SO_2$, $NR^6SO_2NR^7$, $NR^6C(O)O$, $NR^6C(O)OR^9$, $C_1$-$C_6$ alkylene, and $C_2$-$C_6$ alkenylene;

$R^3$ is a 3 to 10-membered, monocyclic or bicyclic, heterocyclyl, heteroaryl, cycloalkyl or aryl ring;

$R^6$, $R^7$ and $R^8$ are each independently selected from hydrogen and $C_1$-$C_6$ alkyl;

$R^9$ is $C_1$-$C_6$ alkylene;

wherein $R^3$ may be unsubstituted, or substituted with one or more substituents, each independently selected from halo, cyano, oxo, nitro, hydroxyl, $SR^{10}$, $C_1$-$C_6$ alkyl, $C_1$-$C_6$ alkoxy, $C_2$-$C_6$ alkenyl, $C_2$-$C_6$ alkynyl, $Q^{2a}$-$R^{13}$, $Q^{2a}$-O-$Q^{2b}$-$R^{13}$, $Q^{2a}$-S-$Q^{2b}$-$R^{13}$, $Q^{2a}$-SO-$Q^{2b}$-$R^{13}$, $Q^{2a}$-$NR^{10}CONR^{11}R^{12}$, $Q^{2a}$-$NR^{10}CONR^{11}$-$Q^{2a}$-$R^{13}$, $Q^{2a}$-$NR^{10}R^{11}$, $Q^{2a}$-$NR^{10}$-$Q^{2b}$-$R^{13}$, $Q^{2a}$-$COR^{10}$, $Q^{2a}$-CO-$Q^{2b}$-$R^{13}$, $Q^{2a}$-$NR^{10}COR^{11}$, $Q^{2a}$-$NR^{10}CO$-$Q^{2b}$-$R^{13}$, $Q^{2a}$-$NR^{10}C(O)OR^{11}$, $Q^{2a}$-$NR^{10}C(O)O$-$Q^{2b}$-$R^{13}$, $Q^{2a}$-$SO_2R^{10}$, $Q^{2a}$-$SO_2$-$Q^{2b}$-$R^{13}$, $Q^{2a}$-$CONR^{10}R^{11}$, $Q^{2a}$-$CONR^{10}$-$Q^{2b}$-$R^{13}$, $Q^{2a}$-$CO_2R^{10}$, $Q^{2a}$-$CO_2$-$Q^{2b}$-$R^{13}$, $Q^{2a}$-$SO_2NR^{10}R^{11}$, $Q^{2a}$-$SO_2NR^{10}$-$Q^{2b}$-$R^{13}$, $Q^{2a}$-$NR^{10}SO_2R^{11}$, $Q^{2a}$-$NR^{10}SO_2$-$Q^{2b}$-$R^{13}$, $Q^{2a}$-$NR^{10}SO_2NR^{11}R^{12}$, and $Q^{2a}$-$NR^{10}SO_2NR^{11}$-$Q^{2b}$-$R^{13}$;

$Q^{2a}$ and $Q^{2b}$ are each independently selected from a covalent bond, $C_1$-$C_6$ alkylene, and $C_2$-$C_6$ alkenylene;

$R^{10}$, $R^{11}$ and $R^{12}$ are each independently selected from hydrogen and $C_1$-$C_6$ alkyl; and $R^{13}$ is a 3 to 10-membered, monocyclic or bicyclic, heterocyclyl, heteroaryl, cycloalkyl or aryl ring; for use in the treatment of a disorder or condition where inhibition of USP30 is known, or can be shown, to produce a beneficial effect, in a mammal.

In more preferred embodiments of the invention there is provided a compound of formula (I) wherein the substituents are as defined in respect of the first aspect of the invention and preferred embodiments thereof; a tautomer thereof, or a pharmaceutically acceptable salt of said compound or tautomer; for use in the treatment of a disorder or condition where inhibition of USP30 is known, or can be shown, to produce a beneficial effect, in a mammal; and wherein said substituents may be preferably selected as follows:

In one embodiment, where $R^1$ is selected from hydrogen and $C_1$-$C_3$ alkyl:

Preferably, $R^a$ is selected from hydrogen, cyano, methyl, and ethyl. More preferably, $R^a$ is selected from hydrogen and methyl.

Preferably, $R^b$, $R^c$, $R^d$, $R^e$, and $R^g$, are each independently selected from hydrogen, methyl, and ethyl. More preferably, $R^b$, $R^c$, $R^d$, $R^e$, and $R^g$, are each independently selected from hydrogen and methyl. Preferably, $R^f$ is selected from hydrogen, fluoro, cyano, methyl, ethyl, methoxy, and ethoxy. More preferably, $R^f$ is selected from hydrogen and methyl.

In a particularly preferred embodiment, $R^a$, $R^b$, $R^c$, $R^d$, $R^e$, $R^f$, and $R^g$, are each independently selected from hydrogen and methyl. Most preferably, $R^a$, $R^b$, $R^c$, $R^d$, $R^e$, $R^f$, and $R^g$, are each hydrogen.

Preferably, $R^1$ is selected from hydrogen and methyl.

In another embodiment, where $R^1$ is linked to $R^g$ to form the structure (IA):

Preferably, positions x and y are unsubstituted, or each may be independently substituted by cyano, methyl, or ethyl. More preferably, positions x and y are unsubstituted, or each may be independently substituted by methyl. Most preferably, positions x and y are unsubstituted.

When X is N($R^h$), preferably, $R^h$ is selected from hydrogen, methyl, and acetyl. More preferably, $R^h$ is selected from hydrogen and methyl.

When X is C($R^i$)($R^j$), preferably, $R^i$ and $R^j$ are each independently selected from hydrogen and methyl. More preferably, $R^i$ and $R^j$ are each hydrogen.

In a particularly preferred embodiment, where $R^1$ is linked to $R^g$ to form the structure (IA): X is selected from O and $CH_2$; and positions x and y are unsubstituted.

In the embodiments where $R^1$ is selected from hydrogen and $C_1$-$C_3$ alkyl and $R^1$ is linked to $R^g$ to form the structure (IA), and preferred embodiments thereof:

Preferably, $R^2$ is selected from aryl, and a 5 to 10-membered, monocyclic or bicyclic, heteroaryl, which comprises 1 to 4 heteroatoms independently selected from nitrogen, oxygen and sulfur, wherein $R^2$ is unsubstituted, or substituted with 1 to 4, preferably 1 or 2, $Q^1(R^3)_m$ groups, which may be the same or different, and most preferably, $R^2$ is unsubstituted, or substituted with 1 $Q^1(R^3)_m$ group.

More preferably, $R^2$ is selected from phenyl, naphthyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, tetrahydroisoquinolinyl, pyridinyl, pyrazinyl, pyrimidinyl, pyridazinyl, furanyl, thiophenyl, pyrrolyl, oxazolyl, thiazolyl, pyrazolyl, triazolyl, tetrazolyl, indolyl, indolizinyl, isoindolyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, benzoxazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydropyridinyl, dihydropyrrolopyridinyl, quinoxalinyl, dihydrobenzoxazinyl, tetrahydropyridopyrazinyl, tetrahydropyridopyrazinyl, tetrahydroquinolinyl and tetrahydroisoquinolinyl; wherein $R^2$ is unsubstituted, or substituted with 1 to 4, preferably 1 or 2, $Q^1(R^3)_m$ groups, which may be the same or different, and most preferably, $R^2$ is unsubstituted, or substituted with 1 $Q^1(R^3)_m$ group.

Even more preferably, $R^2$ is selected from benzimidazolyl, benzothiazolyl, phenyl, pyrazinyl, pyridazinyl, pyridinyl, pyrimidinyl, and thiazolyl; wherein $R^2$ is unsubstituted, or substituted with 1 to 4, preferably 1 or 2, $Q^1(R^3)_m$ groups, which may be the same or different, and most preferably, $R^2$ is unsubstituted, or substituted with 1 $Q^1(R^3)_m$ group.

In the embodiments and preferred embodiments of $R^2$, the $Q^1(R^3)_m$ groups are preferably selected as follows:

When m is 0; $Q^1$ is $Q^{1a}$, which is preferably selected from halo, cyano, hydroxyl, $N(C_1$-$C_6$ alkyl$)_2$, $CO(C_1$-$C_6$ alkyl), $C(O)O(C_1$-$C_6$ alkyl), $C_1$-$C_6$ alkyl, $C_1$-$C_6$ haloalkyl, $C_1$-$C_6$ alkoxy, and $C_1$-$C_6$ haloalkoxy. More preferably, $Q^1$ is selected from halo, cyano, $C_1$-$C_3$ alkyl, $C_1$-$C_3$ haloalkyl, $C_1$-$C_3$ alkoxy, and $C_1$-$C_3$ haloalkoxy. More preferably, $Q^1$ is selected from fluoro, chloro, cyano, methyl, ethyl, isopropyl, methoxy, ethoxy, $CF_3$, and $OCF_3$. Most preferably, $Q^1$ is selected from fluoro, cyano, methoxy, $CF_3$, and $OCF_3$.

When m is 1; $Q^1$ is $Q^{1b}$, which is preferably selected from a covalent bond, an oxygen atom, a sulphur atom, SO, $SO_2$, CO, C(O)O, NH, N($C_1$-$C_6$ alkyl), and C(O)N($C_1$-$C_6$ alkyl). More preferably, $Q^1$ is selected from a covalent bond, and an oxygen atom. Most preferably, $Q^1$ is a covalent bond.

Preferably, $R^3$ is selected from aryl, and a 5 to 10-membered, monocyclic or bicyclic, heteroaryl, which comprises 1 to 4 heteroatoms independently selected from nitrogen, oxygen and sulfur, wherein $R^3$ is unsubstituted, or substituted with 1 to 4, preferably 1 to 3, most preferably 1 or 2, substituents, each independently selected from halo, cyano, hydroxyl, $N(C_1$-$C_6$ alkyl$)_2$, $CO(C_1$-$C_6$ alkyl), $C(O)O(C_1$-$C_6$ alkyl), $C_1$-$C_6$ alkyl, $C_1$-$C_6$ haloalkyl, $C_1$-$C_6$ alkoxy, and $C_1$-$C_6$ haloalkoxy. More preferably, $R^3$ is unsubstituted, or substituted with 1 to 4, preferably 1 to 3, most preferably 1 or 2, substituents, each independently selected from halo, cyano, $C_1$-$C_3$ alkyl, $C_1$-$C_3$ haloalkyl, $C_1$-$C_3$ alkoxy, and $C_1$-$C_3$ haloalkoxy. Even more preferably, $R^3$ is unsubstituted, or substituted with 1 to 4, preferably 1 to 3, most preferably 1 or 2, substituents, each independently selected from fluoro, chloro, cyano, methyl, ethyl, isopropyl, methoxy, ethoxy, $CF_3$, and $OCF_3$. Most preferably, $R^3$ is unsubstituted, or substituted with cyano.

Preferably, the aryl ring of $R^3$ is phenyl, and the heteroaryl ring is a 5 to 6-membered, monocyclic heteroaryl, which comprises 1 to 3 heteroatoms independently selected from nitrogen, oxygen and sulfur. More preferably, the heteroaryl ring is 6-membered and comprises 1 to 2 nitrogen atoms. Most preferably, the ring of $R^3$ is selected from phenyl and pyridinyl.

In the more preferred embodiments, $R^2$ is unsubstituted, or substituted by 1 $Q^1(R^3)_m$ group, which is selected from fluoro, cyano, methoxy, $CF_3$, $OCF_3$, phenyl, pyridinyl, cyanophenyl, and cyanopyridinyl.

According to a second aspect, the present invention provides a compound of formula (I), which is (IA)

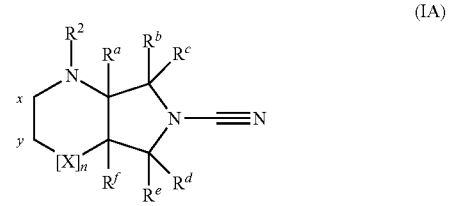

a tautomer thereof, or a pharmaceutically acceptable salt of said compound or tautomer, wherein:

$R^a$ is selected from hydrogen, cyano, and $C_1$-$C_3$ alkyl;

$R^b$, $R^c$, $R^d$ and $R^e$ are each independently selected from hydrogen and $C_1$-$C_3$ alkyl;

$R^f$ is selected from hydrogen, fluoro, cyano, $C_1$-$C_3$ alkyl, and $C_1$-$C_3$ alkoxy;

n is 0 or 1;

X is selected from O, N($R^h$), and C($R^i$)($R^j$);

positions x and y may be unsubstituted, or each may be independently substituted by $C_1$-$C_3$ alkyl;

$R^h$ is selected from hydrogen, $C_1$-$C_3$ alkyl, C(O)$C_1$-$C_3$ alkyl, and a 3 to 6-membered monocyclic, heteroaryl, aryl, heterocyclyl or cycloalkyl ring;

$R^i$ and $R^j$ are each independently selected from hydrogen, fluoro, cyano, $C_1$-$C_3$ alkyl, $C_1$-$C_3$ alkoxy, and a 3 to 6-membered monocyclic, heteroaryl, aryl, heterocyclyl or cycloalkyl ring;

when X is O or N($R^h$), $R^f$ is not fluoro or $C_1$-$C_3$ alkoxy;

$R^2$ is a 5 to 10-membered, monocyclic or bicyclic, heteroaryl or aryl ring, which may be unsubstituted, or substituted with one or more $Q^1(R^3)_m$ groups, which may be the same or different;

m is 0 or 1;

$Q^1$ is selected from $Q^{1a}$ or $Q^{1b}$;

$Q^{1a}$ is selected from oxo, halo, cyano, nitro, hydroxyl, $SR^6$, $NR^6R^7$, $CONR^6R^7$, $C_0$-$C_3$-alkylene-$NR^6COR^7$, $NR^6CONR^7R^8$, $COR^6$, $C(O)OR^6$, $SO_2R^6$, $SO_2NR^6R^7$, $NR^6SO_2R^7$, $NR^6SO_2NR^7R^8$, $NR^6C(O)OR^7$, $C_1$-$C_6$ alkyl, $C_1$-$C_6$ alkoxy, and $C_2$-$C_6$ alkenyl;

$Q^{1b}$ is selected from a covalent bond, an oxygen atom, a sulphur atom, $OR^9$, SO, $SO_2$, CO, C(O)O, $C_0$-$C_3$ alkylene-C(O)$NR^6$—$C_0$-$C_3$ alkylene, $C_0$-$C_3$ alkylene-$NR^6$—$C_0$-$C_3$ alkylene, $C_0$-$C_3$ alkylene-$NR^6$C(O)—$C_0$-$C_3$ alkylene, $NR^6CONR^7$, $SO_2NR^6$, $NR^6SO_2$, $NR^6SO_2NR^7$, $NR^6$C(O)O, $NR^6$C(O)$OR^9$, $C_1$-$C_6$ alkylene, and $C_2$-$C_6$ alkenylene;

$R^3$ is a 3 to 10-membered, monocyclic or bicyclic, heterocyclyl, heteroaryl, cycloalkyl or aryl ring;

$R^6$, $R^7$ and $R^8$ are each independently selected from hydrogen and $C_1$-$C_6$ alkyl;

$R^9$ is $C_1$-$C_6$ alkylene;

wherein $R^3$ may be unsubstituted, or substituted with one or more substituents, each independently selected from halo, cyano, oxo, nitro, hydroxyl, Se, $C_1$-$C_6$ alkyl, $C_1$-$C_6$ alkoxy, $C_2$-$C_6$ alkenyl, $C_2$-$C_6$ alkynyl, $Q^{2a}$-$R^{13}$, $Q^{2a}$-O-$Q^{2b}$-$R^{13}$, $Q^{2a}$-S-$Q^{2b}$-$R^{13}$, $Q^{2a}$-SO-$Q^{2b}$-$R^{13}$, $Q^{2a}$-$NR^{10}CONR^{11}R^{12}$, $Q^{2a}$-$NR^{10}CONR^{11}$-$Q^{2a}$-$R^{13}$-$Q^{2a}$-$NR^{10}$-$Q^{2b}$-$R^{13}$, $Q^{2a}$-$COR^{10}$, $Q^{2a}$-CO-$Q^{2b}$-$R^{13}$, $Q^{2a}$-$NR^{10}COR^{11}$, $Q^{2a}$-$NR^{10}CO$-$Q^{2b}$-$R^{13}$, $Q^{2a}$-$NR^{10}$C(O)$OR^{11}$, $Q^{2a}$-$NR^{10}$C(O)O-$Q^{2b}$-$R^{13}$, $Q^{2a}$-$SO_2R^{10}$, $Q^{2a}$-$SO_2$-$Q^{2b}$-$R^{13}$, $Q^{2a}$-$CONR^{10}R^{11}$, $Q^{2a}$-$CONR^{10}$-$Q^{2b}$-$R^{13}$, $Q^{2a}$-$CO_2R^{10}$, $Q^{2a}$-$CO_2$-$Q^{2b}$-$R^{13}$, $Q^{2a}$-$SO_2NR^{10}R^{11}$, $Q^{2a}$-$SO_2NR^{10}$-$Q^{2b}$-$R^{13}$, $Q^{2a}$-$NR^{10}SO_2R^{11}$, $Q^{2a}$-$NR^{10}SO_2$-$Q^{2b}$-$R^{13}$, $Q^{2a}$-$NR^{10}SO_2NR^{11}R^{12}$, $Q^{2a}$-$NR^{10}SO_2NR^{11}$-$Q^{2b}$-$R^{13}$;

$Q^{2a}$ and $Q^{2b}$ are each independently selected from a covalent bond, $C_1$-$C_6$ alkylene, and $C_2$-$C_6$ alkenylene;

$R^{10}$, $R^{11}$ and $R^{12}$ are each independently selected from hydrogen and $C_1$-$C_6$ alkyl; and $R^{13}$ is a 3 to 10-membered, monocyclic or bicyclic, heterocyclyl, heteroaryl, cycloalkyl or aryl ring;

Preferred embodiments of the substituents $R^a$, $R^b$, $R^c$, $R^d$, $R^e$, $R^f$, X, n, x, y, and $R^2$, of the compound of formula (IA) of the second aspect of the invention, are as defined herein in respect of the first aspect of the invention and preferred embodiments thereof.

In one preferred embodiment of the compound of formula (IA);

$R^a$, $R^b$, $R^c$, $R^d$, $R^e$, and $R^f$, are each hydrogen;

positions x and y are unsubstituted; and $R^2$ is selected from aryl, and a 5 to 6-membered monocyclic, or a 9 to 10-membered bicyclic, heteroaryl ring, which comprises 1 to 4 heteroatoms independently selected from nitrogen, oxygen and sulfur, wherein $R^2$ is unsubstituted, or substituted with 1 to 4 $Q^1(R^3)_m$ groups, preferably 1 or 2 $Q^1(R^3)_m$ groups, and most preferably 1 $Q^1(R^3)_m$ group, which are each independently selected from:

(i) (m is 0) halo, cyano, $C_1$-$C_3$ alkyl, $C_1$-$C_3$ haloalkyl, $C_1$-$C_3$ alkoxy, and $C_1$-$C_3$ haloalkoxy; and (ii) (m is 1) phenyl, and a 5 to 6-membered, monocyclic heteroaryl, which comprises 1 to 3 heteroatoms independently selected from nitrogen, oxygen and sulfur, wherein the phenyl or heteroaryl ring is unsubstituted, or substituted with a group selected from halo, cyano, $C_1$-$C_3$ alkyl, $C_1$-$C_3$ haloalkyl, $C_1$-$C_3$ alkoxy, and $C_1$-$C_3$ haloalkoxy.

In a more preferred embodiment of the compound of formula (IA);

$R^a$, $R^b$, $R^c$, $R^d$, $R^e$, and $R^f$, are each hydrogen;

positions x and y are unsubstituted; and $R^2$ is selected from benzimidazolyl, benzothiazolyl, pyrazinyl, pyridazinyl, pyridinyl, pyrimidinyl, thiazolyl, and optionally phenyl; wherein $R^2$ is unsubstituted, or substituted with 1 to 4 $Q^1(R^3)_m$ groups, preferably 1 or 2 $Q^1(R^3)_m$ groups, and most preferably 1 $Q^1(R^3)_m$ group, which are each independently selected from:

(i) (m is 0) halo, cyano, $C_1$-$C_3$ alkyl, $C_1$-$C_3$ haloalkyl, $C_1$-$C_3$ alkoxy, and $C_1$-$C_3$ haloalkoxy; and (ii) (m is 1) phenyl, and pyridinyl, wherein the phenyl or pyridinyl ring is unsubstituted, or substituted with a group selected from halo, cyano, $C_1$-$C_3$ alkyl, $C_1$-$C_3$ haloalkyl, $C_1$-$C_3$ alkoxy, and $C_1$-$C_3$ haloalkoxy.

In a more preferred embodiment of the compound of formula (IA);

$R^a$, $R^b$, $R^c$, $R^d$, $R^e$, and $R^f$, are each hydrogen;

positions x and y are unsubstituted; and $R^2$ is selected from benzimidazolyl, benzothiazolyl, pyrazinyl, pyridazinyl, pyridinyl, pyrimidinyl, thiazolyl, and optionally phenyl; wherein $R^2$ is unsubstituted, or substituted by 1 $Q^1(R^3)_m$ group, which is selected from fluoro, cyano, methoxy, $CF_3$, $OCF_3$, phenyl, pyridinyl, cyanophenyl, and cyanopyridinyl.

One preferred embodiment of the compound of formula (IA) is (IIA)(i):

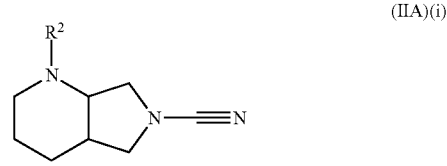

(IIA)(i)

wherein $R^2$ is as defined herein in respect of the first and second aspects of the invention and preferred embodiments thereof;

a tautomer thereof, or a pharmaceutically acceptable salt of said compound or tautomer.

Another preferred embodiment of the compound of formula (IA) is (IIB)(i):

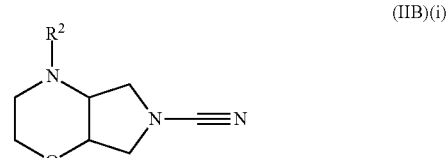

(IIB)(i)

wherein $R^2$ is as defined herein in respect of the first and second aspects of the invention and preferred embodiments thereof;

a tautomer thereof, or a pharmaceutically acceptable salt of said compound or tautomer.

Another preferred embodiment of the compound of formula (IA) is (IIC)(i):

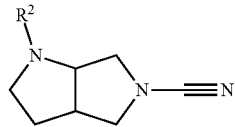

(IIC)(i)

wherein $R^2$ is as defined herein in respect of the first and second aspects of the invention and preferred embodiments thereof;

a tautomer thereof, or a pharmaceutically acceptable salt of said compound or tautomer.

According to a third aspect, the present invention provides a compound of formula (I), which is (IB)

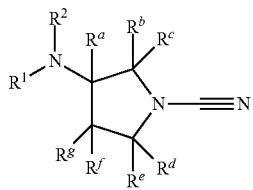

(IB)

a tautomer thereof, or a pharmaceutically acceptable salt of said compound or tautomer, wherein:

$R^a$ is selected from hydrogen, cyano, and $C_1$-$C_3$ alkyl;

$R^b$, $R^c$, $R^d$ and $R^e$ are each independently selected from hydrogen and $C_1$-$C_3$ alkyl;

$R^f$ and $R^g$ are each independently selected from hydrogen, fluoro, cyano, $C_1$-$C_3$ alkyl, and $C_1$-$C_3$ alkoxy;

$R^1$ is selected from hydrogen and $C_1$-$C_3$ alkyl;

$R^2$ is a 5 to 10-membered, monocyclic or bicyclic, heteroaryl or aryl ring, which may be unsubstituted, or substituted with one or more $Q^1(R^3)_m$ groups, which may be the same or different;

m is 0 or 1;

$Q^1$ is selected from $Q^{1a}$ or $Q^{1b}$;

$Q^{1a}$ is selected from oxo, halo, cyano, nitro, hydroxyl, $SR^6$, $NR^6R^7$, $CONR^6R^7$, $C_0$-$C_3$-alkylene-$NR^6COR^7$, $NR^6CONR^7R^8$, $COR^6$, $C(O)OR^6$, $SO_2R^6$, $SO_2NR^6R^7$, $NR^6SO_2R^7$, $NR^6SO_2NR^7R^8$, $NR^6C(O)OR^7$, $C_1$-$C_6$ alkyl, $C_1$-$C_6$ alkoxy, and $C_2$-$C_6$ alkenyl;

$Q^{1b}$ is selected from a covalent bond, an oxygen atom, a sulphur atom, $OR^9$, SO, $SO_2$, CO, $C(O)O$, $C_0$-$C_3$ alkylene-$C(O)NR^6$—$C_0$-$C_3$ alkylene, $C_0$-$C_3$ alkylene-$NR^6$—$C_0$-$C_3$ alkylene, $C_0$-$C_3$ alkylene-$NR^6C(O)$—$C_0$-$C_3$ alkylene, $NR^6CONR^7$, $SO_2NR^6$, $NR^6SO_2$, $NR^6SO_2NR^7$, $NR^6C(O)O$, $NR^6C(O)OR^9$, $C_1$-$C_6$ alkylene, and $C_2$-$C_6$ alkenylene;

$R^3$ is a 3 to 10-membered, monocyclic or bicyclic, heterocyclyl, heteroaryl, cycloalkyl or aryl ring;

$R^6$, $R^7$ and $R^8$ are each independently selected from hydrogen and $C_1$-$C_6$ alkyl;

$R^9$ is $C_1$-$C_6$ alkylene;

wherein $R^3$ may be unsubstituted, or substituted with one or more substituents, each independently selected from halo, cyano, oxo, nitro, hydroxyl, Se, $C_1$-$C_6$ alkyl, $C_1$-$C_6$ alkoxy, $C_2$-$C_6$ alkenyl, $C_2$-$C_6$ alkynyl, $Q^{2a}$-$R^{13}$, $Q^{2a}$-O-$Q^{2b}$-$R^{13}$, $Q^{2a}$-S-$Q^{2b}$-$R^{13}$, $Q^{2a}$-SO-$Q^{2b}$-$R^{13}$, $Q^{2a}$-$NR^{10}CONR^{11}R^{12}$, $Q^{2a}$-$NR^{10}CONR^{11}$-$Q^{2a}$-$R^{13}$, $Q^{2a}$-$NR^{10}R^{11}$, $Q^{2a}$-$NR^{10}$-$Q^{2b}$-$R^{13}$, $Q^{2a}$-$COR^{10}$, $Q^{2a}$-$CO$-$Q^{2b}$-$R^{13}$, $Q^{2a}$-$NR^{10}COR^{11}$, $Q^{2a}$-$NR^{10}CO$-$Q^{2b}$-$R^{13}$, $Q^{2a}$-$NR^{10}C(O)OR^{11}$, $Q^{2a}$-$NR^{10}C(O)O$-$Q^{2b}$-$R^{13}$, $Q^{2a}$-$SO_2R^{10}$, $Q^{2a}$-$SO_2$-$Q^{2b}$-$R^{13}$, $Q^{2a}$-$CONR^{10}R^{11}$, $Q^{2a}$-$CONR^{10}$-$Q^{2b}$-$R^{13}$, $Q^{2a}$-$COR^{10}$, $Q^{2a}$-$CO_2$-$Q^{2b}$-$R^{13}$, $Q^{2a}$-$SO_2NR^{10}R^{11}$, $Q^{2a}$-$SO_2NR^{10}$-$Q^{2b}$-$R^{13}$, $Q^{2a}$-$NR^{10}SO_2R^{11}$, $Q^{2a}$-$NR^{10}SO_2$-$Q^{2b}$-$R^{13}$, $Q^{2a}$-$NR^{10}SO_2NR^{11}R^{12}$, and $Q^{2a}$-$NR^{10}SO_2NR^{11}$-$Q^{2b}$-$R^{13}$;

$Q^{2a}$ and $Q^{2b}$ are each independently selected from a covalent bond, $C_1$-$C_6$ alkylene, and $C_2$-$C_6$ alkenylene;

$R^{10}$, $R^{11}$ and $R^{12}$ are each independently selected from hydrogen and $C_1$-$C_6$ alkyl; and $R^{13}$ is a 3 to 10-membered, monocyclic or bicyclic, heterocyclyl, heteroaryl, cycloalkyl or aryl ring;

Preferred embodiments of the substituents $R^a$, $R^b$, $R^c$, $R^d$, $R^e$, $R^f$, $R^g$, $R^1$, and $R^2$, of the compound of formula (IB) of the second aspect of the invention, are as defined herein in respect of the first aspect of the invention and preferred embodiments thereof.

In one preferred embodiment of the compound of formula (IB);

$R^a$, $R^b$, $R^c$, $R^d$, $R^e$, $R^f$, and $R^g$, are each hydrogen;

$R^1$ is selected from hydrogen and $C_1$-$C_3$ alkyl, and is preferably selected from hydrogen and methyl.

$R^2$ is selected from aryl, and a 5 to 6-membered monocyclic, or a 9 to 10-membered bicyclic, heteroaryl ring, which comprises 1 to 4 heteroatoms independently selected from nitrogen, oxygen and sulfur, wherein $R^2$ is unsubstituted, or substituted with 1 to 4 $Q^1(R^3)_m$ groups, preferably 1 or 2 $Q^1(R^3)_m$ groups, and most preferably 1 $Q^1(R^3)_m$ group, which are each independently selected from:

(i) (m is 0) halo, cyano, $C_1$-$C_3$ alkyl, $C_1$-$C_3$ haloalkyl, $C_1$-$C_3$ alkoxy, and $C_1$-$C_3$ haloalkoxy; and (ii) (m is 1) phenyl, and a 5 to 6-membered, monocyclic heteroaryl, which comprises 1 to 3 heteroatoms independently selected from nitrogen, oxygen and sulfur, wherein the phenyl or heteroaryl ring is unsubstituted, or substituted with a group selected from halo, cyano, $C_1$-$C_3$ alkyl, $C_1$-$C_3$ haloalkyl, $C_1$-$C_3$ alkoxy, and $C_1$-$C_3$ haloalkoxy.

In a more preferred embodiment of the compound of formula (IB);

$R^a$, $R^b$, $R^c$, $R^d$, $R^e$, $R^f$, and $R^g$, are each hydrogen;

$R^1$ is selected from hydrogen and $C_1$-$C_3$ alkyl, and is preferably selected from hydrogen and methyl; and $R^2$ is a 5 to 6-membered monocyclic, or a 9 to 10-membered bicyclic, heteroaryl ring, which comprises 1 to 4 heteroatoms independently selected from nitrogen, oxygen and sulfur, wherein $R^2$ is unsubstituted, or substituted with 1 to 4 $Q^1(R^3)_m$ groups, preferably 1 or 2 $Q^1(R^3)_m$ groups, and most preferably 1 $Q^1(R^3)_m$ group, which are each independently selected from:

(i) (m is 0) halo, cyano, $C_1$-$C_3$ alkyl, $C_1$-$C_3$ haloalkyl, $C_1$-$C_3$ alkoxy, and $C_1$-$C_3$ haloalkoxy; and (ii) (m is 1) phenyl, and a 5 to 6-membered, monocyclic heteroaryl, which comprises 1 to 3 heteroatoms independently selected from nitrogen, oxygen and sulfur, wherein the phenyl or heteroaryl ring is unsubstituted, or substituted with a group selected from halo, cyano, $C_1$-$C_3$ alkyl, $C_1$-$C_3$ haloalkyl, $C_1$-$C_3$ alkoxy, and $C_1$-$C_3$ haloalkoxy.

In a more preferred embodiment of the compound of formula (IB);

$R^a$, $R^b$, $R^c$, $R^d$, $R^e$, $R^f$, and $R^g$, are each hydrogen;

$R^1$ is selected from hydrogen and $C_1$-$C_3$ alkyl, and is preferably selected from hydrogen and methyl; and $R^2$ is selected from benzimidazolyl, pyridinyl, and thiazolyl; wherein $R^2$ is unsubstituted, or substituted with 1 to 4 $Q^1(R^3)_m$ groups, preferably 1 or 2 $Q^1(R^3)_m$ groups, and most preferably 1 $Q^1(R^3)_m$ group, which are each independently selected from:

(i) (m is 0) halo, cyano, $C_1$-$C_3$ alkyl, $C_1$-$C_3$ haloalkyl, $C_1$-$C_3$ alkoxy, and $C_1$-$C_3$ haloalkoxy; and (ii) (m is 1) phenyl, and pyridinyl, wherein the phenyl or pyridinyl ring is unsubstituted, or substituted with a group selected from halo, cyano, $C_1$-$C_3$ alkyl, $C_1$-$C_3$ haloalkyl, $C_1$-$C_3$ alkoxy, and $C_1$-$C_3$ haloalkoxy.

In a more preferred embodiment of the compound of formula (IB);

$R^a$, $R^b$, $R^c$, $R^d$, $R^e$, $R^f$, and $R^g$, are each hydrogen;

$R^1$ is selected from hydrogen and $C_1$-$C_3$ alkyl, and is preferably selected from hydrogen and methyl; and $R^2$ is selected from benzimidazolyl, pyridinyl, and thiazolyl; wherein $R^2$ is unsubstituted, or substituted by 1 $Q^1(R^3)_m$ group, which is selected from fluoro, cyano, methoxy, $CF_3$, $OCF_3$, phenyl, pyridinyl, cyanophenyl, and cyanopyridinyl.

One preferred embodiment of the compound of formula (IB) is (IB)(i):

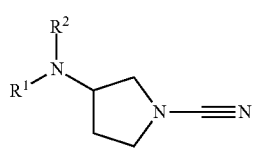

(IB)(i)

wherein $R^1$ and $R^2$ are as defined herein in respect of the first and third aspects of the invention and preferred embodiments thereof;

a tautomer thereof, or a pharmaceutically acceptable salt of said compound or tautomer.

Preferred compounds of formula (I) according to all aspects of the present invention are selected from:

1-phenylhexahydropyrrolo[3,4-b]pyrrole-5(1H)-carbonitrile;
(4aR,7aS)-4-(6-phenylpyridazin-3-yl)hexahydropyrrolo[3,4-b][1,4]oxazine-6(2H)-carbonitrile;
(4aR,7aS)-4-(6-fluorobenzo[d]thiazol-2-yl)hexahydropyrrolo[3,4-b][1,4]oxazine-6(2H)-carbonitrile;
(4aR,7aS)-4-(4-phenylpyridin-2-yl)hexahydropyrrolo[3,4-b][1,4]oxazine-6(2H)-carbonitrile;
(4aR,7aS)-4-(5-phenylpyridin-2-yl)hexahydropyrrolo[3,4-b][1,4]oxazine-6(2H)-carbonitrile;
(4aR,7aS)-4-(6-phenylpyridin-2-yl)hexahydropyrrolo[3,4-b][1,4]oxazine-6(2H)-carbonitrile;
(4aR,7aS)-4-(4-phenylpyrimidin-2-yl)hexahydropyrrolo[3,4-b][1,4]oxazine-6(2H)-carbonitrile;
(3aS,6aS)-1-(5-phenylthiazol-2-yl)hexahydropyrrolo[3,4-b]pyrrole-5(1H)-carbonitrile;
(4aR,7aS)-4-(5-phenylthiazol-2-yl)hexahydropyrrolo[3,4-b][1,4]oxazine-6(2H)-carbonitrile;
(4aR,7aR)-4-(5-phenylthiazol-2-yl)hexahydropyrrolo[3,4-b][1,4]oxazine-6(2H)-carbonitrile;
1-(5-phenylthiazol-2-yl)octahydro-6H-pyrrolo[3,4-b]pyridine-6-carbonitrile;
3-((5-phenyl thiazol-2-yl)amino)pyrrolidine-1-carbonitrile;
3-(methyl(5-phenylthiazol-2-yl)amino)pyrrolidine-1-carbonitrile;
3-(methyl(5-phenylpyridin-2-yl)amino)pyrrolidine-1-carbonitrile;
(3aR,6aR)-1-(6-(trifluoromethoxy)-1H-benzo[d]imidazol-2-yl)hexahydropyrrolo[3,4-b]pyrrole-5(1H)-carbonitrile;
2-((3aR,6aR)-5-cyanohexahydropyrrolo[3,4-b]pyrrol-1(2H)-yl)-1H-benzo[d]imidazole-6-carbonitrile;
(3aR,6aR)-1-(6-methoxy-1H-benzo[d]imidazol-2-yl)hexahydropyrrolo[3,4-b]pyrrole-5 (1H)-carbonitrile;
(R)-3-(methyl(6-(trifluoromethyl)-1H-benzo[d]imidazol-2-yl)amino)pyrrolidine-1-carbonitrile;
rac-(4aR,7aS)-4-(2'-cyano-[3,4'-bipyridin]-6-yl)hexahydropyrrolo[3,4-b][1,4]oxazine-6(2H)-carbonitrile;
rac-(4aR,7aS)-4-(2'-cyano-[3,4'-bipyridin]-6-yl)hexahydropyrrolo[3,4-b][1,4]oxazine-6(2H)-carbonitrile;
(4aS,7aR)-4-(6-(2-cyanopyridin-4-yl)pyridazin-3-yl)hexahydropyrrolo[3,4-b][1,4]oxazine-6(2H)-carbonitrile;
(4aR,7aS)-4-(6-(2-cyanopyridin-4-yl)pyridazin-3-yl)hexahydropyrrolo[3,4-b][1,4]oxazine-6(2H)-carbonitrile;
rac-(4aR,7aS)-4-(5-(3-cyanophenyl)pyridin-6-yl)hexahydropyrrolo[3,4-b][1,4]oxazine-6(2H)-carbonitrile;
rac-(4aR,7aS)-4-(5-(3-cyanophenyl)pyrimidin-2-yl)hexahydropyrrolo[3,4-b][1,4]oxazine-6(2H)-carbonitrile;
rac-(4aR,7aS)-4-(5-(3-cyanophenyl)pyrazin-2-yl)hexahydropyrrolo[3,4-b][1,4]oxazine-6(2H)-carbonitrile;
rac-(4aR,7aS)-4-(4-cyano-[2,3'-bipyridin]-6'-yl)hexahydropyrrolo[3,4-b][1,4]oxazine-6(2H)-carbonitrile; and
rac-(4aR,7aS)-4-(2-cyano-[2,3'-bipyridin]-6'-yl)hexahydropyrrolo[3,4-b][1,4]oxazine-6(2H)-carbonitrile;

a tautomer thereof, or a pharmaceutically acceptable salt of said compound or tautomer.

Pharmaceutical acceptable salts of the compounds of formula (I) include the acid addition and base salts (including di-salts) thereof.

Suitable acid addition salts are formed from acids which form non-toxic salts.

Examples include the acetate, aspartate, benzoate, besylate, bicarbonate/carbonate, bisulfate, camsylate, citrate, edisylate, esylate, fumarate, gluceptate, gluconate, glucuronate, hibenzate, hydrochloride/chloride, hydrobromide/bromide, hydroiodide/iodide, hydrogen phosphate, isethionate, D and L-lactate, malate, maleate, malonate, mesylate, methylsulfate, 2-napsylate, nicotinate, nitrate, orotate, palmate, phosphate, saccharate, stearate, succinate sulfate, D- and L-tartrate, and tosylate salts.

Suitable base salts are formed from bases which form non-toxic salts. Examples include the aluminium, ammonium, arginine, benzathine, calcium, choline, diethylamine, diolamine, glycine, lysine, magnesium, meglumine, olamine, potassium, sodium, tromethamine and zinc salts.

For a review on suitable salts, see Stahl and Wermuth, Handbook of Pharmaceutical Salts: Properties, Selection, and Use, Wiley-VCH, Weinheim, Germany (2002).

A pharmaceutical acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent.

Pharmaceutical acceptable solvates in accordance with the invention include hydrates and solvates wherein the solvent of crystallization may be isotopically substituted, e.g. $D_2O$, acetone-d6, DMSO-d6.

Also within the scope of the invention are clathrates, drug-host inclusion complexes wherein, in contrast to the aforementioned solvates, the drug and host are present in non-stoichiometric amounts. For a review of such complexes, see J. Pharm Sci, 64 (8), 1269-1288 by Haleblian (August 1975).

Hereinafter all references to compounds of formula (I) include references to salts thereof and to solvates and clathrates of compounds of formula (I) and salts thereof.

The invention includes all polymorphs of the compounds of formula (I) as hereinbefore defined.

Also within the scope of the invention are so-called "prodrugs" of the compounds of formula (I). Thus, certain derivatives of compounds of formula (I) which have little or no pharmacological activity themselves can, when metabolised upon administration into or onto the body, give rise to compounds of formula (I) having the desired activity. Such derivatives are referred to as "prodrugs".

Prodrugs in accordance with the invention can, for example, be produced by replacing appropriate functionalities present in the compounds of formula (I) with certain moieties known to those skilled in the art as "pro-moieties" as described, for example, in "Design of Prodrugs" by H Bundgaard (Elsevier, 1985).

Finally, certain compounds of formula (I) may themselves act as prodrugs of other compounds of formula (I).

Certain derivatives of compounds of formula (I) which contain a nitrogen atom may also form the corresponding N-oxide, and such compounds are also within the scope of the present invention.

Compounds of formula (I) containing one or more asymmetric carbon atoms can exist as two or more optical isomers. Where a compound of formula (I) contains an alkenyl or alkenylene group, geometric cis/trans (or Z/E) isomers are possible, and where the compound contains, for example, a keto or oxime group, tautomeric isomerism ('tautomerism') may occur. It follows that a single compound may exhibit more than one type of isomerism.

Included within the scope of the present invention are all optical isomers, geometric isomers and tautomeric forms of the compounds of formula, including compounds exhibiting more than one type of isomerism, and mixtures of one or more thereof.

Cis/trans isomers may be separated by conventional techniques well known to those skilled in the art, for example, fractional crystallisation and chromatography.

Conventional techniques for the preparation/isolation of individual enantiomers include chiral synthesis from a suitable optically pure precursor or resolution of the racemate (or the racemate of a salt or derivative) using, for example, chiral high performance liquid chromatography (HPLC). Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person. Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture. The present invention includes all crystal forms of the compounds of formula (I) including racemates and racemic mixtures (conglomerates) thereof. Stereoisomeric conglomerates may be separated by conventional techniques known to those skilled in the art—see, for example, "Stereochemistry of Organic Compounds" by E. L. Eliel and S. H. Wilen (Wiley, New York, 1994).

According to a further aspect of the invention there is provided a process for the preparation of a compound of formula (I) or a pharmaceutically acceptable salt thereof comprising the step of reacting an amine of formula (III) with cyanogen bromide to form N—CN compounds of formula (I):

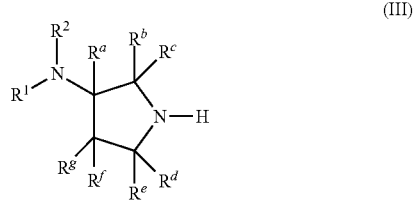

wherein $R^a$, $R^b$, $R^c$, $R^d$, $R^e$, $R^f$, $R^g$, $R^1$ and $R^2$ are as defined herein.

According to a further aspect of the invention there is provided a compound of formula (III) wherein $R^a$, $R^b$, $R^c$, $R^d$, $R^e$, $R^f$, $R^g$, $R^1$ and $R^2$ are as defined herein, and the individual isomers thereof.

The present invention also includes all pharmaceutically acceptable isotopic variations of a compound of formula (I). An isotopic variation is defined as one in which at least one atom is replaced by an atom having the same atomic number, but an atomic mass different from the atomic mass usually found in nature.

Examples of isotopes suitable for inclusion in the compounds of the invention include isotopes of hydrogen, such as $^2H$ and $^3H$, carbon, such as $^{13}C$ and $^{14}C$, nitrogen, such as $^{15}N$, oxygen, such as $^{17}O$ and $^{18}O$, phosphorus, such as $^{32}P$, sulfur, such as $^{35}S$, fluoro, such as $^{18}F$, and chloro, such as $^{36}Cl$.

The isotopes may be radioactive or non-radioactive. In one embodiment, the compounds contain no radioactive isotopes. Such compounds are preferred for therapeutic use. In another embodiment, however, the compounds may contain one or more radioisotopes. Compounds containing such radioisotopes may be useful in a diagnostic context.

Certain isotopically labelled compounds of formula (I), for example, those incorporating a radioactive isotope, are useful in drug and/or substrate tissue distribution studies. The radioactive isotopes i.e. $^3H$ and $^{14}C$ are particularly useful for this purpose in view of their ease of incorporation and ready means of detection. Substitution with heavier isotopes i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining receptor occupancy. Isotopically labelled compounds of formula (I) can generally be prepared by conventional techniques known to those skilled in the art or by processes analogous to those described in the accompanying examples and preparations using an appropriate isotopically labelled reagent in place of the non-labelled reagent previously employed.

The compounds of formula (I) may exist in crystalline or amorphous form and some of the crystalline forms may exist as polymorphs, which are included within the scope of the present invention. Polymorphic forms of compounds of formula (I) may be characterised and differentiated using a number of conventional analytical techniques, including, but not limited to, infra-red spectra, Raman spectra, X-ray powder diffraction, differential scanning calorimetry, thermogravimetric analysis and solid state nuclear magnetic resonance.

Accordingly, in further embodiments, the invention provides a compound according to any described embodiments in a crystalline form. The compound may be from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline. The compound may alternatively be in an amorphous form.

The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

The invention relates to any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates. For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Compounds of the invention may be metabolised in vivo. Metabolites of compounds of formula (I) are also within the scope of the present invention. The term 'metabolites' refers to all molecules derived from any of the compounds according to the present invention in a cell or organism, preferably mammal. Preferably the term relates to molecules which differ from any molecule which is present in any such cell or organism under physiological conditions.

A treatment defined herein may be applied as a sole therapy of may involve, in addition to the compounds of the invention, conventional surgery or radiotherapy or chemotherapy. Furthermore, compounds of formula (I) can also be used in combination with existing therapeutic agents for the treatment of conditions associated with cancer, including small molecule therapeutics or antibody based therapeutics.

According to a further aspect, the present invention provides a pharmaceutical composition comprising a compound of formula (I) as defined herein, or a pharmaceutically acceptable salt of said compound or tautomer, together with a pharmaceutically acceptable diluent or carrier.

Pharmaceutical compositions of the invention comprise any of the compounds of the invention combined with any pharmaceutically acceptable carrier, adjuvant or vehicle. Examples of pharmaceutically acceptable carriers are known to those skilled in the art and include, but are not limited to, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may be in the form of, for example, tablets, capsules, powders, granules, elixirs, lozenges, suppositories, syrups and liquid preparations including suspensions and solutions. The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms.

The compounds of formula (I) are inhibitors of the deubiquitylating enzyme USP30.

According to a further aspect, the present invention provides a compound of formula (I) as defined herein, a tautomer thereof, or a pharmaceutically acceptable salt of said compound or tautomer for use as a medicament.

According to a further aspect, the present invention provides a method of treatment of a disorder or condition where inhibition of USP30 is known, or can be shown, to produce a beneficial effect, in a mammal, comprising administering to said mammal a therapeutically effective amount of a compound of formula (I) as defined herein, a tautomer thereof, or a pharmaceutically acceptable salt of said compound or tautomer.

According to a further aspect, the present invention provides the use of a compound of formula (I) as defined herein, a tautomer thereof, or a pharmaceutically acceptable salt of said compound or tautomer, in the preparation of a medicament for the treatment of a disorder or condition where inhibition of USP30 is known, or can be shown, to produce a beneficial effect.

The term "treat" or "treating" or "treatment" includes prophylaxis and means to ameliorate, alleviate symptoms, eliminate the causation of the symptoms either on a temporary or permanent basis, or to prevent or slow the appearance of symptoms of the named disorder or condition. The compounds of the invention are useful in the treatment of humans and non-human animals.

The dose of the compound is that amount effective to prevent occurrence of the symptoms of the disorder or to treat some symptoms of the disorder from which the patient suffers. By "effective amount" or "therapeutically effective amount" or "effective dose" is meant that amount sufficient to elicit the desired pharmacological or therapeutic effects, thus resulting in effective prevention or treatment of the disorder. Prevention of the disorder is manifested by delaying the onset of the symptoms of the disorder to a medically significant extent. Treatment of the disorder is manifested by a decrease in the symptoms associated with the disorder or an amelioration of the reoccurrence of the symptoms of the disorder.

The disorder or condition benefiting from USP30 activity is selected from a condition involving mitochondrial dysfunction, and cancer.

In one preferred embodiment of all aspects of the invention, the disorder or condition benefiting from USP30 activity is a condition involving mitochondrial dysfunction.

Mitochondrial dysfunctions result from defects of the mitochondria, which are specialized compartments present in every cell of the body except red blood cells. When mitochondria fail, less and less energy is generated within the cell and cell injury or even cell death will follow. If this process is repeated throughout the body the life of the subject in whom this is happening is severely compromised. Diseases of the mitochondria appear most often in organs that are very energy demanding such as the brain, heart, liver, skeletal muscles, kidney and the endocrine and respiratory system.

The condition involving mitochondrial dysfunction may be selected from a condition involving a mitophagy defect, a condition involving a mutation in mitochondrial DNA, a condition involving mitochondrial oxidative stress, a condition involving a defect in mitochondrial membrane potential, mitochondrial biogenesis, a condition involving a defect in mitochondrial shape or morphology, and a condition involving a lysosomal storage defect.

In particular, the condition involving mitochondrial dysfunction may be selected from a neurodegenerative disease; multiple sclerosis (MS); mitochondrial myopathy; encephalopathy; lactic acidosis; stroke-like episodes (MELAS) syndrome; Leber's hereditary optic neuropathy (LHON); cancer (including, for example, breast, ovarian, prostate, lung, kidney, gastric, colon, testicular, head and neck, pancreas, brain, melanoma, bone or other cancers of tissue organs and cancers of the blood cells, such as lymphoma and leukaemia, multiple myeloma, colorectal cancer, and non-small cell lung carcinoma); neuropathy, ataxia, retinitis pigmentosa, maternally inherited Leigh syndrome (NARP-MILS); Danon disease; diabetes; diabetic nephropathy; metabolic disorders; heart failure; ischemic heart disease leading to myocardial infarction; psychiatric diseases, for example schizophrenia; multiple sulfatase deficiency (MSD); mucolipidosis II (ML II); mucolipidosis III (ML III); mucolipidosis IV (ML IV); GM1-gangliosidosis (GM1); neuronal ceroid-lipofuscinoses (NCL1); Alpers disease; Barth syndrome; Beta-oxidation defects; carnitine-acyl-carnitine deficiency; carnitine deficiency; creatine deficiency syndromes; co-enzyme Q10 deficiency; complex I deficiency; complex II deficiency; complex III deficiency; complex IV deficiency; complex V deficiency; COX deficiency; chronic progressive external ophthalmoplegia syndrome (CPEO); CPT I deficiency; CPT II deficiency; glutaric aciduria type II; Kearns-Sayre syndrome; lactic acidosis; long-chain acyl-CoA dehydrogenase deficiency (LCHAD); Leigh disease or syndrome; lethal infantile cardiomyopathy (LIC); Luft disease; glutaric aciduria type II; medium-chain acyl-CoA dehydrogenase deficiency (MCAD); myoclonic epilepsy and ragged-red fiber (MERRF) syndrome; mitochondrial cytopathy; mitochondrial recessive ataxia syndrome; mitochondrial DNA depletion syndrome; myoneurogastrointestinal disorder and encephalopathy; Pearson syndrome; pyruvate dehydrogenase deficiency; pyruvate carboxylase deficiency; POLG mutations; medium/short-chain 3-hydroxyacyl-CoA dehydrogenase (M/SCHAD) deficiency; very long-chain acyl-CoA dehydrogenase (VLCAD) deficiency; and age-dependent decline in cognitive function and muscle strength.

The condition involving mitochondrial dysfunction may be a CNS disorder, for example a neurodegenerative disease.

Neurodegenerative diseases include, but are not limited to, Parkinson's disease, Alzheimer's disease, amyotrophic lateral sclerosis (ALS), Huntington's disease, ischemia, stroke, dementia with Lewy bodies, and frontotemporal dementia.

In particular, the compounds of the invention may be useful in the treatment of Parkinson's disease, including, but not limited to, PD related to mutations in α-synuclein, parkin and PINK', autosomal recessive juvenile Parkinson's disease (AR-JP) where parkin is mutated.

The compounds of the invention or pharmaceutical compositions thereof as described herein may be combined with one or more additional agents when used for the treatment of conditions involving mitochondrial dysfunction. The compounds may be combined with one or more additional agents selected from levodopa, a dopamine agonist, a monoamino oxygenase (MAO) B inhibitor, a catechol O-methyltransferase (COMT) inhibitor, an anticholinergic, riluzole, amantadine, a cholinesterase inhibitor, memantine, tetrabenazine, an antipsychotic, diazepam, clonazepam, an antidepressant, and an anti-convulsant.

In another preferred embodiment of all aspects of the invention, the disorder or condition benefiting from USP30 activity is cancer. The cancer may be linked to mitochondrial dysfunction. Preferred cancers include, for example, breast, ovarian, prostate, lung, kidney, gastric, colon, testicular, head and neck, pancreas, brain, melanoma, bone or other cancers of tissue organs and cancers of the blood cells, such as lymphoma and leukaemia, multiple myeloma, colorectal cancer, and non-small cell lung carcinoma.

In particular, the compounds of the invention may be useful in the treatment of cancer where apoptotic pathways are dysregulated and more particularly where proteins of the BCL-2 family are mutated, or over or under expressed.

References to 'treatment' includes curative, palliative and prophylactic, and includes means to ameliorate, alleviate symptoms, eliminate the causation of the symptoms either on a temporary or permanent basis, or to prevent or slow the appearance of symptoms of the named disorder or condition. The compounds of the invention are useful in the treatment of humans and other mammals.

The compounds of the invention or pharmaceutical compositions thereof, as described herein, may be used alone or combined with one or more additional pharmaceutical agents. The compounds may be combined with an additional anti-tumour therapeutic agent, for example, chemotherapeutic drugs or inhibitors of other regulatory proteins. In one embodiment, the additional anti-tumour therapeutic agent is a BH-3 mimetic. In a further embodiment, BH-3 mimetics may be selected from but not limited to one or more of ABT-737, ABT-199, ABT-263, and Obatoclax. In a further embodiment, the additional anti-tumour agent is a chemotherapeutic agent. Chemotherapeutic agents may be selected from but not limited to, olaparib, mitomycin C, cisplatin, carboplatin, oxaliplatin, ionizing radiation (IR), camptothecin, irinotecan, topotecan, temozolomide, taxanes, 5-fluoropyrimidines, gemcitabine, and doxorubicin.

The pharmaceutical compositions of the invention may be administered in any suitably effective manner, such as oral, parenteral, topical, inhaled, intranasal, rectal, intravaginal, ocular, and andial. Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, ethanol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001).

A typical tablet may be prepared using standard processes known to a formulation chemist, for example, by direct compression, granulation (dry, wet, or melt), melt congealing, or extrusion. The tablet formulation may comprise one or more layers and may be coated or uncoated.

Examples of excipients suitable for oral administration include carriers, for example, cellulose, calcium carbonate, dibasic calcium phosphate, mannitol and sodium citrate, granulation binders, for example, polyvinylpyrrolidine, hydroxypropylcellulose, hydroxypropylmethylcellulose and gelatin, disintegrants, for example, sodium starch glycolat and silicates, lubricating agents, for example, magnesium stearate and stearic acid, wetting agents, for example, sodium lauryl sulphate, preservatives, anti-oxidants, flavours and colourants.

Solid formulations for oral administration may be formulated to be immediate and/or modified release. Modified release formulations include delayed-, sustained-, pulsed-, controlled dual-, targeted and programmed release. Details of suitable modified release technologies such as high energy dispersions, osmotic and coated particles are to be found in Verma et al, Pharmaceutical Technology On-line, 25 (2), 1-14 (2001). Other modified release formulations are described in U.S. Pat. No. 6,106,864.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by suitable processing, for example, the use of high energy spray-dried dispersions (WO 01/47495) and/or by the use of appropriate formulation techniques, such as the use of solubility-enhancing agents.

Formulations for parenteral administration may be formulated to be immediate and/or modified release. Modified release formulations include delayed-, sustained-, pulsed-, controlled dual-, targeted and programmed release.

Pharmaceutical compositions of the present invention also include compositions and methods known in the art for bypassing the blood brain barrier or can be injected directly into the brain. Suitable areas for injection include the cerebral cortex, cerebellum, midbrain, brainstem, hypothalamus, spinal cord and ventricular tissue, and areas of the PNS including the carotid body and the adrenal medulla.

Dosage

The magnitude of an effective dose of a compound will, of course, vary with the nature of the severity of the condition to be treated and the route of administration. The selection of appropriate dosages is within the remit of the physician. The daily dose range is about 10 μg to about 100 mg per kg body weight of a human and non-human animal and in general may be around 10 μg to 30 mg per kg body weight per dose. The above dose may be given from one to three times per day.

For example, oral administration may require a total daily dose of from 5 mg to 1000 mg, such as from 5 to 500 mg, while an intravenous dose may only require from 0.01 to 30 mg/kg body weight, such as from 0.1 to 10 mg/kg, more preferably from 0.1 to 1 mg/kg body weight. The total daily dose may be administered in single or divided doses.

The skilled person will also appreciate that, in the treatment of certain conditions, compounds of the invention may be taken as a single dose on an "as required" basis (i.e. as needed or desired).

All the compounds were characterised by liquid chromatography-mass spectroscopy (LCMS) or $^1$H NMR or both.

SYNTHETIC SCHEMES

Abbreviations:
AcOH Acetic acid
BINAP (2,2'-Bis(diphenylphosphino)-1,1'-binaphthyl)
CDI Carbonyldiimidazole
d Doublet (NMR signal)
dba dibenzylideneacetone
DCM Dichloromethane
DIPEA Diisopropylethylamine
DMSO Dimethylsulphoxide
dppf 1,1'-Bis(diphenylphosphino)ferrocene
ES Electrospray
EtOAc Ethyl acetate
EtOH Ethanol
h Hour(s)
HPLC High Performance Liquid Chromatography
m Multiplet (NMR signal)
MeCN Acetonitrile
MeOH Methanol
min Minute(s)
NMP N-Methyl-2-pyrrolidone
PE Petroleum Ether
rt Room temperature
RT Retention Time
s Singlet (NMR signal)
t Triplet (NMR signal)
TEA Triethylamine
TFA Trifluoroacetic acid
THF Tetrahydrofuran
TLC Thin layer chromatography Analytical Methods:

Method A

| | | |
|---|---|---|
| Column | X-bridge C18, 50 × 4.6 mm, 3.5 μm or equivalent | |
| Mobile Phase | (A) 0.1% Ammonia in water; (B) 0.1% Ammonia in MeCN | |
| Flow Rate | 1.0 ml/min | |

| | Time | % B |
|---|---|---|
| Gradient | 0.01 | 5 |
| | 5.00 | 90 |
| | 5.80 | 95 |
| | 7.20 | 95 |

Method B

| | | |
|---|---|---|
| Column | BEH C18, 50 × 2.1 mm, 1.7 μm or equivalent | |
| Mobile Phase | (A) 5 mM Ammonium acetate + 0.1% formic acid in water (B) 0.1% Formic acid in MeCN | |
| Flow Rate | 0.45 ml/min | |

| | Time | % B |
|---|---|---|
| Gradient | 0.01 | 2 |
| | 0.50 | 2 |
| | 5.00 | 90 |
| | 6.00 | 95 |
| | 7.00 | 95 |

Method C

| | | |
|---|---|---|
| Column | BEH C18, 50 × 2.1 mm, 1.7 μm or equivalent | |
| Mobile Phase | (A) 5 mM Ammonium acetate + 0.1% formic acid in water (B) 0.1% Formic acid in MeCN | |
| Flow Rate | 0.55 ml/min | |

| | Time | % B |
|---|---|---|
| Gradient | 0.01 | 5 |
| | 0.40 | 5 |
| | 0.80 | 35 |
| | 1.20 | 55 |
| | 2.50 | 100 |
| | 3.30 | 100 |

Method D

| | | |
|---|---|---|
| Column | Agilent TC-C18, 50 × 2.1 mm, 5 μm | |
| Mobile Phase | (A) 0.04% TFA in water; (B) 0.02% TFA in MeCN | |
| Flow Rate | 0.8 ml/min | |

| | Time | % B |
|---|---|---|
| Gradient | 0 | 0 |
| | 0.4 | 1 |
| | 3.4 | 100 |
| | 4 | 100 |
| Temperature | 50° C. | |

Method E

| | | |
|---|---|---|
| Column | XBridge ShieldRP18, 50 × 2.1 mm, 5 μm | |
| Mobile Phase | (A) 0.05% Ammonia in water; (B) MeCN | |
| Flow Rate | 0.8 ml/min | |

| | Time | % B |
|---|---|---|
| Gradient | 0 | 0 |
| | 0.4 | 5 |
| | 3.4 | 100 |
| | 4 | 100 |
| Temperature | 40° C. | |

Method F

| | | |
|---|---|---|
| Column | X-bridge C18, 250 × 4.6 mm, 5 μm or equivalent | |
| Mobile Phase | (A) 0.1% Ammonia in water; (B) 0.1% Ammonia in MeCN | |
| Flow Rate | 1.0 ml/min | |

| | Time | % B |
|---|---|---|
| Gradient | 0.01 | 5 |
| | 5.00 | 5 |
| | 10.00 | 30 |
| | 15.00 | 30 |
| | 25.00 | 60 |
| | 30.00 | 90 |
| | 35.00 | 90 |

Method G

| | | |
|---|---|---|
| Column | Gemini-NX C18, 150 × 4.6 mm, 5 μm | |
| Mobile Phase | (A) 0.1% TFA in water; (B) 0.1% TFA in MeCN | |
| Flow Rate | 1.0 ml/min | |

| | Time | % B |
|---|---|---|
| Gradient | 0 | 15 |
| | 20 | 45 |
| | 20.1 | 90 |
| | 23 | 90 |
| Temperature | 40° C. | |

Method H

| | | |
|---|---|---|
| Column | Gemini-NX C18, 150 × 4.6 mm, 5 μm | |
| Mobile Phase | (A) 0.1% TFA in water; (B) 0.1% TFA in MeCN | |
| Flow Rate | 1.0 ml/min | |

| | Time | % B |
|---|---|---|
| Gradient | 0 | 20 |
| | 20 | 50 |
| | 20.1 | 90 |
| | 23 | 90 |
| Temperature | 40° C. | |

Method I

| | | |
|---|---|---|
| Column | Gemini-NX C18, 150 × 4.6 mm, 5 μm | |
| Mobile Phase | (A) 0.1% TFA in water; (B) 0.1% TFA in MeCN | |
| Flow Rate | 1.0 ml/min | |

| | Time | % B |
|---|---|---|
| Gradient | 0 | 30 |
| | 20 | 60 |
| | 20.1 | 90 |
| | 23 | 90 |
| Temperature | 40° C. | |

Method J

| | | |
|---|---|---|
| Column | Gemini-NX C18, 150 × 4.6 mm, 5 μm | |
| Mobile Phase | (A) 0.1% TFA in water; (B) 0.1% TFA in MeCN | |
| Flow Rate | 1.0 ml/min | |

| | Time | % B |
|---|---|---|
| Gradient | 0 | 25 |
| | 20 | 55 |
| | 20.1 | 90 |
| | 23 | 90 |
| Temperature | 30° C. | |

-continued
| Method K | |
|---|---|
| Column | Sunfire C18, 250 × 4.6 mm, 5 μm |
| Mobile Phase | (A) 0.1% formic acid in water; (B) 0.1% formic acid in MeCN |
| Flow Rate | 1.0 ml/min |
| | Time | % B |
|---|---|---|
| Gradient | 0.01 | 10 |
| | 30 | 30 |
| | 35 | 90 |
| | 38 | 90 |
General Method A
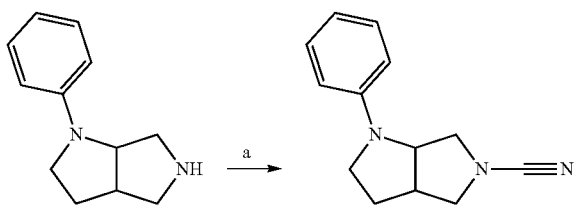 [SMILES: c1ccc(N2CCC3CNCC32)cc1 ; N#CN1CC2CCN(c3ccccc3)C2C1]
General Method B
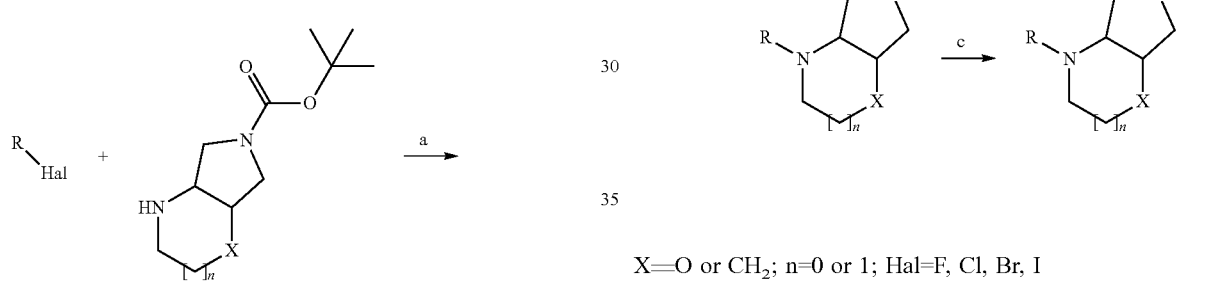
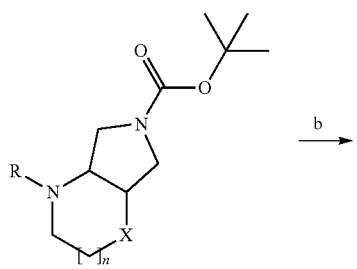
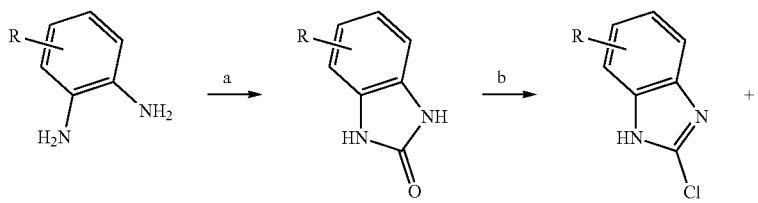
X=O or CH$_2$; n=0 or 1; Hal=F, Cl, Br, I
General Method C
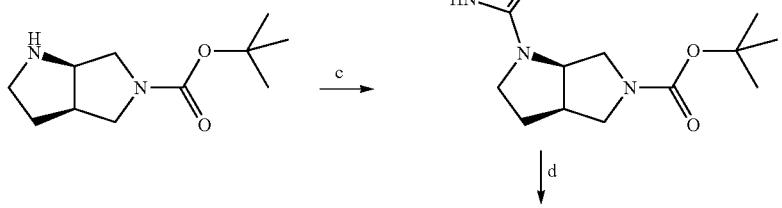

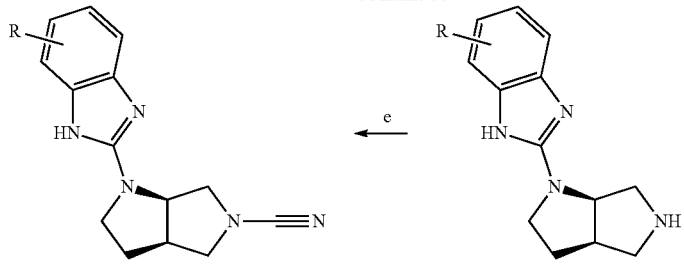

General Method D

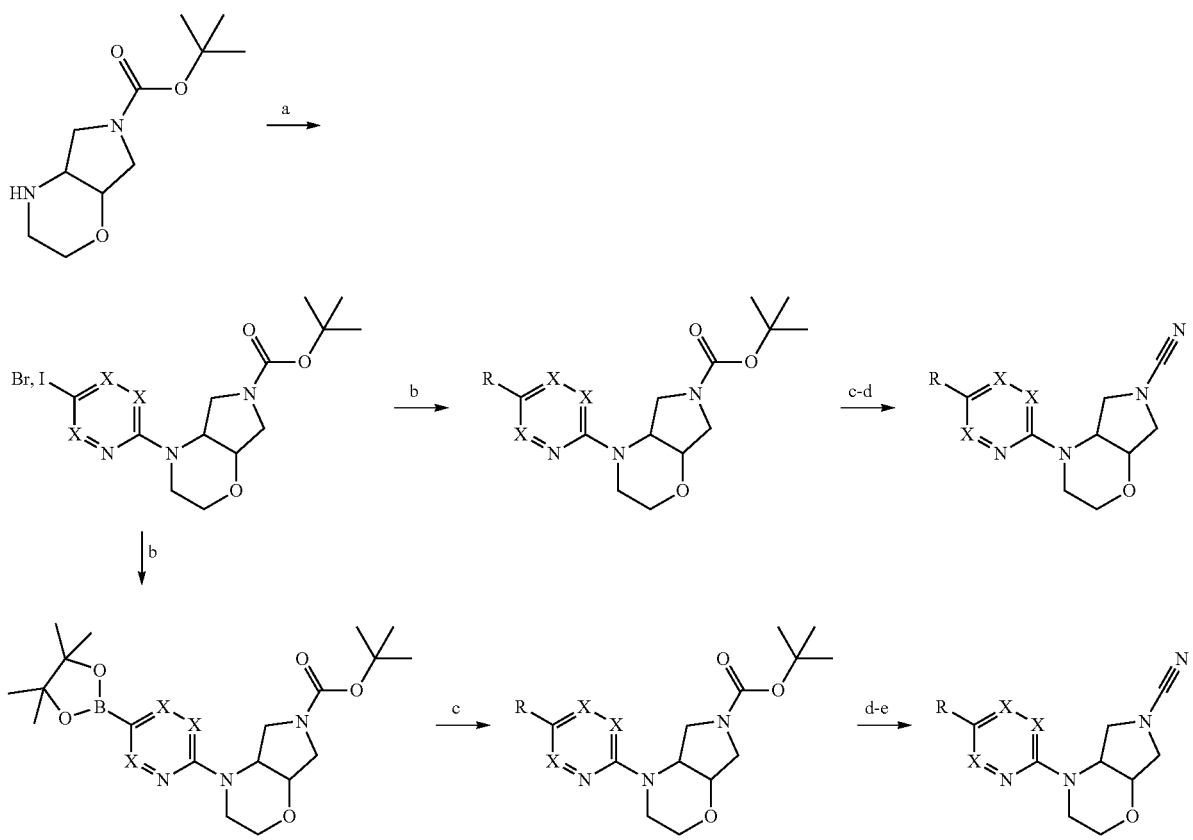

X=N or CH

Example 1 1-Phenylhexahydropyrrolo[3,4-b]pyrrole-5(1H)-carbonitrile (Prepared According to General Method A)

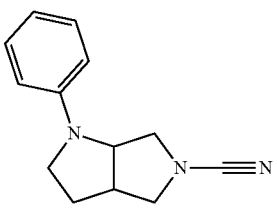 [SMILES: N#CN1CC2CCN(c3ccccc3)C2C1]

Step a.

To a solution of 1-phenyloctahydropyrrolo[3,4-b]pyrrole (CAS Number 128758-05-4; 0.050 g, 0.260 mmol) in DCM (2 ml) was added TEA (0.070 ml, 0.520 mmol) at rt. The reaction mixture was stirred at rt for 10 min. Cyanogen bromide (0.028 g, 0.260 mmol) was added to the reaction mixture at rt. The reaction mixture was stirred at rt for 30 min. The resulting reaction mixture was filtered and concentrated under reduced pressure. The resulting residue was purified by flash chromatography (15% EtOAc in hexane) yielding 1-phenylhexahydropyrrolo[3,4-b]pyrrole-5(1H)-carbonitrile (0.040 g, 0.187 mmol). LCMS: Method B, 3.051 min, MS: ES+ 213.99; $^1$H NMR (400 MHz, DMSO-d6) δ ppm: 7.16-7.19 (m, 2H), 6.63-6.67 (m, 1H), 6.52-6.54 (m, 2H), 4.10-4.18 (m, 1H), 3.63-3.67 (m, 1H), 3.47-3.54 (m, 2H), 3.30-3.34 (m, 1H), 3.16-3.24 (m, 2H), 3.00-3.04 (m, 1H), 2.08-2.16 (m, 1H), 1.81-1.99 (m, 1H).

Example 2 cis-4-(6-Phenylpyridazin-3-yl)hexahydropyrrolo[3,4-b][1,4]oxazine-6(2H)-carbonitrile (Prepared According to General Method B)

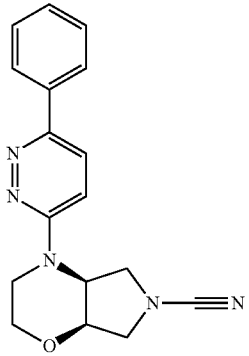 [SMILES: N#CN1C[C@H]2OCCN(c3ccc(-c4ccccc4)nn3)[C@H]2C1]

Step a.

To a solution of cis-tert-butyl hexahydropyrrolo[3,4-b][1,4]oxazine-6(2H)-carboxylate (CAS Number 138027-02-8; 0.2 mmol), 3-chloro-6-phenylpyridazine (0.2 mmol) and $Cs_2CO_3$ (0.6 mmol, 3 eq) in toluene (1 ml) were added $Pd_2(dba)_3$ (0.2 eq) and BINAP (0.06 eq) at rt under nitrogen. The reaction mixture was heated to 110° C. and stirred for 16 h. The resulting mixture was cooled to rt and concentrated under reduced pressure. The residue was purified by preparative-TLC (PE/EtOAc=1:1) yielding cis-tert-butyl 4-(6-phenylpyridazin-3-yl)hexahydropyrrolo[3,4-b][1,4]oxazine-6(2H)-carboxylate. MS: ES+ 383.4.

Step b.

To a solution of cis-tert-butyl 4-(6-phenylpyridazin-3-yl)hexahydropyrrolo[3,4-b][1,4]oxazine-6(2H)-carboxylate in EtOAc (1 ml) was added HCl/EtOAc (4 M, 1 ml). The reaction mixture was stirred at rt for 2 h. The resulting mixture was concentrated under reduced pressure. The residue cis-4-(6-phenylpyridazin-3-yl)octahydropyrrolo[3,4-b][1,4]oxazine was used for the next step. MS: ES+ 283.3.

Step c.

To a solution of cis-4-(6-phenylpyridazin-3-yl)octahydropyrrolo[3,4-b][1,4]oxazine in EtOH (2 ml) was added cyanogen bromide (0.2 mmol) and $NaHCO_3$ (0.6 mmol). The reaction mixture was stirred at rt for 16 h. The resulting mixture was concentrated under reduced pressure. The residue was purified by preparative reverse phase HPLC (A: 0.078% $CH_3CO_2NH_4$ in water, B: MeCN) to yield cis-4-(6-phenylpyridazin-3-yl)hexahydropyrrolo[3,4-b][1,4]oxazine-6(2H)-carbonitrile (14.51 mg, 0.047 mmol). LCMS: Method E, 2.083 min, MS: ES+ 308.1.

Compounds in Table 1 were synthesised according to general method B as exemplified by Example 2 using cis-tert-butyl hexahydropyrrolo[3,4-b][1,4]oxazine-6(2H)-carboxylate (CAS Number 138027-02-8).

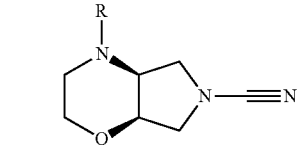

TABLE 1

| Ex | R | Name | LCMS Method | LCMS RT (min) | MS |
|---|---|---|---|---|---|
| 3 | ![F-benzothiazole] | cis-4-(6-Fluorobenzo[d]thiazol-2-yl)hexahydropyrrolo[3,4-b][1,4]oxazine-6(2H)-carbonitrile | D | 2.721 | ES+ 305.0 |
| 4 | ![4-phenylpyridine] | cis-4-(4-Phenylpyridin-2-yl)hexahydropyrrolo[3,4-b][1,4]oxazine-6(2H)-carbonitrile | D | 2.294 | ES+ 307.1 |

TABLE 1-continued

| Ex | R | Name | LCMS Method | LCMS RT (min) | MS |
|---|---|---|---|---|---|
| 5 | 5-phenylpyridin-2-yl | cis-4-(5-Phenylpyridin-2-yl)hexahydropyrrolo[3,4-b][1,4]oxazine-6(2H)-carbonitrile | D | 2.493 | ES+ 307.1 |
| 6 | 6-phenylpyridin-2-yl | cis-4-(6-Phenylpyridin-2-yl)hexahydropyrrolo[3,4-b][1,4]oxazine-6(2H)-carbonitrile | D | 3.001 | ES+ 307.2 |
| 7 | 4-phenylpyrimidin-2-yl | cis-4-(4-Phenylpyrimidin-2-yl)hexahydropyrrolo[3,4-b][1,4]oxazine-6(2H)-carbonitrile | D | 2.879 | ES+ 308.0 |

Example 8 cis-1-(5-Phenylthiazol-2-yl)hexahydro-pyrrolo[3,4-b]pyrrole-5(1H)-carbonitrile (Steps b-d According to General Method B)

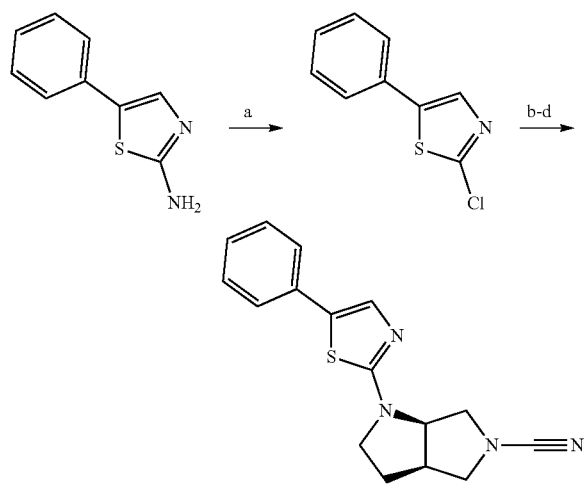

Step a.

To a stirring solution of 5-phenylthiazol-2-amine (5.0 g, 28.3 mmol, 1.0 eq) in HCl (40 ml) and AcOH (40 ml) was added NaNO$_2$ (2.3 g, 33.9 mmol, 1.2 eq) in water (10 ml) slowly at 0° C. After stirring at 0° C. for 0.5 h, CuCl$_2$ (7.6 g, 56.5 mmol, 2.0 eq) was added to the solution, and the mixture was stirred for 16 h at rt. The reaction mixture was extracted with DCM (400 ml×3). The combined organic layers were washed with brine, dried over Na$_2$SO$_4$, filtered and concentrated under reduced pressure. The residue was purified by column chromatography (PE/EtOAc=100:1 to 40:1) to yield 2-chloro-5-phenylthiazole (3.0 g, 99.0% purity) as yellow crystals.

Step b.

To a solution of cis-tert-butyl hexahydropyrrolo[3,4-b]pyrrole-5(1H)-carboxylate (CAS Number 180975-51-3; 0.4 mmol), 2-chloro-5-phenylthiazole (0.48 mmol) and sodium tert-butoxide (0.44 mmol, 1.1 eq) in toluene (3 ml) were added Pd(OAc)$_2$ (0.05 eq) and PPh$_3$ (0.05 eq) at rt under nitrogen. The reaction mixture was stirred at 110° C. for 16 h. The resulting mixture was concentrated under reduced pressure. The residue was purified by preparative-TLC (PE/EtOAc=1:1) yielding cis-tert-butyl 1-(5-phenylthiazol-2-yl)hexahydro-pyrrolo[3,4-b]pyrrole-5(1H)-carboxylate. MS: ES+372.5.

Step c.

To a solution of cis-tert-butyl 1-(5-phenylthiazol-2-yl)hexahydropyrrolo[3,4-b]pyrrole-5(1H)-carboxylate in EtOAc (3 ml) was added HCl/EtOAc (4 M, 3 ml). The reaction mixture was stirred at rt for 2 h. The resulting mixture was concentrated under reduced pressure. The residue cis-2-hexahydropyrrolo[3,4-b]pyrrol-1(2H)-yl)-5-phenylthiazole was used for next step directly. MS: ES+272.3.

Step d.

To a solution of cis-2-(hexahydropyrrolo[3,4-b]pyrrol-1(2H)-yl)-5-phenylthiazole in EtOH (4 mL) was added cyanogen bromide (0.4 mmol) and NaHCO$_3$ (1.2 mmol). The reaction mixture was stirred at rt for 16 h. The resulting mixture was concentrated under reduced pressure. The crude was purified by preparative reverse phase HPLC (A: 0.078% CH$_3$CO$_2$NH$_4$ in water, B: MeCN) to yield cis-1-(5-phenylthiazol-2-yl)hexahydropyrrolo[3,4-b]pyrrole-5(1H)-carbonitrile (20.2 mg, 0.068 mmol). LCMS: Method G, 11.206, MS: ES+ 296.8.

Example 9 cis-4-(5-Phenylthiazol-2-yl)hexahydropyrrolo[3,4-b][1,4]oxazine-6(2H)-carbonitrile

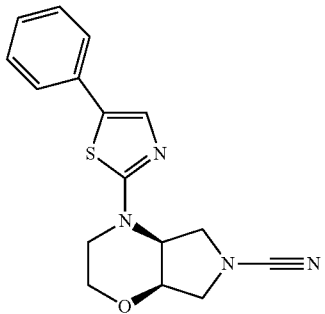 [SMILES: N#CN1C[C@H]2OCCN(c3ncc(-c4ccccc4)s3)[C@H]2C1]

The title compound was synthesised using a procedure similar to that described for Example 8, using cis-tert-Butyl hexahydropyrrolo[3,4-b][1,4]oxazine-6(2H)-carboxylate (CAS Number 138027-02-8/Intermediate 1) in step b. LCMS: Method H, 13.659, MS: ES+ 312.9; $^1$H NMR (400 MHz, CD$_3$OD) δ ppm: 7.49-7.51 (m, 3H), 7.35-7.39 (m, 2H), 7.24-7.28 (m, 1H), 4.63-4.88 (m, 1H), 4.19-4.21 (m, 1H), 4.06-4.10 (m, 1H), 3.74-3.85 (m, 3H), 3.50-3.57 (m, 3H), 3.39-3.46 (m, 1H).

Example 10 trans-4-(5-Phenylthiazol-2-yl)hexahydropyrrolo[3,4-b][1,4]oxazine-6(2H)-carbonitrile

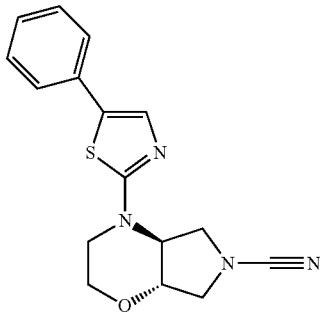 [SMILES: N#CN1C[C@@H]2OCCN(c3ncc(-c4ccccc4)s3)[C@H]2C1]

The title compound was synthesised using a procedure similar to that described for Example 8, using trans-tert-Butyl hexahydropyrrolo[3,4-b][1,4]oxazine-6(2H)-carboxylate (CAS Number 138026-93-4) in step b. LCMS: Method I, 15.077, MS: ES+ 312.8; NMR (400 MHz, CD$_3$OD) δ ppm: 7.50-7.52 (m, 3H), 7.36-7.39 (m, 2H), 7.26-7.28 (m, 1H), 4.47-4.51 (m, 1H), 4.13-4.16 (m, 1H), 3.95-3.96 (m, 1H), 3.82-3.85 (m, 1H), 3.69-3.73 (m, 2H), 3.57-3.59 (m, 1H), 3.37-3.40 (m, 1H), 3.21-3.25 (m, 1H).

Example 11 1-(5-Phenylthiazol-2-yl)octahydro-6H-pyrrolo[3,4-b]pyridine-6-carbonitrile (Prepared According to General Method B)

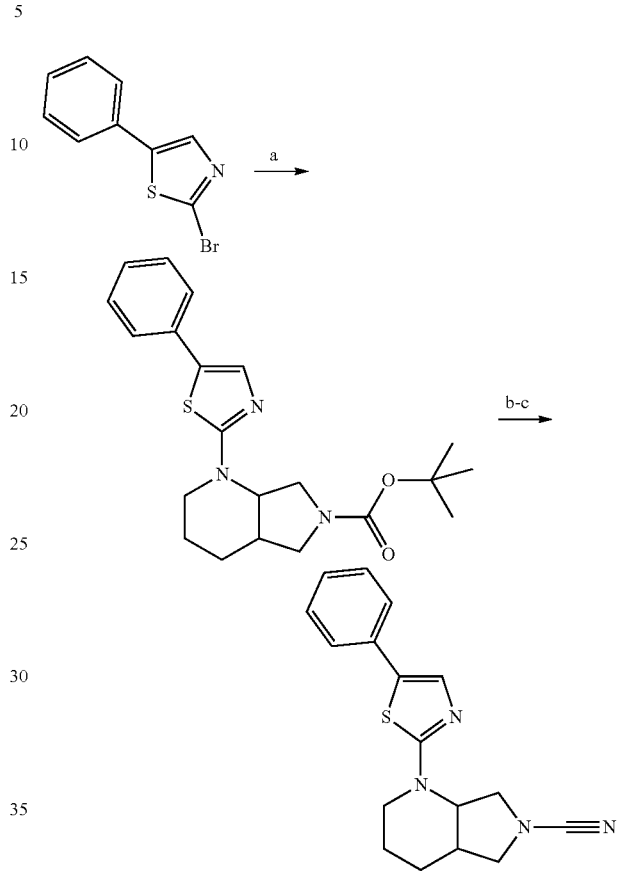

Step a.

To a solution of 2-bromo-5-phenylthiazole (CAS Number 133311-51-0; 0.158 g, 0.660 mmol) in toluene (5 ml) was added tert-butyl octahydro-6H-pyrrolo[3,4-b]pyridine-6-carboxylate (CAS Number 186203-81-6; 0.150 g, 0.660 mmol) at rt. Sodium tert-butoxide (0.120 g, 1.30 mmol) was added to the reaction mixture at rt. The resulting reaction mixture was degassed for 15 min and then treated with Pd$_2$(dba)$_3$ (0.030 g, 0.033 mmol) and Cy-JohnPhos (0.011 g, 0.033 mmol). The resulting reaction mixture was heated at 110° C. for 16 h then cooled to rt and poured into water (50 ml). The obtained mixture was extracted with EtOAc (3×20 ml). The combined organic phase was dried over Na$_2$SO$_4$, filtered and concentrated under reduced pressure. The residue was purified by flash chromatography (2% MeOH in DCM) yielding tert-butyl 1-(5-phenylthiazol-2-yl)octahydro-6H-pyrrolo[3,4-b]pyridine-6-carboxylate (0.163 g, 0.422 mmol). LCMS: Method C, 2.766 min, MS: ES+386.38.

Steps b-c.

The title compound was synthesised from the intermediate above using a procedure similar to that described for Example 8, steps c-d. LCMS: Method A, 4.926 min, MS: ES+ 310.93; $^1$H NMR (400 MHz, DMSO-d6) δ ppm: 7.71 (s, 1H), 7.56-7.69 (m, 2H), 7.34-7.48 (m, 2H), 7.20-7.28 (m, 1H), 4.72-4.78 (m, 1H), 3.58-3.66 (m, 3H), 3.42-3.46 (m, 1H), 3.01-3.24 (m, 2H), 2.28-2.32 (m, 1H), 1.77-1.80 (m, 2H), 1.35-1.56 (m, 2H).

Example 12 3-((5-Phenylthiazol-2-yl)amino)pyrrolidine-1-carbonitrile

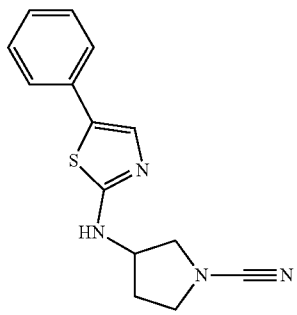 [SMILES: N#CN1CCC(Nc2ncc(-c3ccccc3)s2)C1]

The title compound was synthesised using a procedure similar to that described for Example 11. LCMS: Method B, 3.944 min, MS: ES+ 271.33; ¹H NMR (400 MHz, DMSO-d6) δ ppm: 8.18 (s, 1 H), 7.52 (s, 1H), 7.44-7.46 (m, 2H), 7.33-7.37 (m, 2H), 7.19-7.23 (m, 1H), 4.27-4.30 (m, 1H), 3.62-3.66 (m, 1H), 3.45-3.55 (m, 2H), 3.31-3.35 (m, 1H), 2.11-2.20 (m, 1H), 1.92-1.98 (m, 1H).

Example 13 3-(Methyl(5-phenylthiazol-2-yl)amino)pyrrolidine-1-carbonitrile

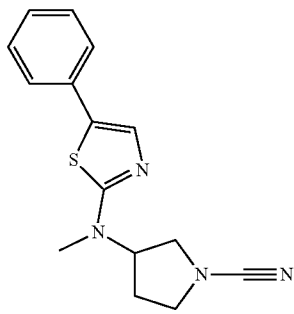 [SMILES: CN(c1ncc(-c2ccccc2)s1)C1CCN(C#N)C1]

The title compound was synthesised using a procedure similar to that described for Example 11. LCMS: Method B, 4.149 min, MS: ES+ 285.18; ¹H NMR (400 MHz, DMSO-d6) δ ppm: 7.62 (s, 1H), 7.46-7.49 (m, 2H), 7.34-7.38 (m, 2H), 7.20-7.23 (m, 1H), 4.86-4.89 (m, 1H), 3.55-3.64 (m, 2H), 3.44-3.50 (m, 2H), 3.00 (s, 3H), 2.10-2.17 (m, 2H).

Example 14 3-(Methyl(5-phenylpyridin-2-yl)amino)pyrrolidine-1-carbonitrile

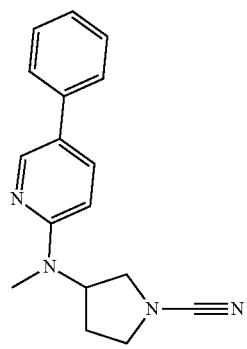 [SMILES: CN(c1ccc(-c2ccccc2)cn1)C1CCN(C#N)C1]

The title compound was synthesised using a procedure similar to that described for Example 11. LCMS: Method B, 3.265 min, MS: ES+ 279.33; ¹H NMR (400 MHz, DMSO-d6) δ ppm: 8.45 (d, J=2.4 Hz, 1H), 7.87 (dd, J=8.8, 2.4 Hz, 1H), 7.60-7.62 (m, 2H), 7.41-7.44 (m, 2H), 7.28-7.31 (m, 1H), 6.81 (d, J=9.2 Hz, 1H), 5.38-5.42 (m, 1H), 3.53-3.61 (m, 2H), 3.42-3.48 (m, 1H), 3.34-3.37 (m, 1H), 2.93 (s, 3H), 2.01-2.08 (m, 2H).

Example 15 (3aR,6aR)-1-(6-(Trifluoromethoxy)-1H-benzo[d]imidazol-2-yl)hexahydropyrrolo[3,4-b]pyrrole-5(1H)-carbonitrile (Prepared According to General Method C)

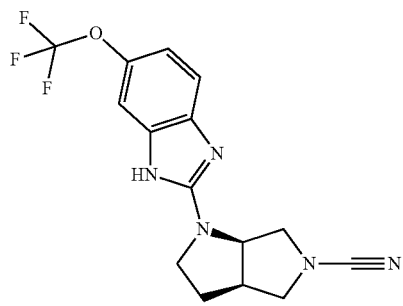 [SMILES: N#CN1C[C@H]2CCN(c3nc4ccc(OC(F)(F)F)cc4[nH]3)[C@H]2C1]

Step a.

To a solution of 4-(trifluoromethoxy)benzene-1,2-diamine (CAS Number 658-89-9; 0.45 g, 2.34 mmol) in DMF (5 ml) was added urea (0.28 g, 4.66 mmol) at rt. The resulting reaction mixture was heated at 150° C. for 20 h. The reaction mixture was diluted with water (5 ml) and the brown precipitate was collected by vacuum filtration and dried under reduced pressure to yield 5-(trifluoromethoxy)-1,3-dihydro-2H-benzo[d]imidazol-2-one (0.28 g, 1.28 mmol). LCMS: Method C, 2.118 min, MS: ES+ 219.

Step b.

A solution of mixture of 5-(trifluoromethoxy)-1,3-dihydro-2H-benzo[d]imidazol-2-one (0.25 g, 1.14 mmol) in POCl₃ (2 ml) was heated at 130° C. for 2 h. The resulting reaction mixture was cooled to rt and neutralised by slow addition of aqueous solution of K₂CO₃ (10 ml). The resulting mixture was extracted with EtOAc (3×60 ml). The combined organic phase was dried over Na₂SO₄, filtered and concentrated under reduced pressure. The resulting residue was washed with mixture of diethyl ether:hexane (9:1) and dried under reduced pressure to yield 2-chloro-6-(trifluoromethoxy)-1H-benzo[d]imidazole (0.18 g, 0.76 mmol). LCMS: Method C, 1.969 min, MS: ES+ 237.18; ¹H NMR (400 MHz, DMSO-d6) δ ppm: 13.63 (s 1H), 7.56-7.62 (m, 2H), 7.23-7.25 (m, 1H).

Step c.

To a solution of (3aR, 6aR)-hexahydro-pyrrolo[3,4-b]pyrrole-5-carboxylic acid tert-butyl ester (CAS Number 370882-39-6; 0.194 g, 0.91 mmol) in NMP (2 ml) was added DIPEA (0.245 g, 1.90 mmol) at rt. The reaction mixture was stirred at rt for 10 min. 2-Chloro-6-(trifluoromethoxy)-1H-benzo[d]imidazole (0.18 g, 0.76 mmol) was added to the reaction mixture at rt and then heated at 160° C. for 16 h. The resulting reaction mixture was cooled to rt and poured into water (30 ml). The obtained mixture was extracted with EtOAc (3×50 ml). The combined organic phase was washed with brine solution (100 ml), dried over Na₂SO₄, filtered and concentrated under reduced pressure. The resulting residue was purified by column chromatography (50% EtOAc in hexane) yielding tert-butyl (3aR, 6aR)-1-(6-(trifluoromethoxy)-1H-benzo[d]imidazol-2-yl)hexahydropyrrolo[3,4-b]pyrrole-5(1H)-carboxylate (0.16 g, 0.38 mmol). LCMS: Method C, 1.616 min, MS: ES+ 413.37.

Step d.

To a solution of tert-butyl (3aR, 6aR)-1-(6-(trifluoromethoxy)-1H-benzo[d]imidazol-2-yl) hexahydropyrrolo[3,4-b]pyrrole-5(1H)-carboxylate (0.16 g, 0.38 mmol) in DCM (2 ml) was added TFA (0.16 ml, 1.94 mmol) at 0° C. The reaction mixture was stirred at rt for 2 h. The resulting reaction mixture was concentrated under reduced pressure and the residue was further washed with diethyl ether (10 ml) yielding 2-((3aR,6aR)-hexahydropyrrolo[3,4-b]pyrrol-1(2H)-yl)-6-(trifluoromethoxy)-1H-benzo[d]imidazole TFA salt (0.16 g, 0.37 mmol). LCMS: Method C, 1.766 min, MS: ES+ 313.2.

Step e.

To a solution of 2-((3aR,6aR)-hexahydropyrrolo[3,4-b]pyrrol-1(2H)-yl)-6-(trifluoromethoxy)-1H-benzo[d]imidazole TFA salt (0.16 g, 0.37 mmol) in THF (2 ml) was added $K_2CO_3$ (0.155 g, 1.12 mmol) at rt. The reaction mixture was stirred at rt for 10 min. Cyanogen bromide (0.05 g, 0.48 g) was added to reaction mixture and stirred at rt for 30 min. The resulting reaction mixture was poured into water (10 ml) and extracted with EtOAc (3×50 ml). The combined organic phase was washed with brine solution (100 ml), dried over $Na_2SO_4$, filtered and concentrated under reduced pressure. The resulting residue was purified by column chromatography (40% EtOAc in hexane) yielding (3 aR,6aR)-1-(6-(trifluoromethoxy)-1H-benzo[d]imidazol-2-yl)hexahydropyrrolo[3,4-b]pyrrole-5(1H)-carbonitrile (0.04 g, 0.11 mmol). LCMS: Method A, 3.904 min, MS: ES+ 338, $^1$H NMR (400 MHz, DMSO-d6) δ ppm: 11.54-11.56 (m, 1H), 7.11-7.26 (m, 2H), 6.84-6.94 (m, 1H), 4.38-4.42 (m, 1H), 3.33-3.65 (m, 5H), 3.31-3.32 (m, 1H), 3.05-3.09 (m, 1H), 2.12-2.17 (m, 1H), 1.87-1.92 (m, 1H).

Example 16 2-((3aR,6aR)-5-Cyanohexahydropyrrolo[3,4-b]pyrrol-1(2H)-yl)-1H-benzo[d]imidazole-6-carbonitrile (Prepared According to General Method C)

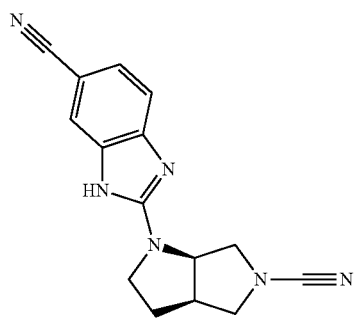 [SMILES: N#Cc1ccc2nc(N3CC[C@@H]4CN(C#N)C[C@@H]43)[nH]c2c1]

Step a.

To a solution of 3,4-diaminobenzonitrile (CAS Number 17626-40-3; 0.400 g, 3.00 mmol) in toluene (5 ml) was added CDI (0.633 g, 3.907 mmol) at rt. The resulting reaction mixture was heated at 125° C. for 2 h. The resulting reaction mixture was diluted with water (100 ml) and basified using 1M NaOH solution. The resulting mixture was extracted with EtOAc (3×100 ml) and the combined organic layer was dried over $Na_2SO_4$, filtered and concentrated under reduced pressure yielding 2-oxo-2,3-dihydro-1H-benzo[d]imidazole-5-carbonitrile (0.211 g, 1.327 mmol). LCMS: Method F, 4.066 min, MS: ES− 158.00; $^1$H NMR (400 MHz, DMSO-d6) δ ppm: 11.19 (s, 1H), 11.06 (s, 1H), 7.40 (dd, J=8.0, 1.2 Hz, 1H), 7.31 (d, J=1.2 Hz, 1H), 7.07 (d, J=8.0 Hz, 1H).

Steps b-e.

The title compound was synthesised from the intermediate above using a procedure similar to that described for Example 15 to provide the title compound. LCMS: Method B, 2.363 min, MS: ES+ 279.53; $^1$H NMR (400 MHz, DMSO-d6) δ ppm: 11.81-11.83 (m, 1H), 7.55-7.58 (m, 1H), 7.30-7.34 (m, 2H), 4.43-4.45 (m, 1H), 3.54-3.69 (m, 5H), 3.28-3.31 (m, 1H), 3.05-3.12 (m, 1H), 2.10-2.17 (m, 1H), 1.86-1.95 (m, 1H).

Example 17 (3aR,6aR)-1-(6-Methoxy-1H-benzo[d]imidazol-2-yl)hexahydropyrrolo[3,4-b]pyrrole-5(1H)-carbonitrile (Prepared According to General Method C)

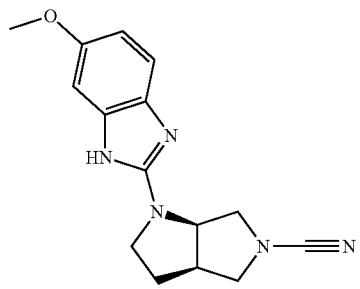 [SMILES: COc1ccc2nc(N3CC[C@@H]4CN(C#N)C[C@@H]43)[nH]c2c1]

The title compound was synthesised using a procedure similar to that described for Example 16. LCMS: Method B, 2.494 min, MS: ES+ 284.53; $^1$H NMR (400 MHz, DMSO-d6) δ ppm: 11.07-11.18 (m, 1H), 7.02-7.11 (m, 1H), 6.74-6.82 (m, 1H), 6.48-6.50 (m, 1H), 4.33-4.37 (m, 1H), 3.70 (s, 3H), 3.51-3.64 (m, 5H), 3.28-3.31 (m, 1H), 3.02-3.06 (m, 1H), 2.09-2.18 (m, 1H), 1.87-1.90 (m, 1H).

Example 18 (R)-3-(Methyl(6-(trifluoromethyl)-1H-benzo[d]imidazol-2-yl)amino)pyrrolidine-1-carbonitrile

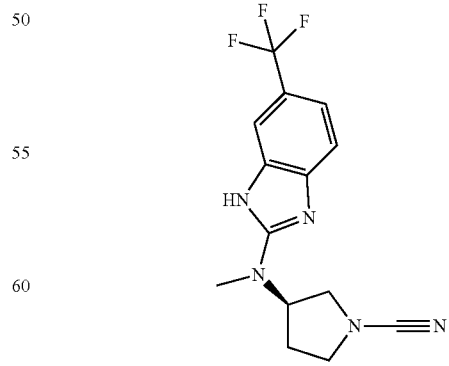

The title compound was synthesised using a procedure similar to that described for Example 16, using (R)-tert-butyl 3-(methylamino)pyrrolidine-1-carboxylate (CAS Number 199336-83-9) in step c. LCMS: Method A, 3.855 min, MS: ES+ 309.99; ¹H NMR (400 MHz, DMSO-d6) δ ppm: 11.70-11.75 (m, 1H), 7.22-7.47 (m, 3H), 5.01-5.2 (m, 1H), 3.59-3.61 (m, 2H), 3.34-3.45 (m, 2H), 3.01 (s, 3H), 2.06-2.14 (m, 2H).

Intermediate 1 cis-tert-Butyl hexahydropyrrolo[3,4-b][1,4]oxazine-6(2H)-carboxylate

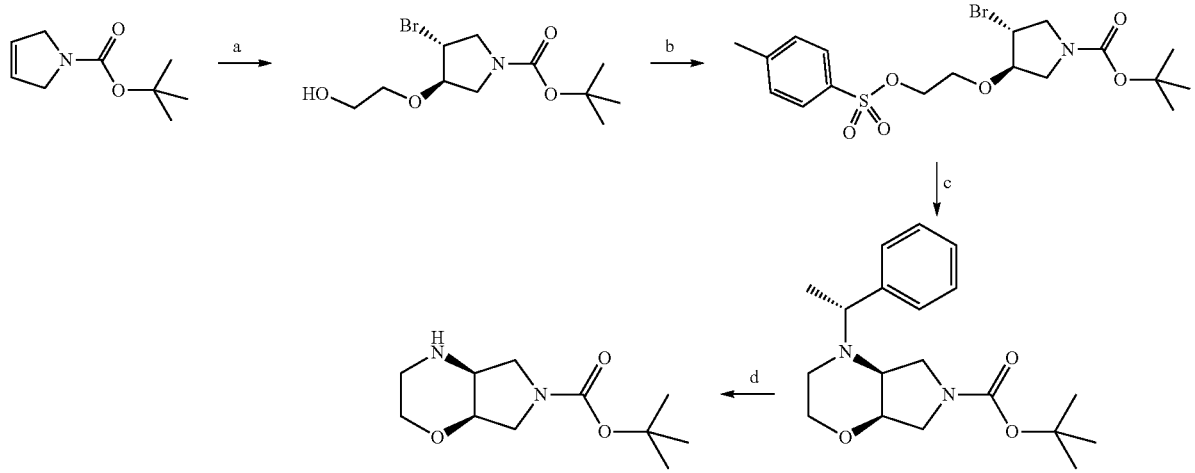

Step a.

To a stirred solution of tert-butyl 2,5-dihydro-1H-pyrrole-1-carboxylate (CAS Number 73286-70-1; 10.00 g, 59.17 mmol) in ethylene glycol (30 mL) was added N-bromosuccinimide (10.84 g, 60.95 mmol) portion-wise at rt under nitrogen and stirred for 16 h. The resulting mixture was diluted with water (100 mL) and extracted with EtOAc (2×100 mL). The combined organic extracts were dried over anhydrous $Na_2SO_4$, filtered and concentrated under reduced pressure. The resulting residue was purified by column chromatography (50% EtOAc in hexane) to yield tert-butyl 3-bromo-4-(2-hydroxyethoxy)pyrrolidine-1-carboxylate (11.74 g, 37.99 mmol). LCMS: Method C, 1.704 min, MS: ES+ 254.1, 256.1 (M-56).

Step b.

To a stirred solution of tert-butyl 3-bromo-4-(2-hydroxyethoxy)pyrrolidine-1-carboxylate (11.74 g, 37.99 mmol) in toluene (30 mL) was added TEA (6.34 mL, 45.6 mmol) and DMAP (0.139 g, 1.14 mmol) at rt. The reaction mixture was cooled to 0° C. and a solution of p-toluenesulfonyl chloride (8.69 g, 45.59 mmol) in toluene (20 mL) was added dropwise. The reaction was slowly warmed to rt and stirred for 16 h. The resulting reaction mixture was diluted with water (100 mL) and extracted with EtOAc (2×100 mL). The combined organic extracts were dried over anhydrous $Na_2SO_4$, filtered and concentrated under reduced pressure. The residue was purified by column chromatography (25% EtOAc in hexane) to yield tert-butyl 3-bromo-4-(2-(tosyloxy)ethoxy)pyrrolidine-1-carboxylate (13.43 g, 29.01 mmol). LCMS: Method C, 2.367 min, MS: ES+ 464.2, 466.1.

Step c.

To a stirred solution of tert-butyl 3-bromo-4-(2-(tosyloxy)ethoxy)pyrrolidine-1-carboxylate (13.43 g, 29.01 mmol) in NMP (80 mL) was added (R)-1-phenylethan-1-amine (CAS Number 3886-69-9; 10.52 g, 87.0 mmol) at rt and the resulting mixture was heated to 140° C. for 16 h. The reaction mixture was cooled to rt, diluted with water (100 mL) and extracted with EtOAc (2×100 mL). The combined organic extracts were further washed with water (5×100 mL), dried over anhydrous $Na_2SO_4$, filtered and concentrated under reduced pressure. The residue was purified by column chromatography (30% EtOAc in hexane) to yield tert-butyl 4-((R)-1-phenylethyl)hexahydropyrrolo[3,4-b][1,4]oxazine-6(2H)-carboxylate (6.80 g, 20.48 mmol). LCMS: Method K, 26.753, 27.019 min, MS: ES+ 333.2

Step d.

To a stirred solution of tert-butyl 4-((R)-1-phenylethyl)hexahydropyrrolo[3,4-b][1,4]oxazine-6(2H)-carboxylate (6.70 g, 20.18 mmol) in MeOH (90 mL), taken in a Parr autoclave, was added 10% (w/w) palladium on carbon (50% moist; 2.68 g) at rt and the resulting mixture was stirred under hydrogen at 250 psi at rt for 16 h. The resulting reaction mixture was filtered through a celite bed and the filtrate was concentrated under reduced pressure. The residue was purified by column chromatography (5-7% MeOH in DCM) to yield tert-butyl hexahydropyrrolo[3,4-b][1,4]oxazine-6(2H)-carboxylate (2.78 g, 1.22 mmol). LCMS: Method C, 1.369 min, MS: ES+ 229.19.

Example 19 cis-4-(2'-Cyano-[3,4'-bipyridin]-6-yl)hexahydropyrrolo[3,4-b][1,4]oxazine-6(2H)-carbonitrile (Enantiomer 1) and Example 20 cis-4-(2'-Cyano-[3,4'-bipyridin]-6-yl)hexahydropyrrolo[3,4-b][1,4]oxazine-6(2H)-carbonitrile (Enantiomer 2)

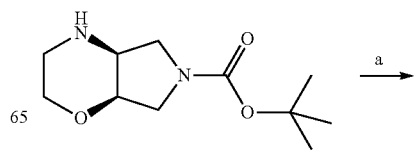

-continued

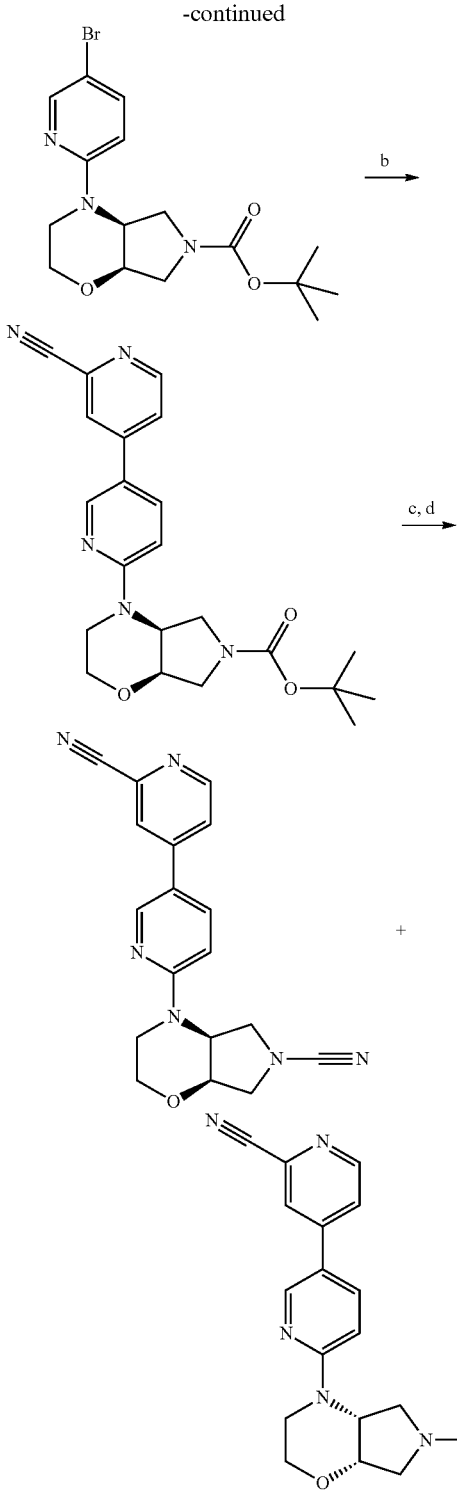

Step a.
To a mixture of tert-butyl hexahydropyrrolo[3,4-b][1,4]oxazine-6(2H)-carboxylate (Intermediate 1; 0.6 g, 2.63 mmol) and 5-bromo-2-iodopyridine (CAS Number 223463-13-6; 0.971 g, 3.42 mmol) in dry toluene (15 mL) was added sodium tert-butoxide (0.379 g, 3.945 mmol), Pd$_2$(dba)$_3$ (0.048 g, 0.053 mmol) and Xanthphos (0.091 g, 0.158 mmol) sequentially under nitrogen at rt and the resulting mixture was heated at 100° C. for 16 h. The reaction mixture was cooled to rt, diluted with water (40 mL) and extracted with EtOAc (2×40 mL). The combined organic extracts were dried over anhydrous Na$_2$SO$_4$, filtered and concentrated under reduced pressure. The residue was purified by flash column chromatography (12% EtOAc in hexane) to obtain tert-butyl 4-(5-bromopyridin-2-yl)-hexahydropyrrolo[3,4-b][1,4]oxazine-6(2H)-carboxylate (0.880 g, 2.30 mmol). LCMS: Method C, 2.324 min, MS: ES+ 328.07, 330.07 (M-56).

Step b.
To a mixture of tert-butyl 4-(5-bromopyridin-2-yl)hexahydropyrrolo[3,4-b][1,4]oxazine-6(2H)-carboxylate (0.230 g, 0.60 mmol) and 4-(4,4,5,5-tetramethyl-1,3,2-dioxaborolan-2-yl)picolinonitrile (CAS Number 741709-62-6; 0.207 g, 0.90 mmol) in DMF-water (5:1.5; 6.5 mL) was added NaHCO$_3$ (0.151 g, 1.802 mmol) at rt. The reaction mixture was degassed by purging nitrogen through the reaction solution for 15 min before addition of PdCl$_2$(dppf) (0.044 g, 0.06 mmol). The reaction mixture was heated to 100° C. for 1.5 h. The reaction was cooled to rt, diluted with water (40 mL) and extracted with EtOAc (2×40 mL). The combined organic extracts were dried over anhydrous Na$_2$SO$_4$, filtered and concentrated under reduced pressure. The resulting residue was purified by flash column chromatography (60% EtOAc in hexane) to provide tert-butyl 4-(2'-cyano-[3,4'-bipyridin]-6-yl)hexahydropyrrolo[3,4-b][1,4]oxazine-6(2H)-carboxylate (0.190 g, 0.47 mmol). LCMS: Method C, 2.069 min, MS: ES+ 352.22 (M-56).

Steps c, d.
The title compound was synthesised as a racemate from the intermediate above using a procedure similar to that described for Example 15, steps d, e. LCMS: Method B, 3.441 min, MS: ES+ 333.3; $^1$H NMR (400 MHz, DMSO-d6) δ ppm 8.77 (d, J=2.4 Hz, 1H), 8.72 (d, J=5.2 Hz, 1H), 8.44 (d, J=1.2 Hz, 1H), 8.19 (dd, J1=2.4 Hz & J2=8.8 Hz, 1H), 8.09 (dd, J1=2.0 Hz & J2=5.2 Hz, 1H), 7.05 (d, J=9.2 Hz, 1H), 4.98-4.92 (m, 1H), 4.11-4.09 (m, 1H), 4.04-3.99 (m, 2H), 3.75-3.71 (m, 1H), 3.62-3.58 (m, 2H), 3.46-3.34 (m, 2H), 3.17-3.10 (m, 1H).

The racemic mixture was separated by preparative chiral SFC, Waters SFC 200 with UV detector, 326 lambda max. Chiralcel OJ-H 250×21.0 mm, 5 micron, column flow was 80.0 ml/min and ABPR was 100 bar. Mobile phase (A) Liquid carbon dioxide; (B) 0.1% diethylamine/IPA; isocratic elution using 30% (A) over 16 minutes.

The first eluting isomer was assigned as Example 19; LCMS: Method B, 3.443 min, MS: ES+ 333.4; 1H NMR (400 MHz, DMSO-d6) δ ppm 8.78 (d, J=2.4 Hz, 1H), 8.72 (d, J=5.2 Hz, 1H), 8.45 (s, 1H), 8.20 (dd, J1=2.4 Hz & J2=8.8 Hz, 1H), 8.09 (dd, J1=2.0 Hz & J2=5.2 Hz, 1H), 7.06 (d, J=9.2 Hz, 1H), 4.98-4.94 (m, 1H), 4.13-4.11 (m, 1H), 4.06-4.06 (m, 2H), 3.76-3.72 (m, 1H), 3.65-3.60 (m, 2H), 3.46-3.34 (m, 2H), 3.18-3.12 (m, 1H); Chiral SFC: 6.96 min, Column: Chiralcel OJ-H, Eluent: Liquid carbon dioxide/ 0.1% diethylamine in IPA The second eluting isomer was assigned as Example 20; LCMS: Method B, 3.427 min, MS: ES+333.35; 1H NMR (400 MHz, DMSO-d6) δ ppm 8.78 (d, J=2.0 Hz, 1H), 8.71 (d, J=5.2 Hz, 1H), 8.43 (s, 1H), 8.18 (dd, J1=2.4 Hz & J2=9.2 Hz, 1H), 8.07-8.06 (m, 1H), 7.04 (d, J=9.2 Hz, 1H), 4.98-4.92 (m, 1H), 4.10-4.09 (m, 1H), 4.02-3.98 (m, 2H), 3.72 (dd, J1=3.6 Hz & J2=10.8 Hz, 1H), 3.63-3.58 (m, 2H), 3.44-3.36 (m, 2H), 3.15-3.05 (m, 1H); Chiral SFC: 7.72 min, column: Chiralcel OJ-H, Eluent: Liquid carbon dioxide/ 0.1% diethylamine in IPA

Example 21 cis-4-(6-(2-Cyanopyridin-4-yl)pyridazin-3-yl)hexahydropyrrolo[3,4-b][1,4]oxazine-6(2H)-carbonitrile (Enantiomer 1) and

Example 22 cis-4-(6-(2-Cyanopyridin-4-yl)pyridazin-3-yl)hexahydropyrrolo[3,4-b][1,4]oxazine-6(2H)-carbonitrile (Enantiomer 2)

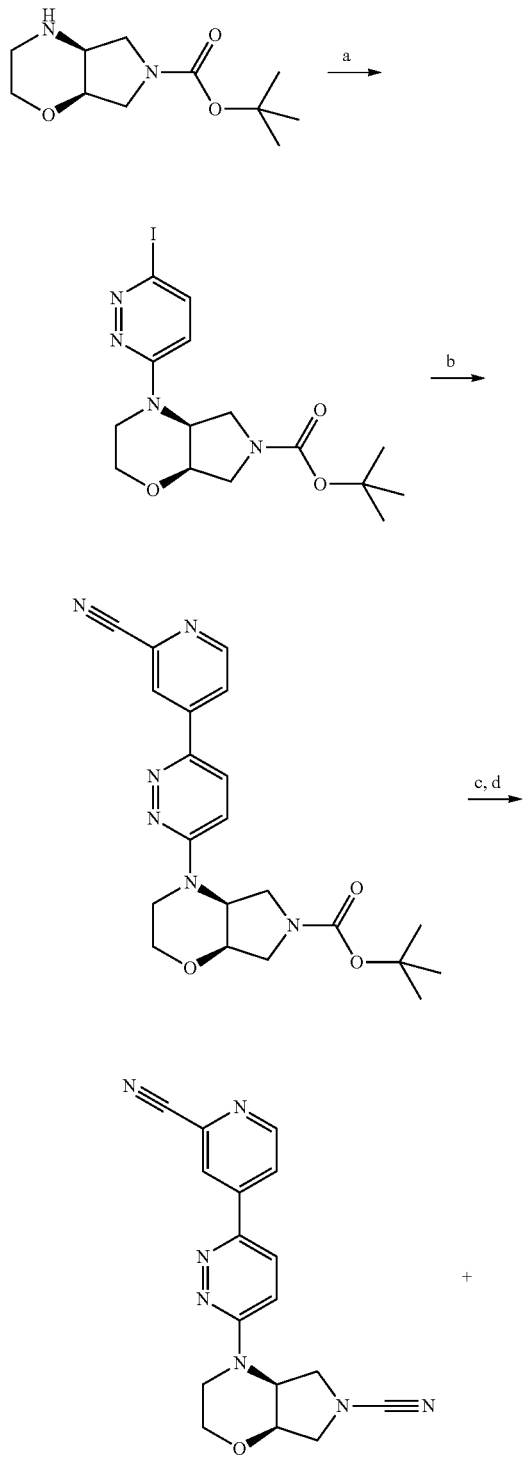

Step a.

To a stirred solution of 3-chloro-6-iodopyridazine (0.800 g, 3.33 mmol) and tert-butyl hexahydropyrrolo[3,4-b][1,4]oxazine-6(2H)-carboxylate (Intermediate 1; 0.758 g, 3.33 mmol) in DMSO (20 mL) was added KI (1.104 g, 6.65 mmol) and $K_2CO_3$ (1.377 g, 9.98 mmol) sequentially at rt and the resulting reaction mixture was heated at 100° C. for 24 h. The reaction mixture was poured into water (30 mL) and extracted with EtOAc (3×50 mL). The combined organic phases were washed with ice water (3×50 mL), dried over anhydrous $Na_2SO_4$, filtered and concentrated under reduced pressure. The resulting residue was purified by flash column chromatography (45% EtOAc in hexane) to provide tert-butyl 4-(6-iodopyridazine-3-yl)hexahydropyrrolo[3,4-b][1,4]oxazine-6(2H)-carboxylate (0.340 g, 0.79 mmol). LCMS: Method C, 1.605 min, MS: ES+ 433.45 Steps b-d.

The title compound was synthesised as a racemate from the intermediate above using a procedure similar to that described for Examples 19/20, steps b-d. LCMS: Method A, 2.945 min, MS: ES+ 334.0; $^1$H NMR (400 MHz, DMSO-d6) δ ppm 8.86 (d, J=5.2 Hz, 1H), 8.69 (s, 1H), 8.43 (dd, J1=1.6 Hz, J2=5.2 Hz, 1H), 8.29 (d, J=9.6 Hz, 1H), 7.52 (d, J=9.6 Hz, 1H), 5.04-5.03 (m, 1H), 4.18-4.06 (m, 3H), 3.76-3.65 (m, 2H), 3.49-3.40 (m, 2H), 3.29-3.23 (m, 2H).

The racemic mixture was separated by preparative chiral HPLC, Shimadzu LC-20AP with UV detector, 312 lambda max. Chiralpak AD-H 250×21.0 mm, 5 micron, column flow was 18.0 ml/min. Mobile phase (A) 0.1% diethylamine/hexane; (B) 0.1% diethylamine/IPA; isocratic elution using 50% (A) over 40 minutes.

The first eluting isomer was assigned as Example 21; LCMS: Method A, 2.966 min, MS: ES+ 334.2; $^1$H NMR (400 MHz, DMSO-d6) δ ppm 8.86 (d, J=5.2 Hz, 1H), 8.68 (s, 1H), 8.43 (dd, J1=1.6 Hz, J2=5.2 Hz, 1H), 8.29 (d, J=10 Hz, 1H), 7.52 (d, J=10 Hz, 1H), 5.06-5.02 (m, 1H), 4.18-4.05 (m, 3H), 3.76-3.65 (m, 2H), 3.49-3.40 (m, 2H), 3.29-3.22 (m, 2H); Chiral HPLC: 13.97 min, Column: Chiralpak AD-H, Eluent: 0.1% diethylamine in hexane/0.1% diethylamine in IPA The second eluting isomer was assigned as Example 22; LCMS: Method A, 2.965 min, MS: ES+334.2; $^1$H NMR (400 MHz, DMSO-d6) δ ppm 8.86 (d, J=5.2 Hz, 1H), 8.68 (s, 1H), 8.42 (dd, J1=1.6 Hz, J2=5.2 Hz, 1H), 8.29 (d, J=9.6 Hz, 1H), 7.52 (d, J=9.6 Hz, 1H), 5.06-5.01 (m, 1H), 4.18-4.05 (m, 3H), 3.76-3.65 (m, 2H), 3.49-3.35 (m, 2H), 3.29-3.22 (m, 2H); Chiral HPLC: 17.5 min, Column: Chiralpak AD-H, Eluent: 0.1% diethylamine in hexane/0.1% diethylamine in IPA Example 23 rac-(4aR,7aS)-4-(5-(3-Cyanophenyl)pyridin-6-yl)hexahydropyrrolo[3,4-b][1,4]oxazine-6(2H)-carbonitrile

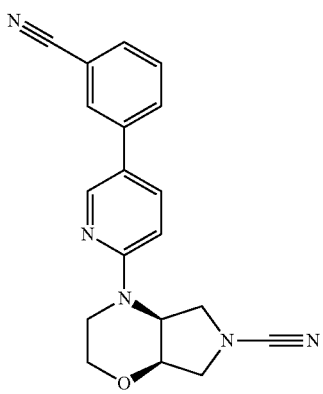 [SMILES: N#Cc1cccc(-c2ccc(N3CCO[C@@H]4CN(C#N)C[C@@H]43)nc2)c1]

The title compound was synthesised using a procedure similar to that described for Examples 19/20. LCMS: Method H run at 30° C., 10.731 min, MS: ES+ 332.0; $^1$H NMR (400 MHz, CDCl$_3$) δ ppm: 8.85 (s, 1H), 7.72 (s, 1H) 7.66 (m, 2H), 7.53 (dd, 1H), 7.48 (dd, 1H), 6.64 (d, 1H), 4.90 (m, 1H), 4.06 (m, 2H), 3.66 (m, 4H), 3.51 (m, 1H), 3.33 (m, 1H), 3.14 (m, 1H).

Example 24 rac-(4aR,7aS)-4-(5-(3-Cyanophenyl)pyrimidin-2-yl)hexahydropyrrolo[3,4-b][1,4]oxazine-6(2H)-carbonitrile

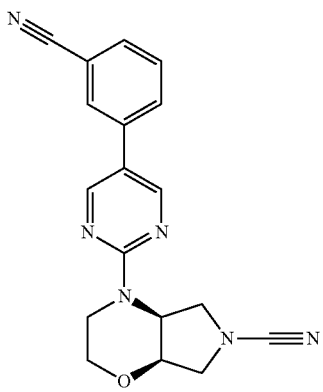 [SMILES: N#Cc1cccc(-c2cnc(N3CCO[C@@H]4CN(C#N)C[C@@H]43)nc2)c1]

The title compound was synthesised using a procedure similar to that described for Examples 19/20. LCMS: Method I run at 30° C., 13.070 min, MS: ES+ 333.0; $^1$H NMR (400 MHz, CDCl$_3$) δ ppm: 8.57 (s, 2H), 7.77 (s, 1H) 7.72 (dd, 1H), 7.66 (dd, 1H), 7.59 (m, 1H), 5.11 (m, 1H), 4.43 (m, 1H), 4.09 (m, 2H), 3.71 (m, 3H), 3.60 (m, 1H), 3.50 (m, 1H), 3.22 (m, 1H).

Example 25 rac-(4aR,7aS)-4-(5-(3-Cyanophenyl)pyrazin-2-yl)hexahydropyrrolo[3,4-b][1,4]oxazine-6(2H)-carbonitrile

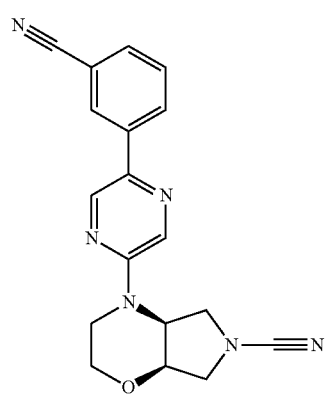 [SMILES: N#Cc1cccc(-c2cnc(N3CCO[C@@H]4CN(C#N)C[C@@H]43)cn2)c1]

The title compound was synthesised using a procedure similar to that described for Examples 19/20. LCMS: Method I run at 30° C., 12.751 min, MS: ES+ 332.9; $^1$H NMR (400 MHz, CDCl$_3$) δ ppm: 8.58 (s, 1H), 8.25 (s, 1H) 8.22 (s, 1H), 8.14 (dd, 1H), 7.66 (dd, 1H), 7.58 (m, 1H), 4.91 (m, 1H), 4.17 (m, 2H), 3.79 (m, 4H), 3.62 (m, 1H), 3.45 (m, 1H), 3.32 (m, 1H).

Example 26 rac-(4aR,7aS)-4-(4-Cyano-[2,3'-bipyridin]-6'-yl)hexahydropyrrolo[3,4-b][1,4]oxazine-6(2H)-carbonitrile

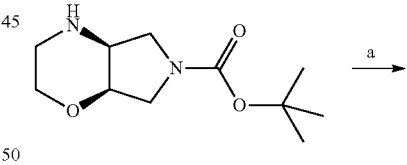

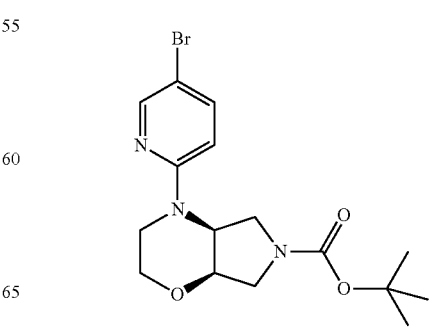

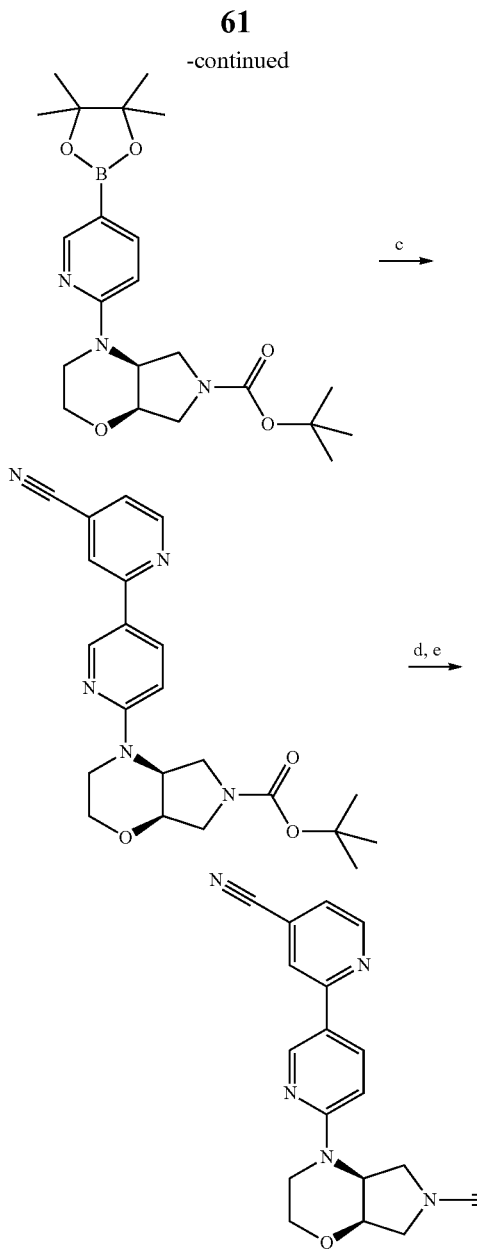

Step a.
A mixture of tert-butyl hexahydropyrrolo[3,4-b][1,4]oxazine-6(2H)-carboxylate (Intermediate 1; 1.12 g, 4.91 mmol), 5-bromo-2-iodo-pyridine (1.81 g, 6.38 mmol), Pd₂(dba)₃ (89.8 mg, 0.098 mmol), Xantphos (170 mg, 294 umol) and t-BuONa (707 mg, 7.36 mmol) in toluene (20.0 mL) was degassed and purged with N₂ 3 times, and then the mixture was stirred at 100° C. for 8 h under N₂ atmosphere. TLC indicated Intermediate 1 was consumed completely and one new spot (DCM:MeOH=10:1, Rf=0.71) formed. The reaction was clean according to TLC. The aqueous phase was extracted with EtOAc (3×20 ml). The combined organic phase was washed with brine (30 mL), dried with anhydrous Na₂SO₄, filtered and concentrated under vacuum. The residue was purified by silica gel chromatography (0-50% EtOAc/PE gradient) to provide racemic tert-butyl (4aS,7aR)-4-(5-bromopyridin-2-yl)-hexahydropyrrolo[3,4-b][1,4]oxazine-6(2H)-carboxylate (1.5 g, 3.90 mmol, 79.5% yield) as a yellow solid. ¹H NMR (400 MHz, CDCl₃) δ ppm: 8.15-8.12 (m, 1H), 7.53-7.48 (m, 1H), 6.47-6.44 (m, 1H), 4.68-4.58 (m, 1H), 4.00-3.97 (m, 2H), 3.65-3.44 (m, 5H), 3.14-3.08 (m, 2H), 1.37 (s, 9H).

Step b.
A mixture of tert-butyl (4aS,7aR)-4-(5-bromopyridin-2-yl)hexahydropyrrolo[3,4-b][1,4]oxazine-6(2H)-carboxylate (700 mg, 1.82 mmol), 4,4,5,5-tetramethyl-2-(4,4,5,5-tetramethyl-1,3,2-dioxaborolan-2-yl)-1,3,2-dioxaborolane (925 mg, 3.64 mmol), Pd(dppf)Cl₂ (53.3 mg, 0.073 mmol) and KOAc (536 mg, 5.46 mmol) in dioxane (10 mL) was degassed and purged with N₂ 3 times, and then the mixture was stirred at 100° C. for 12 h under N₂ atmosphere. LCMS showed reaction completion, one main peak (MS=350) with desired MS was detected. The crude product (700 mg, 1.62 mmol, 89.0% yield) was used into the next step without further purification.

Step c.
A mixture of the intermediate above (600 mg, 1.39 mmol) and 2-bromopyridine-4-carbonitrile (254 mg, 1.39 mmol) in dioxane (15 mL), Pd(PPh₃)₄ (129 mg, 111 umol) and Cs₂CO₃ (1.36 g, 4.17 mmol) in water (2 mL) was degassed and purged with N₂ for 3 times, and then the mixture was stirred at 105° C. for 20 hours under N₂ atmosphere. The aqueous phase was extracted with EtOAc (3×30 mL). The combined organic phase was washed with brine (50 mL), dried with anhydrous Na₂SO₄, filtered and concentrated under vacuum. The residue was purified by flash chromatography (0-60% EtOAc/PE gradient) to provide the desired intermediate (300 mg, 0.74 mmol, 52.9% yield) as a white solid.

Step d.
To a solution of the intermediate above (650 mg, 1.60 mmol) in EtOAc (3 mL) was added HCl/EtOAc (10 mL). The mixture was stirred at 25° C. for 3 h. The mixture was concentrated to obtain a residue, which was lyophilized to provide a crude product (200 mg, 736 umol, 98.9% yield), used in the next step without further purification.

Step e.
To a solution of the above crude intermediate (200 mg, 0.65 mmol) in EtOH (10 mL) was added NaHCO₃ (409 mg, 4.88 mmol) and cyanogen bromide (124 mg, 1.17 mmol). The mixture was stirred at 20° C. for 20 h. The mixture was concentrated to obtain a residue, which was purified by prep-HPLC (CH₃CH₂ONH₄ condition). The title compound was obtained as a yellow solid (80.0 mg, 24.6% yield). LCMS: Method H run at 30° C., 8.701 min, MS: ES+ 333.0; ¹H NMR (400 MHz, CDCl₃) δ ppm: 8.83 (m, 2H), 8.22 (dd, 1H), 7.87 (s, 1H), 7.41 (d, 1H), 6.74 (d, 1H), 5.03 (m, 1H), 4.15 (m, 2H), 3.76 (m, 4H), 3.60 (m, 1H), 3.43 (m, 1H), 3.25 (m, 1H).

Example 27 rac-(4aR,7aS)-4-(2-Cyano-[2,3'-bipyridin]-6'-yl)hexahydropyrrolo[3,4-b][1,4]oxazine-6(2H)-carbonitrile

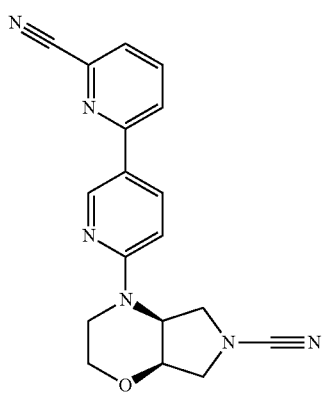 [SMILES: N#Cc1cccc(-c2ccc(N3CCO[C@@H]4CN(C#N)C[C@@H]43)nc2)n1]

The title compound was synthesised using a procedure similar to that described for Example 26. LCMS: Method J, 7.182 min, MS: ES+ 333.0; $^1$H NMR (400 MHz, CDCl$_3$) δ ppm: 8.83 (s, 1H), 8.30 (dd, 1H), 7.87 (m, 2H), 7.59 (dd, 1H), 6.74 (d, 1H), 5.03 (m, 1H), 4.14 (m, 2H), 3.76 (m, 4H), 3.60 (m, 1H), 3.43 (m, 1H), 3.25 (m, 1H).

Biological Activity of Compounds of the Invention

Abbreviations:

TAMRA carboxytetramethylrhodamine
PCR polymerase chain reaction
PBS phosphate buffered saline
EDTA ethylenediaminetetraacetic acid
Tris 2-amino-2-(hydroxymethyl)-1,3-propanediol
NP-40 Nonidet P-40, octylphenoxypolyethoxyethanol
BSA bovine serum albumin
PNS peripheral nervous system
BH3 Bcl-2 homology domain 3
PTEN phosphatase and tensin homologue In Vitro USP30 Inhibition Assay USP30 Biochemical Kinetic Assay.

Reactions were performed in duplicate in black 384 well plates (small volume, Greiner 784076) in a final reaction volume of 2411. USP30 CD (57-517, #64-0057-050 Ubiquigent) was diluted in reaction buffer (40 mM Tris, pH 7.5, 0.005% Tween 20, 0.5 mg/ml BSA, 5 mM beta-mercaptoethanol) to the equivalent of 0, 0.005, 0.01, 0.05, 0.1 and 0.5 μl/well. Buffer was optimised for optimal temperature, pH, reducing agent, salts, time of incubation, and detergent. Reactions were initiated by the addition of 50 nM of TAMRA labelled peptide linked to ubiquitin via an isopeptide bond as fluorescence polarisation substrate. Reactions were incubated at room temperature and read every 2 min for 120 min. Readings were performed on a Pherastar Plus (BMG Labtech). λ Excitation 540 nm; λ Emission 590 nm.

USP30 Biochemical IC50 Assay

Dilution plates were prepared at 21 times the final concentration (2100 μM for a final concentration of 100 μM) in 50% DMSO in a 96-well polypropylene V-bottom plate (Greiner #651201). A typical 8-point dilution series would be 100, 30, 10, 3, 1, 0.3, 0.1, 0.03 μM final. Reactions were performed in duplicate in black 384 well plates (small volume, Greiner 784076) in a final reaction volume of 21 μl. Either 1 μl of 50% DMSO or diluted compound was added to the plate. USP30 was diluted in reaction buffer (40 mM Tris, pH 7.5, 0.005% Tween 20, 0.5 mg/ml BSA, 5 mM beta-mercaptoethanol) to the equivalent of 0.05 μl/well and 10 μl of diluted USP30 was added to the compound. Enzyme and compound were incubated for 30 min at room temp. Reactions were initiated by the addition of 50 nM of TAMRA labelled peptide linked to ubiquitin via an isopeptide bond as fluorescence polarisation substrate. Reactions were read immediately after addition of substrate and following a 2 h incubation at room temperature. Readings were performed on a Pherastar Plus (BMG Labtech). Excitation 540 nm; Emission 590 nm.

Activity of Exemplary Compounds in USP30 Biochemical IC50 Assay

Ranges:
0.001<A*<0.01 μM;
0.01A<0.1 μM;
0.1<B<1 μM;
1<C<10 μM;
10<D<30 μM

| Example | IC50 range |
|---------|------------|
| 1 | C |
| 2 | B |
| 3 | C |
| 4 | C |
| 5 | B |
| 6 | B |
| 7 | B |
| 8 | B |
| 9 | B |
| 10 | B |
| 11 | C |
| 12 | D |
| 13 | C |
| 14 | C |
| 15 | A |
| 16 | B |
| 17 | B |
| 18 | B |
| 19 | A* |
| 20 | A |
| 21 | B |
| 22 | A |
| 23 | A* |
| 24 | A* |
| 25 | A* |
| 26 | A* |
| 27 | A |

The invention claimed is:

1. A compound of formula (IA)

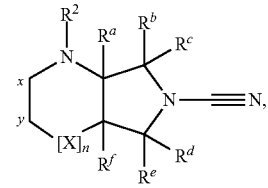

(IA)

or a tautomer thereof, or a pharmaceutically acceptable salt of said compound or tautomer, wherein:

R$_a$ is selected from hydrogen, cyano, and optionally substituted C$_1$-C$_3$ alkyl; or R$_a$ is linked to R$^b$ to form an optionally substituted C$_3$-C$_4$ cycloalkyl ring;

R$^b$, R$^c$, R$^d$ and R$^e$ are each independently selected from hydrogen, optionally substituted C$_1$-C$_3$ alkyl, and one or more spirocyclic groups where R$^b$ is linked to R$^c$, or R$^d$ is linked to R$^e$; or R$^b$ is linked to R$^a$ to form an optionally substituted C$_3$-C$_4$ cycloalkyl, or R$^e$ is linked to R$^f$ to form an optionally substituted C$_3$-C$_4$ cycloalkyl;

R$^f$ is selected from hydrogen, fluoro, cyano, optionally substituted C$_1$-C$_3$ alkyl, and optionally substituted C$_1$-C$_3$ alkoxy; or R$^f$ is linked to R$^e$ to form an optionally substituted C$_3$-C$_4$ cycloalkyl;

n is 0 or 1;

X is selected from O, N(R$^h$), and C(R$^i$)(R$^j$);

positions x and y may be optionally substituted;

R$^h$ is selected from hydrogen, C(O)R', optionally substituted C$_1$-C$_3$ alkyl, and optionally substituted 3 to 6-membered heterocyclyl, cycloalkyl, heteroaryl or aryl ring;

R' is selected from optionally substituted C$_1$-C$_3$ alkyl, and optionally substituted 3 to 10-membered monocyclic or bicyclic heteroaryl, aryl, heterocyclyl or cycloalkyl ring;

$R^i$ and $R^j$ are each independently selected from hydrogen, fluoro, cyano, optionally substituted $C_1$-$C_3$ alkyl, optionally substituted $C_1$-$C_3$ alkoxy, and optionally substituted 3 to 6-membered heterocyclyl, cycloalkyl, heteroaryl or aryl ring;

when X is O or $N(R^h)$, $R^f$ is not fluoro or optionally substituted $C_1$-$C_3$ alkoxy;

$R^2$ is a 5 to 10-membered, monocyclic or bicyclic, heteroaryl or aryl ring, which may be unsubstituted, or substituted with one or more $Q^1(R^3)_m$ groups, which may be the same or different;

m is 0 or 1;

$Q^1$ is selected from $Q^{1a}$ or $Q^{1b}$;

$Q^{1a}$ is selected from oxo, halo, cyano, nitro, hydroxyl, $SR^6$, $NR^6R^7$, $CONR^6R^7$, $C_0$-$C_3$-alkylene-$NR^6COR^7$, $NR^6CONR^7R^8$, $COR^6$, $C(O)OR^6$, $SO_2R^6$, $SO_2NR^6R^7$, $NR^6SO_2R^7$, $NR^6SO_2NR^7R^8$, $NR^6C(O)OR^7$, optionally substituted $C_1$-$C_6$ alkyl, optionally substituted $C_1$-$C_6$ alkoxy, and optionally substituted $C_2$-$C_6$ alkenyl;

$Q^{1b}$ is selected from a covalent bond, an oxygen atom, a sulphur atom, $OR^9$, SO, $SO_2$, CO, C(O)O, $C_0$-$C_3$ alkylene-C(O)$NR^6$—$C_0$-$C_3$ alkylene, $C_0$-$C_3$ alkylene-$NR^6$—$C_0$-$C_3$ alkylene, $C_0$-$C_3$ alkylene-$NR^6C(O)$—$C_0$-$C_3$ alkylene, $NR^6CONR^7$, $SO_2NR^6$, $NR^6SO_2$, $NR^6SO_2NR^7$, $NR^6C(O)O$, $NR^6C(O)OR^9$, optionally substituted $C_1$-$C_6$ alkylene, and optionally substituted $C_2$-$C_6$ alkenylene;

$R^3$ is a 3 to 10-membered, monocyclic or bicyclic, heterocyclyl, heteroaryl, cycloalkyl or aryl ring;

$R^6$, $R^7$ and $R^8$ are each independently selected from hydrogen and optionally substituted $C_1$-$C_6$ alkyl;

$R^9$ is optionally substituted $C_1$-$C_6$ alkylene;

wherein $R^3$ may be unsubstituted, or substituted with one or more substituents, each independently selected from halo, cyano, oxo, nitro, hydroxyl, $SR^{10}$, optionally substituted $C_1$-$C_6$ alkyl, optionally substituted $C_1$-$C_6$ alkoxy, optionally substituted $C_2$-$C_6$ alkenyl, optionally substituted $C_2$-$C_6$ alkynyl, $Q^{2a}$-$R^{13}$, $Q^{2a}$-O-$Q^{2b}$-$R^{13}$, $Q^{2a}$-S-$Q^{2b}$-$R^{13}$, $Q^{2a}$-SO-$Q^{2b}$-$R^{13}$, $Q^{2a}$-$NR^{10}CONR^{11}R^{12}$, $Q^{2a}$-$NR^{10}CONR^{11}$-$Q^{2a}$-$R^{13}$, $Q^{2a}$-$NR^{10}R^{11}$, $Q^{2a}$-$NR^{10}$-$Q^{2b}$-$R^{13}$, $Q^{2a}$-$COR^{10}$, $Q^{2a}$-CO-$Q^{2b}$-$R^{13}$, $Q^{2a}$-$NR^{10}COR^{11}$, $Q^{2a}$-$NR^{10}CO$-$Q^{2b}$-$R^{13}$, $Q^{2a}$-$NR^{10}C(O)OR^{11}$, $Q^{2a}$-$NR^{10}C(O)O$-$Q^{2b}$-$R^{13}$, $Q^{2a}$-$SO_2R^{10}$, $Q^{2a}$-$SO_2$-$Q^{2b}$-$R^{13}$, $Q^{2a}$-$CONR^{10}R^{11}$, $Q^{2a}$-$CONR^{10}$-$Q^{2b}$-$R^{13}$, $Q^{2a}$-$CO_2R^{10}$, $Q^{2a}$-$CO_2$-$Q^{2b}$-$R^{13}$, $Q^{2a}$-$SO_2NR^{10}R^{11}$, $Q^{2a}$-$SO_2NR^{10}$-$Q^{2b}$-$R^{13}$, $Q^{2a}$-$NR^{10}SO_2R^{11}$, $Q^{2a}$-$NR^{10}SO_2$-$Q^{2b}$-$R^{13}$, $Q^{2a}$-$NR^{10}SO_2NR^{11}R^{12}$, and $Q^{2a}$-$NR^{10}SO_2NR^{11}$-$Q^{2b}$-$R^{13}$;

$Q^{2a}$ and $Q^{2b}$ are each independently selected from a covalent bond, optionally substituted $C_1$-$C_6$ alkylene, and optionally substituted $C_2$-$C_6$ alkenylene;

$R^{10}$, $R^{11}$ and $R^{12}$ are each independently selected from hydrogen and optionally substituted $C_1$-$C_6$ alkyl; and $R^{13}$ is selected from optionally substituted heterocyclyl, optionally substituted heteroaryl, optionally substituted aryl, and optionally substituted cycloalkyl.

2. A compound of formula (IA) according to claim 1, wherein $R^2$ is selected from 5 to 10-membered aryl, and a 5 to 6-membered monocyclic, or a 9 to 10-membered bicyclic, heteroaryl ring, which comprises 1 to 4 heteroatoms independently selected from nitrogen, oxygen and sulfur; wherein $R^2$ is unsubstituted, or substituted with a $Q^1(R^3)_m$ group, which is selected from:
(i) halo, cyano, $C_1$-$C_3$ alkyl, $C_1$-$C_3$ haloalkyl, $C_1$-$C_3$ alkoxy, and $C_1$-$C_3$ haloalkoxy; and
(ii) phenyl, and a 5 to 6-membered, monocyclic heteroaryl, which comprises 1 to 3 heteroatoms independently selected from nitrogen, oxygen and sulfur, wherein the phenyl or heteroaryl ring is unsubstituted, or substituted with a group selected from halo, cyano, $C_1$-$C_3$ alkyl, $C_1$-$C_3$ haloalkyl, $C_1$-$C_3$ alkoxy, and $C_1$-$C_3$ haloalkoxy.

3. A compound of formula (IA) according to claim 2, wherein $R^2$ is an unsubstituted, or substituted, 5 to 6-membered monocyclic, or a 9 to 10-membered bicyclic, heteroaryl ring, which comprises 1 to 4 heteroatoms independently selected from nitrogen, oxygen and sulfur, wherein $R^2$ is unsubstituted, or substituted with a $Q^1(R^3)_m$ group, which is selected from:
(i) halo, cyano, $C_1$-$C_3$ alkyl, $C_1$-$C_3$ haloalkyl, $C_1$-$C_3$ alkoxy, and $C_1$-$C_3$ haloalkoxy; and
(ii) phenyl, and a 5 to 6-membered, monocyclic heteroaryl, which comprises 1 to 3 heteroatoms independently selected from nitrogen, oxygen and sulfur, wherein the phenyl or heteroaryl ring is unsubstituted, or substituted with a group selected from halo, cyano, $C_1$-$C_3$ alkyl, $C_1$-$C_3$ haloalkyl, $C_1$-$C_3$ alkoxy, and $C_1$-$C_3$ haloalkoxy.

4. A compound of formula (IA) according to claim 2, wherein $R^2$ is selected from benzimidazolyl, benzothiazolyl, pyrazinyl, pyridazinyl, pyridinyl, pyrimidinyl, thiazolyl, and phenyl; wherein $R^2$ is unsubstituted, or substituted by a $Q^1(R^3)_m$ group, which is selected from fluoro, cyano, methoxy, $CF_3$, $OCF_3$, phenyl, pyridinyl, cyanophenyl, and cyanopyridinyl.

5. A compound of formula (IA) according to claim 1, which is selected from (IIA)(i), (IIB)(i), and (IIC)(i):

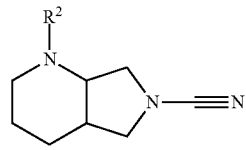

(IIA)(i)

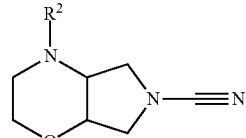

(IIB)(i)

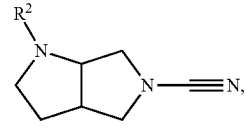

(IIC)(i)

or a tautomer thereof, or a pharmaceutically acceptable salt of said compound or tautomer.

6. A pharmaceutical composition, comprising a compound according to claim 1 together with one or more pharmaceutically acceptable excipients.

7. A method of treatment of a disorder or condition mediated by USP30, wherein inhibiting USP30 results in treating said disorder or condition, in a mammal having said disorder or condition, comprising administering to said mammal a therapeutically effective amount of a compound as defined in claim 1, a tautomer thereof, or a pharmaceutically acceptable salt of said compound or tautomer.

8. The method according to claim 7, wherein the disorder or condition is a condition involving mitochondrial dysfunction.

9. The method, according to claim 8, wherein the disorder or condition involving mitochondrial dysfunction is selected from a CNS disorder; neurodegenerative disease; multiple sclerosis (MS); mitochondrial myopathy; encephalopathy; lactic acidosis; stroke-like episodes (MELAS) syndrome; Leber's hereditary optic neuropathy (LHON); cancer; neuropathy; ataxia; retinitis pigmentosa; maternally inherited Leigh syndrome (NARP-MILS); Danon disease; diabetic nephropathy; metabolic disorders; heart failure; ischemic heart disease leading to myocardial infarction; psychiatric diseases; multiple sulfatase deficiency (MSD); mucolipidosis II (ML II); mucolipidosis III (ML III); mucolipidosis IV (ML IV); GM1-gangliosidosis (GM1); neuronal ceroid-lipofuscinoses (NCL1); Alpers disease; Barth syndrome; chronic progressive external ophthalmoplegia syndrome (CPEO); myoclonic epilepsy and ragged-red fiber (MERRF) syndrome; mitochondrial cytopathy; mitochondrial DNA depletion syndrome; myoneurogastrointestinal disorder and encephalopathy; Pearson syndrome; and age-dependent decline in cognitive function and muscle strength.

10. The method, according to claim 9, wherein the neurodegenerative disease is selected from Parkinson's disease, Alzheimer's disease, amyotrophic lateral sclerosis (ALS), Huntington's disease, dementia with Lewy bodies, and frontotemporal dementia.

11. The method, according to claim 7, wherein the disorder or condition is selected from ischemia and stroke.

12. The method, according to claim 10, wherein the neurodegenerative disease is selected from Parkinson's disease related to mutations in α synuclein, parkin and PINK1, and autosomal recessive juvenile Parkinson's disease (AR-JP).

13. The method, according to claim 7, wherein the disorder or condition is cancer.

14. The method according to claim 13, wherein the cancer is selected from breast, ovarian, prostate, lung, kidney, gastric, colon, testicular, head and neck, pancreas, brain, melanoma, bone cancer, cancer of tissue organs, and cancers of the blood cells.

15. The method according to claim 14, wherein the cancer is lymphoma, leukaemia, multiple myeloma, colorectal cancer, or non-small cell lung carcinoma.

16. The method, according to claim 7, wherein the disorder or condition is cancer and the cancer is selected from cancer where apoptotic pathways are dysregulated; and cancer where proteins of the BCL-2 family are mutated, or over or under expressed.

17. The method, according to claim 9, wherein the disorder or condition involving mitochondrial dysfunction is mitochondrial recessive ataxia syndrome.

18. The method, according to claim 9, wherein the disorder or condition involving mitochondrial dysfunction is selected from diabetes; Beta-oxidation defects; carnitine-acyl-carnitine deficiency; carnitine deficiency; creatine deficiency syndromes; co-enzyme Q10 deficiency; complex I deficiency; complex II deficiency; complex III deficiency; complex IV deficiency; complex V deficiency; COX deficiency; CPT I deficiency; CPT II deficiency; glutaric aciduria type II; Kearns-Sayre syndrome; lactic acidosis; long-chain acyl-CoA dehydrogenase deficiency (LCHAD); Leigh disease or syndrome; lethal infantile cardiomyopathy (LIC); Luft disease; glutaric aciduria type II; medium-chain acyl-CoA dehydrogenase deficiency (MCAD); pyruvate dehydrogenase deficiency; pyruvate carboxylase deficiency; POLG mutations; medium/short-chain 3-hydroxyacyl-CoA dehydrogenase (M/SCHAD) deficiency; and very long-chain acyl-CoA dehydrogenase (VLCAD) deficiency.

19. The method, according to claim 9, wherein the disorder or condition involving mitochondrial dysfunction is selected from schizophrenia, Parkinson's disease related to mutations in α synuclein, and autosomal recessive juvenile Parkinson's disease (AR-JP) where parkin is mutated.

\* \* \* \* \*